US009603860B2

(12) United States Patent
Perrin et al.

(10) Patent No.: US 9,603,860 B2
(45) Date of Patent: Mar. 28, 2017

(54) PHARMACEUTICAL COMPOSITIONS COMPRISING ACTIVE DRUGS, CONTRACEPTIVE KITS COMPRISING ACTIVE DRUGS, AND METHODS OF ADMINISTERING THE SAME

(71) Applicant: LABORATORIOS LEON FARMA SA, Navatejera Villaquilambre (ES)

(72) Inventors: Philippe Perrin, Paris (FR); Dominique Drouin, Verrieres (FR); Cécile Boyer-Joubert, Fontenay aux Roses (FR)

(73) Assignee: LABORATORIOS LEON FARMA SA, Navatejera Villaquilambre (ES)

( * ) Notice: Subject to any disclaimer, the term of this patent is extended or adjusted under 35 U.S.C. 154(b) by 0 days.

(21) Appl. No.: 14/748,147

(22) Filed: Jun. 23, 2015

(65) Prior Publication Data
US 2015/0290222 A1 Oct. 15, 2015

Related U.S. Application Data

(63) Continuation-in-part of application No. 13/171,410, filed on Jun. 28, 2011.

(60) Provisional application No. 61/368,396, filed on Jul. 28, 2010.

(51) Int. Cl.
*A61K 31/56* (2006.01)
*A61K 31/585* (2006.01)
*A61K 9/20* (2006.01)
*A61K 31/567* (2006.01)

(52) U.S. Cl.
CPC .......... *A61K 31/585* (2013.01); *A61K 9/2054* (2013.01); *A61K 31/567* (2013.01)

(58) Field of Classification Search
CPC ............. A61K 31/585; A61K 2300/00; A61K 31/567; A61K 9/2054; A61K 31/56; A61K 45/06; A61K 9/14; A61K 9/2018
See application file for complete search history.

(56) References Cited

U.S. PATENT DOCUMENTS

| 4,129,564 A | 12/1978 | Wiechert et al. | |
| 5,314,506 A * | 5/1994 | Midler, Jr. ........... | B01D 9/0009 137/896 |
| 2004/0087563 A1* | 5/2004 | Mayerhofer ........... | A61K 31/57 514/177 |
| 2006/0293295 A1 | 12/2006 | Strothmann et al. | |

FOREIGN PATENT DOCUMENTS

| DE | 3022337 A1 | 1/1982 | |
| EC | SP-07-7844 | 10/2007 | |
| UY | WO 2006015956 A1 * | 2/2006 | ........... A61K 31/565 |
| WO | 98/06738 | 2/1998 | |
| WO | 01/15701 A1 | 3/2001 | |
| WO | 01/52857 A1 | 7/2001 | |
| WO | 2005/087199 A2 | 9/2005 | |
| WO | 2005/105103 A2 | 11/2005 | |
| WO | 2006/015956 A1 | 2/2006 | |
| WO | 2006/061309 | 6/2006 | |
| WO | 2006/138503 A2 | 12/2006 | |
| WO | 2008/003432 A1 | 1/2008 | |
| WO | 2009/036999 A1 | 3/2009 | |
| WO | 2009/100871 A2 | 8/2009 | |
| WO | WO 2009138224 A1 * | 11/2009 | ............ A61K 9/146 |
| WO | 2010/015713 A1 | 2/2010 | |
| WO | 2012/000981 | 1/2012 | |

OTHER PUBLICATIONS

Micronor medical review, Jan. 17, 1972.
Arias, R.D. et al., Changes in bleeding patterns with depot medroxyprogesterone acetate subcutaneous injection 104 mg. Contraception 74 (2006) 234-238.
Dinger, J.C. et al., Oral contraceptive effectiveness according to body mass index, weight, age, and other factors. Am J Obstet Gynecol, vol. 201, No. 3, 2009:263.e1-263.e9.
Krattenmacher, R, Drospirenone:pharmacology and pharmacokinetics of a unique progestogen, Contraception, (2000) vol. 62, pp. 29-38.
Puthli, S et al., Formulation and Performance Characterization of Radio-sterilized "Progestin-only" Microparticles Intended for Contraception, AAPS PharmSciTech, (2009) vol. 10 No. 2.
The Merck Index, An Encyclopedia of Chemicals, Drugs, and Biologicals, 2006, p. 585.
Abdollahi, M. et al., Obesity: risk of venous thrombosis and the interaction coagulation factor levels and oral aontraceptive use Thromb. Haemost. 2003;89 (3):493-498.
Blanco-Molina, M.A. et al., Progestin-only contraception and venous thromboembolism. Thrombosis Research. 2012;129:e257-e262.
Casey, P.M. et al., Association of body mass index with removal of etonogestrel subdermal implant. 2013, Contraception, vol. 87 : 370-374.
Cedergren, M.I., Maternal Morbid Obesity and the Risk of Adverse Pregnancy Outcome. Obstet. Gynecol. 2004;103:219-24.
Centers for Disease Control and Prevention, U.S. Medical Eligibility Criteria for Contraceptive Use, 2010. MMWR Early Release 2010;59:1-86.

(Continued)

Primary Examiner — Jean Cornet
(74) Attorney, Agent, or Firm — Don J. Pelto, Esq.; Sheppard, Mullin, Richter & Hampton LLP

(57) ABSTRACT

A pharmaceutical composition comprising an active contraceptive drug and one or more pharmaceutically-acceptable excipients. The pharmaceutical composition, when subjected to an in vitro dissolution test according to the USP XXIII Paddle Method, results in no more than 50% of said active drug initially present being dissolved within 30 minutes, and at least 50% of the active drug being dissolved in a time range from about 3 hours to about 4 hours. The pharmaceutical composition is administered daily to a patient having a BMI of about 25 kg/m$^2$ or more for at least a portion of a treatment cycle. The pharmaceutical composition does not cause a number of days of bleeding events in the patient exceeding an average of 15% per treatment cycle in consecutive treatment cycles of administration after an initial treatment cycle of administration.

40 Claims, 11 Drawing Sheets

(56) References Cited

OTHER PUBLICATIONS

Connor, P.D. et al., Determining Risk Between Depo-Provera Use and Increased Uterine Bleeding in Obese and Overweight Women. J. Am. Borad Fam. Pract., 2002, vol. 15(1) : 7-10.

Curtis, K.M. et al., Progestogen-only contraceptive use in obese women. Contraception 2009;80(4):346-354.

Dragoman, M. et al., Contraceptive vaginal ring effectiveness is maintained during six weeks use: A prospective study of normal BMI and obese women. Contraception. Apr. 2013; 87(4): 432-436.

Flegal, K.M. et al., Prevalence of Obesity and Trends in the Distribution of Body Mass Index Among US Adults, 1999-2010. Journal of the American Medical Association. 2012; 307(5):491-97.

Fraser, I.S. et al., Depo-Provera use in an Australian metropolitan practice. Med J Australia 1994;160(9):553-6.

Hampton, R.M. et al., Bleeding patterns with monophasic and triphasic low-dose ethinyl estradiol combined oral aontraceptives. Contraception 2008;776):415-419.

Harel, Z. et al., Adolescents' Reasons for and Experience After Discontinuation of the Long-Acting Contraceptives Depo-Provera and Norplant. J Adolesc Health 1996;19(2):118-23.

Kaunitz, A.M., Injectable Depot Medroxyprogesterone Acetate Contraception: An Update for U.S. Clinicians. Int J Fertil Womens Med 1998;43(2):73-83.

Keder, L.M. et al., Compliance with depot medroxyprogesterone acetate: A randomized, controlled trial of intensive reminders. Am J Obstet Gynecol 1998;179(3 Pt 1):583-5.

Kirk, J.M. et al., Analysis of androgenic steroid Girard P hydrazones using multistage tandem mass spectrometry. Rapid Communication in Mass Spectrometry, 2006; 20:1247-1252.

Lidegaard, O. et al., Risk of venous thromboembolism from use of oral contraceptives containing different progestogens and oestrogen doses: Danish cohort study, Sep. 2001. BMJ 2011;343:d6423.

Mantha, S. et al., Assessing the risk of venous thromboembolic events in women taking progestin-only aontraception: a meta-analysis. BMJ 2012;345:e4944.

Murthy, A.S., Obesity and Contraception: Emerging Issues. Semin Reprod Med. Mar. 2010;28(2):156-63.

Nutley, T. et al., Treatment of bleeding problems associated with progestin-only contraceptives: survey results. Adv Contracept 1997;13(4):419-28.

OECD/European Union (2014), "Overweight and obesity among adults", in Health at a Glance: Europe 2014, OECD Publishing.

Pomp, E.R. et al., Risk of venous thrombosis: obesity and its joint effect with oral contraceptive use and prothrombotic mutations. Br J Haematol 2007;139:289-296.

Rosenbaum, P. et al., Inhibition of ovulation by a novel progestogen (drospirenone) alone or in combination with ethinylestradiol. 2000, The European Journal of Contraception and Reproductive Health Care, 5,16-24.

Rosenberg, M.J. et al., Unintended Pregnancies and Use, Misuse and Discontinuation of Oral Contraceptives. J Reprod. Med. 1995;40(5);355-360.

Rosenberg, M., Weight Change With Oral Contraceptive Use and During the Menstrual Cycle: Results of Daily Measurements. Contraception 1998;58:345-9.

Sedgh, G. et al., Inteded and Unintended Pregnancies Worldwide in 2012 and Recent Trends. Studies in Family Planning 2014; 45 (3):301-314.

Shigetoh, Y., et al., Higher Heart Rate May Predispose to Obesity and Diabetes Mellitus: 20-Year Prospective Study in a General Population. Am. J. Hypertension, vol. 22, No. 2, pp. 151-155, Feb. 2009.

United Nations, Department of Economic and Social Affairs, Population Division, World Contraceptive Patterns 2013.

World Health Organization, Medical eligibility criteria for contraceptive use. 4th ed. WHO Press, 2009.

* cited by examiner

PHARMACEUTICAL COMPOSITIONS COMPRISING ACTIVE DRUGS, CONTRACEPTIVE KITS COMPRISING ACTIVE DRUGS, AND METHODS OF ADMINISTERING THE SAME

CROSS-REFERENCE TO RELATED APPLICATIONS

This application is a continuation-in-part under 35 U.S.C. §120 to U.S. patent application Ser. No. 13/171,410, filed Jun. 28, 2011, which claims priority to U.S. Patent Application Ser. No. 61/368,396, filed Jul. 28, 2010. The entire contents of each of the foregoing applications is incorporated herein by reference.

FIELD OF THE INVENTION

The present invention relates to the field of contraceptive kits, pharmaceutical compositions and methods of administering and uses for the kits and pharmaceutical compositions.

BACKGROUND

Several contraceptives which comprise synthetic progestogens and no estrogen are commercially available. These contraceptives, called Progestogen-Only Contraceptives ("POCs"), encompass implants, uterine delivery systems and pills.

POCs have the advantage of avoiding the combined administration of estrogens as compared to traditional contraceptive combined pills. POCs, however, display several major drawbacks. Because of their low contraceptive reliability, POCs have to be taken each day at the same time without a pill-free or placebo interval.

The bleeding patterns for women who take POCs may be also be altered significantly as compared to the natural menstrual cycle, since amenorrhea or unscheduled bleeding or spotting may occur. Accordingly, POCs are seldom used and are usually only indicated for women who cannot tolerate estrogen, for women in post-partum period, and for women who are breast-feeding (Amy, Tripathi, 2009, BMJ, 339, 563-568; Mandisk, 2008, OBSTETRIC MEDICINE, 1, 78-87).

Drospirenone (CAS: 67392-87-4; 6b,7b:15b,16b-Dimethylen-3-oxo-17a-pregn-4-ene-21,17-carbolactone) is a synthetic progestogen with a pharmacological profile very closely related to that of natural progesterone. Drospirenone ("DRSP") is devoid of androgenic, glucocorticoid and antiglucocorticoid activity, but it does possess potent antimineralocorticoid and antiandrogenic properties. It has been shown that oral daily doses of at least 3 mg of drospirenone can inhibit ovulation over a single treatment cycle of 21 days. The combination of 3 mg drospirenone/30 µg ethinylestradiol may provide a reasonable contraceptive safety margin by inhibiting ovulation with a low frequency of follicular maturation (Rosenbaum et al., 2000, THE EUROPEAN JOURNAL OF CONTRACEPTION AND REPRODUCTIVE HEALTH CARE, 5, 16-24).

Drospirenone is thus an appropriate progestin ingredient which may avoid the side-effects occurring with conventional synthetic progestogens, such as weight gain and breast tenderness when combined with an estrogen for use as a contraceptive. DRSP is also likely to minimize fluid retention and to have neutral effects on metabolic and vascular risks (Blode et al., 2000, THE EUROPEAN JOURNAL OF CONTRACEPTION AND REPRODUCTIVE HEALTH CARE, 5, 256-264; Sitruk-Ware, 2006, HUMAN REPRODUCTION UPDATE, 12, 169-178). It has been also reported that drospirenone may treat moderate acne because of its well-established antiandrogenic properties.

Drospirenone as a contraceptive ingredient is available only in oral combined pills such as those marketed under the name of Yasmin® (3 mg DRSP/30 µg ethinylestradiol), Yaz® (3 mg DRSP/20 µg ethinylestradiol) and Yasminelle® (3 mg DRSP/20 µg ethinylestradiol). These pills comprise ethinylestradiol, which acts to increase the ovulation inhibitory effect of drospirenone and to ensure contraception and cycle stability. International Application WO2008/031631 provides combined oral contraceptives in which drospirenone is used as a progestative agent and ethinylestradiol is replaced by the phytoestrogen 8-prenylnaringenin. These contraceptives may be included in modified release formulations of 8-prenylnaringenin and drospirenone, which may continuously distribute the active ingredients for the gastrointestinal transit time of generally 12 h-16 h.

The commercially available contraceptives Yasmin®, Yaz® and Yasminelle® comprise drospirenone in a micronized form which promotes its rapid dissolution in vitro and ensures its good oral bioavailability. It is also the case for Angeliq®, which is a hormone replacement medicament combining drospirenone and estradiol. However, such formulations are characterized by a high plasma concentration peak for drospirenone after oral intake. High plasma concentrations are not desirable in patients treated with drospirenone because of a correlation between high $C_{max}$ and certain undesirable side effects as well as poor general tolerance when hormonal levels fluctuate too much each and every day.

While contraceptive use of drospirenone in combination with estrogen has been demonstrated to avoid many of the adverse side-effects, such as weight gain and irregular bleeding, contraceptive use of POCs, which are devoid of estrogen, has been associated with a number of undesirable side effects, including unscheduled bleeding or spotting, irregularities in the amount and frequency of menstrual flow, and weight gain.

Unscheduled bleeding or spotting has been observed in women using POCs. Scheduled bleeding or spotting occurs during hormone free intervals (days 25-28±1), whereas unscheduled bleeding or spotting may occur while taking the active hormones (days 2-23). Bleeding irregularities are one of the prominent reasons that patients discontinue contraception, which increases the risk of unintended pregnancy.

Irregularities in amount and frequency of menstrual flow and weight gain have also been reported as side effects of POC contraceptive use. Such side effects have been observed with DMPA, a long acting reversible progestin-only contraceptive birth control drug that is injected every 3 months (Harel Z et al. Adolescents' reasons for and experience after discontinuation of the long-acting contraceptives Depo-Provera and Norplant. J ADOLESC HEALTH 1996; 19:118-23; Kaunitz A M. Injectable depot medroxyprogesterone acetate contraception: an update for U.S. clinicians. INT J FERTIL WOMENS MED 1998; 43(2):73-83; Keder et al. Compliance with depot medroxyprogesterone acetate: a randomized, controlled trial of intensive reminders. AM J OBSTET GYNECOL 1998; 179(3 Pt 1)):583-5; Fraser & Dennerstein. Depo-Provera use in an Australian metropolitan practice. MED J AUSTRALIA 1994; 160:553-6.1-6; Nutley & Danson. Treatment of bleeding problems associated with progestin-only contraceptives: survey results. ADV CONTRACEPT 1997; 13:419-28; Hill. Gynecology case challenge:

vaginal bleeding in a woman taking an injectable contraceptive. MEDSCAPE WOMENS HEALTH 1998; 3(1):4).

POC treatment has also been associated with a weight gain. This is a particularly troubling for women with excess weight, i.e., women who are overweight or obese, since additional weight gain may increase their susceptibility to developing coronary heart diseases, high blood pressure, stroke, type 2 diabetes, abnormal blood fats, metabolic syndrome, cancer, osteoarthritis, sleep apnea, obesity hypoventilation syndrome, infertility, gallstones, gout, and other diseases or conditions associated with excess weight or obesity.

BRIEF SUMMARY

The embodiments described herein provide pharmaceutical compositions and kits comprising pharmaceutical compositions, and methods for administering pharmaceutical compositions for preventing pregnancy in a patient. The pharmaceutical compositions may comprise active drugs such as active contraceptive drugs. Specifically, the active drugs may comprise Progestogen-Only Contraceptives ("POCs") for inhibiting ovulation. In specific embodiments, the pharmaceutical compositions and kits and methods of administering the pharmaceutical compositions allow for novel dosing regimens of POCs and provide pharmacokinetic profiles that reflect these novel dosing regimens.

In one embodiment, the pharmaceutical composition may comprise an active contraceptive drug, wherein the pharmaceutical composition allows for a 28 day daily dosing regimen, and wherein after initial administration of the active contraceptive drug has established its contraceptive effect in a patient, the patient may skip up to 4 doses, including skipping 1, 2 and/or 3 doses, within any 28 day daily dosing regimen period. In one embodiment, the initial administration of the contraceptive drug sufficient to establish its contraceptive effect in a patient is at least a portion of a treatment cycle of 28 days, including at least 21 days, at least 22 days, at least 23 days, and/or at least 24 days. In a specific embodiment, the skipped up to 4 doses may be on non-consecutive days. In another specific embodiment, the skipped up to 4 doses may be on consecutive days. In another embodiment, the pharmaceutical composition may further allow during the 28 day daily dosing regimen for the patient to skip up to two non-consecutive days of the active contraceptive drug, provided the active contraceptive drug skipped dose is taken within about 24 hrs after the up to two skipped non-consecutive days. In another embodiment, the active contraceptive drug may inhibit ovulation. In another embodiment, the contraceptive effect may comprise inhibiting ovulation.

In accordance to one aspect of the embodiment, the active contraceptive drug may establish its contraceptive effect in a patient after at least a first, at least a second or at least a third 28 day daily dosing regimen is administered to the patient. The 28 day daily dosing regimen may include 21, 22, 23, 24, 25, 26, 27, or 28 active dosage units comprising an active contraceptive drug in a pharmaceutical composition which is administered to the patient daily. The 28 day daily dosing regimen may further comprise 7, 6, 5, 4, 3, 2, or 1 placebos, which one or more may be taken on the days of the 28 day daily dosing regimen on which the active dosage units are not administered to the patient.

In another specific embodiment, the active contraceptive drug may be a POC. In another specific embodiment, the POCs may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment, the POC may be drospirenone. In another specific embodiment, each daily dose of drospirenone may comprise a dosage amount of at least about 2 mg.

In another specific embodiment, the pharmaceutical compositions may also have a particular pharmacokinetic profile. In one embodiment, a pharmaceutical composition is provided wherein each daily dose of the active contraceptive drug, when orally administered to a patient in fasting conditions, provides a pharmacokinetic profile for the active contraceptive drug having:

i) a $T_{max}$ ranging from about 2.2 hrs to about 6 hrs; and
ii) a mean $C_{max}$ which is less than about 30 ng/ml.

In accordance with a first aspect of this embodiment, the pharmaceutical composition may be formulated as a single daily active dosage unit for administration to a patient having a BMI of about 25 kg/m² or more for at least a portion of a treatment cycle. In one embodiment, the pharmaceutical composition does not cause a number of days of bleeding events in the patient that exceeds an average of about 20%, about 15%, about 10%, about 8%, or about 5% per treatment cycle in consecutive treatment cycles of administration after an initial treatment cycle of administration.

In accordance with a second aspect of this embodiment, the pharmaceutical composition may be formulated as a single daily active dosage unit for administration to a patient having a BMI of about 30 kg/m² or more for at least a portion of a treatment cycle. In one embodiment, the pharmaceutical composition does not cause a number of days of bleeding events in the patient that exceeds an average of about 20%, about 15%, about 10%, about 8%, or about 5% per treatment cycle in consecutive treatment cycles of administration after an initial treatment cycle of administration.

In a specific embodiment, the pharmacokinetic profile for the active contraceptive drug may additionally comprise an $AUC_{0h\text{-}tlast}$ which is at least about 300 ng*h/ml. In another specific embodiment, the $AUC_{0h\text{-}tlast}$ may be at least about 350 ng*h/ml. In another specific embodiment, the mean $C_{max}$ may range from about 15 ng/ml to about 30 ng/ml. In another specific embodiment, the active contraceptive drug with the above pharmacokinetic parameters may be a POC. In another specific embodiment, the POC may be drospirenone. In another embodiment, drospirenone may be the sole active contraceptive drug in the pharmaceutical composition.

In another specific embodiment, a kit may comprise the pharmaceutical compositions described above. In a specific embodiment, the kit may comprise one or more packaging units wherein each packaging unit comprises up to 28 daily active dosage units comprising an active contraceptive drug in a pharmaceutical composition, wherein the pharmaceutical composition allows for a 28 day daily dosing regimen, and wherein after initial administration of the active drug has established its contraceptive effect in a patient, the patient may skip up to 4 doses within any 28 day daily dosing regimen period. In a specific embodiment, the skipped up to 4 doses may be on non-consecutive days. In another specific embodiment, the skipped up to 4 doses may be on consecutive days. In another embodiment, the kits may provide pharmaceutical compositions that further allow during the 28 day daily dosing regimen for the patient to skip up to two non-consecutive days of the active contraceptive drug, provided the active contraceptive drug skipped dose is taken within about 24 hrs after the up to two skipped non-consecutive days. In another embodiment, the active contraceptive drug may inhibit ovulation. In another embodiment, the contraceptive effect may comprise inhibiting ovulation.

The present embodiments also include methods of administering the pharmaceutical compositions described above. In one embodiment, the methods may comprise administering a composition comprising an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period. In a specific embodiment, the skipped up to 4 doses may be on non-consecutive days. In another specific embodiment, the skipped up to 4 doses may be on consecutive days. In another embodiment, the methods may comprise administering pharmaceutical compositions which further allows during the 28 day daily dosing regimen for the patient to skip up to two non-consecutive days of the active contraceptive drug, provided the active contraceptive drug skipped dose is taken within about 24 hrs after the up to two skipped non-consecutive days. In another specific embodiment, the kits may comprise pharmaceutical compositions comprising an active contraceptive drug with the above-described pharmacokinetic parameters. In another specific embodiment, the active contraceptive drug may be a POC. In another specific embodiment, the POC may be drospirenone. In another embodiment, drospirenone may be the only administered active contraceptive drug.

In another embodiment, the patient may have a higher risk for developing a complication from the administration of an estrogen than the general population. In a specific embodiment, the complication from the administration of an estrogen may be due to the patient having one or more conditions or characteristics selected from the group consisting of a higher risk for developing thromboembolism than the general population, acquired or genetic thrombophilia or hypercoaguability, an age of 35 years or over who smoke cigarettes, a higher risk for stroke than the general population, sickle-cell disease or sickle-cell anemia, a higher risk than the general population for myocardial infarction, and lactating women.

Many of these known health risks (e.g., thromboembolism, stroke, myocardial infarction) are associated with patients having excess weight (i.e., being overweight or obese).

The World Health Organization (WHO) provides a set of accepted weight standard status categories associated with BMI ranges for adults as follows:

BMI<18.5 kg/m$^2$ is indicative of an underweight status;
18.5 kg/m$^2$≤BMI≤24.9 kg/m$^2$ is indicative of a normal weight status;
25.0 kg/m$^2$≤BMI≤29.9 kg/m$^2$ is indicative of an overweight status; and
BMI≥30.0 kg/m$^2$ is indicative of an obese status.

Thus, in one embodiment, a patient may be considered to have excess weight if the patient presents with a BMI of about 25.0 kg/m$^2$ or more. A patient with excess weight encompasses overweight and obese patients. Thus, a patient may be deemed to be overweight if the patient presents with a BMI of about 25.0 kg/m$^2$ to about 29.9 kg/m$^2$ and a patient may be considered obese if the patient presents with a BMI of about 30 kg/m$^2$ or more.

Women having excess weight are medically counseled carefully regarding contraceptive treatment, since these women are subject to numerous risks associated with contraceptive treatment. Additionally, women with excess weight have an increased risk of pregnancy as compared to the women of normal weight while under contraceptive treatment, either with combined oral contraceptive pills (COCPs) or with progestogen-only pills (POCs). One reason for this is that women with excess weight are more likely to prematurely discontinue use of contraceptive treatment because they are more likely to suffer from one or more undesirable side effects of contraceptive treatment.

In another embodiment, the patient may be a woman and may have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non-steroidal anti-inflammatory, potassium-sparing diuretics, potassium supplementation medication, Angiotensin-converting enzyme (ACE) inhibitors, angiotensin-II receptor antagonists and heparin. In another specific embodiment, the patient may be in need to improve tolerance for drospirenone. In another specific embodiment, the patient may be preparing for Hormone Replacement Therapy medicaments.

In a further embodiment, the patient may have excess weight, which includes overweight and obese women. In one aspect, a patient may be characterized as overweight or obese based on the patient's Body Mass Index (BMI). BMI reflects a weight-to-height index that may be used to classify overweight and obesity in adults. It is defined as a person's weight in kilograms divided by the square of his or her height in meters (kg/m$^2$).

In another embodiment, the methods may comprise producing a pharmacokinetic profile of an active drug in a patient, wherein the pharmacokinetic profile comprises a mean $T_{max}$ ranging from about 2.2 hrs to about 6 hrs, and a mean $C_{max}$ which is less than about 30 ng/ml, wherein the pharmacokinetic profile is measured in said patient after orally administering a single daily dosage unit of said active drug to said patient in fasting conditions. In another specific embodiment, the pharmacokinetic profile may additionally comprise an $AUC_{0h-tlast}$ which is at least about 300 ng*h/ml. In another specific embodiment, the $AUC_{0h-tlast}$ may be at least about 350 ng*h/ml. In another specific embodiment, the active drug may be an active contraceptive drug. In another embodiment, the active contraceptive drug may inhibit ovulation. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another specific embodiment, the POC may be drospirenone. In another specific embodiment, drospirenone may be the only administered active drug.

In another embodiment, the methods may include administering to a patient the compositions provided above. In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non-steroidal anti-inflammatory, potassium-sparing diuretics, potassium supplementation medication, ACE inhibitors, angiotensin-II receptor antagonists and heparin. In another specific embodiment, the patient may be in need to improve tolerance for drospirenone. In another specific embodiment, the patient may be preparing for Hormone Replacement Therapy medicaments. In a further specific embodiment, the patient may have excess weight or may have a BMI of about 25.0 kg/m² or more. In yet a further embodiment, the patient may be overweight or may have a BMI of about 25.0 kg/m² to about 29.9 kg/m². In yet a further specific embodiment, the patient may be obese or may have a BMI of about 30.0 kg/m² or more.

In another embodiment, the pharmaceutical compositions may include active drugs that produce certain pharmacokinetic profiles. In a specific embodiment, the pharmaceutical composition may comprise an active drug, wherein a single daily dosage unit of the composition, when orally administered to a patient in fasting conditions provides a pharmacokinetic profile for the active drug having:

i) a $T_{max}$ ranging from about 2.2 hrs to about 6 hrs; and
ii) a mean $C_{max}$ which is less than about 30 ng/m.

In another specific embodiment, the pharmacokinetic profile may also include an $AUC_{0h-tlast}$ which is at least about 300 ng*h/ml. In another specific embodiment, the $AUC_{0h-tlast}$ may be at least about 350 ng*h/ml. In another specific embodiment, the active drug may be an active contraceptive drug. In another embodiment, the active contraceptive drug may inhibit ovulation. In another specific embodiment, the active contraceptive drug may be a POC. In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another specific embodiment, each daily dosage unit may comprise a dosage amount of at least about 2 mg.

In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non-steroidal anti-inflammatory, potassium-sparing diuretics, potassium supplementation medication, ACE inhibitors, angiotensin-II receptor antagonists and heparin. In another specific embodiment, the patient may be in need to improve tolerance for drospirenone. In another specific embodiment, the patient may be preparing for Hormone Replacement Therapy medicaments. In a further specific embodiment, the patient may have excess weight or may have a BMI of about 25.0 kg/m² or more. In yet a further embodiment, the patient may be overweight or may have a BMI of about 25.0 kg/m² to about 29.9 kg/m². In yet a further specific embodiment, the patient may be obese or may have a BMI of about 30.0 kg/m² or more.

In another embodiment, the pharmaceutical compositions may comprise active drugs characterized by dissolution tests. In a specific embodiment, a pharmaceutical composition may comprise an active drug, wherein:

(a) a daily active oral dosage unit of the composition comprises an amount of said active drug of at least about 2 mg, and
(b) the daily active oral dosage unit comprises the active drug in a form such that when subjected to an in vitro dissolution test according to the USP XXIII Paddle Method:
   (i) no more than about 50% of the active drug initially present in the daily active dosage unit is dissolved within 30 minutes, and
   (ii) at least about 50% of the active drug is dissolved in a time range from about 3 hours to about 4 hours.

In accordance with a first aspect of this embodiment, the pharmaceutical composition may be formulated as a single daily active dosage unit for administration to a patient having a BMI of about 25 kg/m² or more for at least a portion of a treatment cycle. In one embodiment, the pharmaceutical composition does not cause a number of days of bleeding events in the patient that exceeds an average of about 20%, about 15%, about 10%, about 8%, or about 5% per treatment cycle in consecutive treatment cycles of administration after an initial treatment cycle of administration.

In accordance with a second aspect of this embodiment, the pharmaceutical composition may be formulated as a single daily active dosage unit for administration to a patient having a BMI of about 30 kg/m² or more for at least a portion of a treatment cycle. In one embodiment, the pharmaceutical composition does not cause a number of days of bleeding events in the patient that exceeds an average of about 20%, about 15%, about 10%, about 8%, or about 5% per treatment cycle in consecutive treatment cycles of administration after an initial treatment cycle of administration.

In another specific embodiment, the active drug may be an active contraceptive drug. In another embodiment, the active contraceptive drug may inhibit ovulation. In another specific embodiment, the active contraceptive drug may be a POC. In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another embodiment, each daily dosage unit of drospirenone may comprise a dosage amount of at least about 2.0 mg to about 6.0 mg. In a specific embodiment, the each daily dosage unit of drospirenone may comprise a dosage amount of at least about 3.0 mg to about 4.5 mg.

The embodiments may also include kits that comprise one or more packaging units wherein each packaging unit comprises dosage units with an active drug that provides certain pharmacokinetic parameters. In a specific embodiment, the kit may comprise one or more packaging units wherein each packaging unit comprises 21 to 28 daily active dosage units comprising an active drug and wherein a single active dosage unit, when orally administered under fasting conditions, is adapted to provide a pharmacokinetic profile for the active drug consisting of one or more of the pharmacokinetic parameters selected from the group consisting of:
  i) a $T_{max}$ ranging from about 2.2 hrs to about 6 hrs; and
  ii) a mean $C_{max}$ which is less than about 30 ng/ml.

In another specific embodiment, the pharmacokinetic profile may also comprise an $AUC_{0h\text{-}tlast}$ which is at least 300 ng*h/ml. In another specific embodiment, the $AUC_{0h\text{-}tlast}$ may be at least 350 ng*h/ml. In another embodiment, the mean $C_{max}$ may range from about 15 ng/ml to about 30 ng/ml. In another specific embodiment, the active drug may be an active contraceptive drug. In another embodiment, the active contraceptive drug may inhibit ovulation. In another specific embodiment, the active contraceptive drug may be a POC In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone.

In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non-steroidal anti-inflammatory, potassium-sparing diuretics, potassium supplementation medication, ACE inhibitors, angiotensin-II receptor antagonists and heparin. In another specific embodiment, the patient may be in need to improve tolerance for drospirenone. In another specific embodiment, the patient may be preparing for Hormone Replacement Therapy medicaments. In a further specific embodiment, the patient may have excess weight or may have a BMI of about 25.0 kg/m² or more. In yet a further embodiment, the patient may be overweight or may have a BMI of about 25.0 kg/m² to about 29.9 kg/m². In yet a further specific embodiment, the patient may be obese or may have a BMI of about 30.0 kg/m² or more. In another specific embodiment, each daily dosage unit of drospirenone may comprise a dosage amount of at least about 2 mg. In another specific embodiment, the amount of drospirenone in each daily active unit dosage may range from about 2.0 mg to about 6.0 mg. In another specific embodiment, the amount of drospirenone in each daily active unit dosage may range from about 3.0 mg to about 4.5 mg.

The kits may also include contraceptive kits comprising one or more packaging units that comprise active dosage units comprising an active drug, such as drospirenone. In a specific embodiment, the contraceptive kit may comprise one or more packaging units wherein each packaging unit comprises 21 to 28 daily active dosage units and wherein
  (a) the amount of drospirenone in each daily active dosage unit is at least about 2 mg without estrogen, and
  (b) each daily active dosage unit comprises drospirenone in a form such that when subjected to an in vitro dissolution test according to the USP XXIII Paddle Method:
    (i) no more than about 50% of the drospirenone initially present in the daily active dosage unit is dissolved within 30 minutes and
    (ii) at least about 50% of the drospirenone is dissolved in a time range from about 3 hours to about 4 hours.

In a specific embodiment, drospirenone may be the sole contraceptive ingredient. In another specific embodiment, the amount of drospirenone in each daily active unit dosage may range from about 2.0 mg to about 6.0 mg. In another specific embodiment, the amount of drospirenone in each daily active unit dosage may range from about 3.0 mg to about 4.5 mg.

In one embodiment, pharmaceutical compositions may be provided comprising POC defined by a $d_{50}$ particle size. In a specific embodiment, the POC may have a $d_{50}$ particle size which ranges from about 10 μm to about 60 μm. In a specific embodiment, the $d_{50}$ particle size may range from about 10 μm to about 30 μm.

In another specific embodiment, the surface area of the particles may be from about 2,000 cm²/g to about 8,500 cm²/g. In another specific embodiment, the surface area of the particles may be from one or more selected from the group consisting of about 2,000 cm²/g, about 2,500 cm²/g, about 3,000 cm²/g, about 3,500 cm²/g, about 4,000 cm²/g, about 4,500 cm²/g, about 5,000 cm²/g, about 5,500 cm²/g, about 6,000 cm²/g, about 6,100 cm²/g, about 6,200 cm²/g, about 6,300 cm²/g, about 6,400 cm²/g, about 6,500 cm²/g, about 6,600 cm²/g, about 6,700 cm²/g, about 6,800 cm²/g, about 6,900 cm²/g, about 7,000 cm²/g, about 7,500 cm²/g, about 8,000 cm²/g and about 8,500 cm²/g.

In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another embodiment, the particles may have the pharmacokinetic profiles as characterized above.

In one embodiment, methods may comprise sizing drospirenone to a particular $d_{50}$ particle size. In a specific embodiment, the methods may comprise sizing drospirenone to a $d_{50}$ particle size which ranges from about 10 μm to about 60 μm by subjecting drospirenone to one or mills selected from the group consisting of a ball mill, a hammer mill, a fluid energy mill, a rod mill, a cutting mill and an oscillating granulator. In a specific embodiment, the methods may further comprise the step of subjecting drospirenone to a vibrating sieve. In another embodiment, the methods may comprise sizing drospirenone to a $d_{50}$ particle size which ranges from about 10 μm to about 60 μm by:

(i) dissolving drospirenone in a water-miscible solvent; and (ii) dispersing the resulting solution in cold water under stirring so that to induce the precipitation of drospirenone.

In another specific embodiment, the methods may further comprise the step of subjecting drospirenone to a vibrating sieve. In a specific embodiment, the water-miscible solvent may be selected from one or more of the group consisting of methanol, ethanol, isopropanol, dimethylformamide, tetrahydrofuran, dioxane or dimethyl sulfoxide, dimethylacetamide and acetone. In another specific embodiment, the water-miscible solvent may be dimethylacetamide.

In another embodiment, the pharmaceutical compositions may comprise a POC, wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment, the pharmaceutical compositions may comprise drospirenone, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

In another embodiment, the methods may include administering compositions that comprise a POC, wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment, the methods may include administering compositions that comprise drospirenone, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

In another embodiment, the kits may comprise one or more packaging units wherein each packaging unit comprises up to 28 daily active dosage units comprising a POC in a pharmaceutical composition, wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment, the kits may comprise one or more packaging units wherein each packaging unit comprises up to 28 daily active dosage units comprising drospirenone in a pharmaceutical composition, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

BRIEF DESCRIPTION OF THE DRAWINGS

FIG. 1 shows the cumulative distribution curve (cdf, filled diamonds) and the probability density function curve (pdf, filled squares) for drospirenone (DRSP) batch 080053. The distribution experimental data were obtained by laser diffraction method. X-coordinate: particle size (μm) in log scale. Left Y-coordinate: cumulative distribution in percentage. Right Y-coordinate: probability density function.

FIG. 2 shows the in vitro dissolution profiles for tablet (A-3 mg) obtained from DRSP batch 080053 as described in Example 1 (an embodiment of the invention, curve n° 2) and comparative tablets, namely Yasminelle® (curve n° 4), tablets CO1-3 mg (curve n° 3) and tablets CO2-3 mg (curve n° 1). Each tablet comprises 3 mg of DRSP. The in vitro dissolution profiles were determined by the USP XXIII Paddle Method as described in Example 2. X-coordinate: time in hours, Y-coordinate: mean dissolution percentage of DRSP relating to the initial amount of DRSP contained in the tested tablet.

FIG. 3A shows DRSP plasma mean concentration versus time curves obtained after the oral administration of a single tablet of reference product, i.e., Yasminelle® (empty squares) and after the oral administration of a single tablet obtained from DRSP batch 080053 as described in Example 1 (test product, filled squares). In both cases, the DRSP dosage was 3 mg. These clinical data were obtained during a monocentric, open, randomized, single-dose, two period crossover clinical trial conducted on 14 healthy female volunteers as described in Example 3 part 1. Each volunteer received randomly, an oral single dose of 1 tablet of the test product or one tablet of Yasminelle® on two single occasions, always under fasting conditions. Study periods were separated by a real wash-out phase of 7 days. In each study, blood samples were collected before the administration of the tablet (pre-dose, time 0) and at 0:30, 1:00, 1:30, 2:00, 3:00, 4:00, 5:00, 6:00, 8:00, 12:00, 24:00, 48:00 and 72:00 hours post dosing for assaying the DRSP plasma concentration. The X-coordinate: time after the oral administration of the tablet (in hours); and Y-coordinate: mean plasma concentration of DRSP in ng/ml (arithmetic mean).

FIG. 3B shows DRSP plasma mean concentration versus time curves obtained after the oral administration of a single tablet of reference product, i.e., Yasminelle® (empty squares) or after the oral administration of a single tablet CO1-3 mg (filled diamonds) or after the oral administration of a single tablet CO2-3 mg (filled squares) under fasting conditions (see Example 3, part 2). The X-coordinate: time after the oral administration of the tablet (in hours); the Y-coordinate: mean plasma concentration of DRSP in ng/ml (arithmetic mean).

FIGS. 4A and 4B show the experimental DRSP plasma mean concentration versus time curves: (i) for the oral administration of a single tablet of Yasminelle® (comparative, filled squares); and (ii) for the oral administration of a single tablet as described in Example 1 (A-3 mg, empty triangles). Both Yasminelle® tablet and tablet A-3 mg contains 3 mg of DRSP. FIGS. 4A and 4B also show the predicted mean DRSP plasma concentration versus time curve (empty diamonds) obtained for the oral administration of a tablet similar to that described in Example 1, but containing 4 mg of DRSP (tablet A-4 mg). Such a curve was extrapolated from the experimental pharmacokinetic data obtained in the clinical trial described in Example 3, part 1. The X-coordinate: time after the oral administration of the tablet (in hours); the Y-coordinate: mean plasma concentration of DRSP in ng/ml.

FIG. 4C shows the mean plasma DRSP concentration versus time curves resulting from the repeated administration of one tablet of Yasminelle® (curve n °1), that of one tablet A-3 mg (curve n °3), and that of one tablet A-4 mg (curve n °2), every 24 hours. These curves were obtained by extrapolation of experimental pharmacokinetic data obtained in the clinical trial described in Example 3. The X-coordinate: time after the oral administration of the first tablet (in hours); the Y-coordinate: mean plasma concentration of DRSP in ng/ml.

FIG. 5A shows the mean in vitro dissolution profile for tablets obtained from DRSP batch No PR100003 as described in Example 5 (see part 1). The tablet comprises 4 mg of DRSP. The X-coordinate: time in hours; the Y-coordinate: mean dissolution percentage of DRSP relating to the initial amount of DRSP contained in the tested tablet.

FIG. 5B shows DRSP plasma mean concentration versus time curves obtained after the oral administration of a single tablet of reference product, i.e., Yasminelle® (empty squares) or after the oral administration of a single tablet B-4 mg (filled squares) under fasting conditions (see Example 5, part 2). The X-coordinate: time after the oral administration of the tablet (in hours); the Y-coordinate: mean plasma concentration of DRSP in ng/ml.

FIGS. 6A and 6B show individual plasma levels of progesterone and estradiol in patients during treatment period and follow-up period. FIGS. 6A and 6B show the results of a clinical trial aiming to illustrate the contraceptive efficiency of the contraceptive compositions. The methodology of the clinical trial is described in Example 4. Briefly, the treatment period comprises two treatment cycles in which the subjects took one pill of 4 mg DRSP (tablet B-4 mg) from day 1 to day 24 and one placebo tablet from day 25 to day 28 of each treatment cycle at a fixed hour. On day 5 and day 13 of the second treatment cycle, the pill intake was delayed for 24 hours (i.e. no pill was taken on day 5 and day 13 and that 2 pills were taken on day 6 and day 14, respectively). The complete study consisted of a 56-day treatment period and a 28-day post-treatment follow-up period. The pill corresponds to tablet B-4 mg.

FIG. 6A shows the variation of the individual plasma levels of progesterone during the treatment period and the follow-up period. The X-coordinate: time in days after the first pill intake; the Y-coordinate: progesterone level in ng/ml.

FIG. 6B shows the variation of the individual plasma levels of estradiol during the treatment period and the follow-up period. The X-coordinate: time in days after the first pill intake; The Y-coordinate: estradiol level in pg/ml.

DETAILED DESCRIPTION OF THE EXEMPLARY EMBODIMENTS

Figure 1:
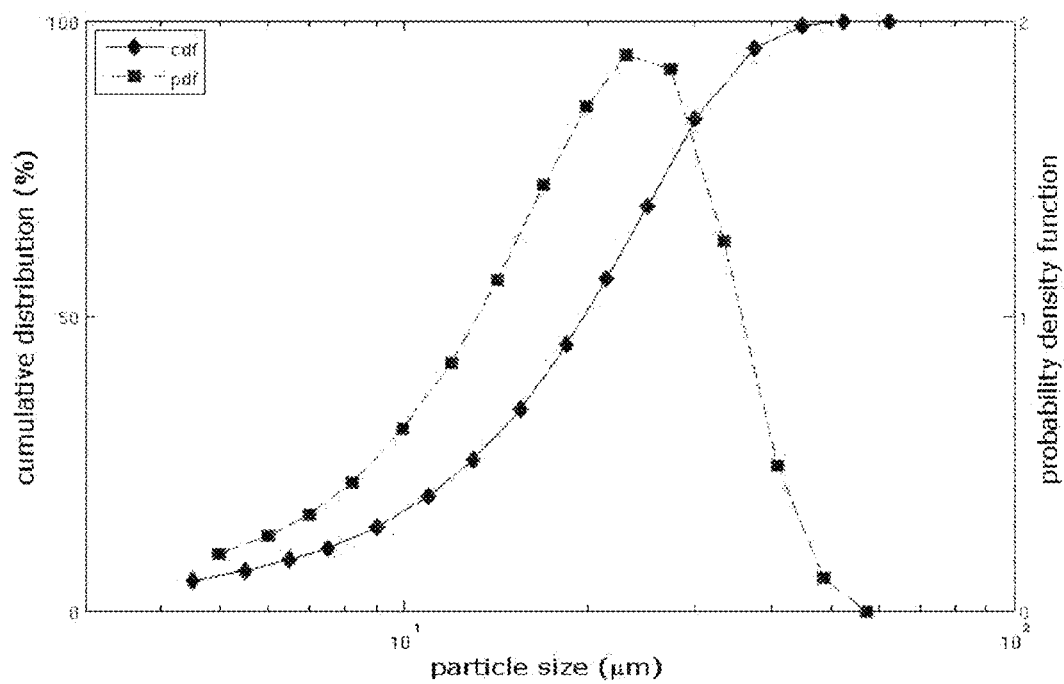
FIG. 1: Particle Size Distribution

The present invention relates to pharmaceutical compositions and contraceptive kits comprising a plurality of active daily dosage units. Each active daily dosage unit may include a pharmaceutical composition comprising an active drug. In a specific embodiment, each daily dosage unit may include a pharmaceutical composition comprising an active drug such as a POC. In another specific embodiment, each daily dosage unit may include a pharmaceutical composition comprising drospirenone. In certain embodiments, the pharmaceutical composition may include drospirenone, without estrogen. In other words, the contraceptive kit may comprises a POC kit. Drospirenone may be the sole contraceptive agent present within the pharmaceutical composition. The active daily dosage unit enables to prevent pregnancy when daily administered to a woman of child-bearing age over a period of 21 to 28 consecutive days. The number of active daily dosage units in the contraceptive kit may vary depending on the contraceptive method in which the contraceptive kit is intended to be used.

1. Pharmaceutical Compositions

The commercially available drospirenone-containing contraceptive pills comprise both ethinyl-estradiol and micronized drospirenone. According to European Patent EP1214076B1, the micronized form of drospirenone promotes its rapid dissolution in vitro. This rapid dissolution in vitro is claimed to be a necessary condition for obtaining a good bioavailability via the oral route. The rapid dissolution rate of drospirenone in vitro is assessed to be correlated to a rapid absorption in vivo of DRSP, which avoids its degradation by gastric or intestine environments. Several other patents and patent applications, such as International Applications WO2006128907, or WO2009138224, describe drospirenone compositions which exhibit a rapid dissolution of drospirenone in vitro.

Accordingly, International Application WO2006/128907 describes that surfactants may enhance the dissolution rate of non-micronized drospirenone having a specific surface area lower than 10,000 cm²/g. International Application WO2009/138224 describes that the dissolution rate of drospirenone may be significantly improved by co-milling drospirenone with an appropriate carrier so as to obtain drospirenone in an amorphous state.

As mentioned in EP1214076B1, a rapid dissolution of drospirenone in vitro generally means that at least 70% of the drospirenone is dissolved within 30 minutes when the composition is subjected to an in vitro dissolution assay such as USP XXIII Paddle Method II.

Surprisingly, the data demonstrated, through in vivo pharmacokinetic assays, that a rapid dissolution of drospirenone in vitro is not required for obtaining a good oral bioavailability. In this respect, the embodiments described herein provides a drospirenone-containing composition with a slow dissolution rate of drospirenone in vitro and which exhibits a similar mean AUC value (Area Under the Curve) as compared to Yasminelle® when orally administered to female patients.

Moreover, the embodiments disclosed herein provide DRSP-containing compositions which also display a significantly mean reduced $C_{max}$ value (Maximum Plasma Concentration) associated with a delayed mean $t_{max}$ value for drospirenone as compared to Yasminelle®. The decrease of DRSP $C_{max}$ improves the tolerance of the DRSP-containing composition by reducing or avoiding side-effects, in particular those related to the plasma level of potassium. Drospirenone has an anti-mineralocorticoid property which leads to an increase of potassium excretion and also, to an increase of potassium plasma level. It has been suggested that the $C_{max}$ of drospirenone correlates to the $C_{max}$ of potassium released after drospirenone administration. Such an increase of potassium plasma concentration after drospirenone administration may lead to hyperkalemia which is known to induce various disorders such as dizziness, palpitations, muscle weakness and even cardiac arrhythmia.

When orally administered, the DRSP-containing compositions according to the embodiments disclosed herein, induces a reduced plasma $C_{max}$ for drospirenone. A reduced $C_{max}$ for DRSP is expected to reduce the release of potassium in plasma. Consequently, in the case of the compositions, the tolerance for drospirenone may be improved especially for women who are predisposed to hyperkalemia, to women who suffer from kidney, liver or adrenal diseases, and for women who are on daily, long-term treatment for a chronic condition with medications predisposed to hyperkalemia. Medications predisposed to hyperkalemia include, without being limited to, non-steroidal anti-inflammatory drugs, potassium-sparing diuretics, potassium supplementation, ACE inhibitors, angiotensin-II receptor antagonists and heparin.

Consequently, the DRSP-containing compositions according to the embodiments may be particularly appropriate to prepare any oral medicament in which the mean $C_{max}$ value for DRSP should be controlled in order to improve the tolerance for drospirenone. For example, the compositions may be used for preparing Hormone Replacement Therapy medicaments ("HRT").

Since the DRSP-containing composition of the embodiments combine a reduced $C_{max}$ with a delayed $t_{max}$ and an $AUC_{0h-tlast}$ sufficient to provide a contraceptive effect, the compositions may be appropriate for use in progestogen-only pills. As illustrated in Example 5, part 3, the compositions provide an efficient and stable contraceptive drospirenone blood level when daily administered to a female patient. Thus, the co-administration of an estrogen to ensure contraception and cycle stability is not required. Since the mean $C_{max}$ value is significantly reduced, the contraceptive compositions may provide a more stable plasma concentration of drospirenone, i.e. a DRSP plasma concentration with low fluctuations between two consecutive administrations. Such a feature further reduces the incidence of unscheduled spotting and bleeding and, thus, significantly improves the bleeding profile as compared to conventional POCs.

As described in Example 5, the compositions continue to have a contraceptive effect even when a placebo period is introduced in the contraceptive regimen and some daily pills are missed. Accordingly, the compositions will exhibit a higher contraceptive reliability than other progestogen only pills, which will allow the patients to be less compliant with treatment without risking unwanted pregnancy.

Also the contraceptive compositions—which may not contain estrogen—will be as efficient as a combined oral pill without inducing the side effects related to estrogen, in particular, without increasing the risk of cardiovascular events. Thus, in some embodiments, the pharmaceutical compositions may be appropriate to be used as an oral contraceptive. In some other specific embodiments, the pharmaceutical composition may be used as a progestogen-only pill.

As used herein "Progestogen-Only Contraceptive", or "progestogen-only pill" (POC) means a pill or a contraceptive which comprises progestogens as sole contraceptive agents and does not comprise any estrogen.

By "composition having an improved pharmacokinetic profile for drospirenone" as used herein, is thus meant that the oral administration of a single daily dosage unit of said drospirenone-containing composition provides a pharmacokinetic profile for drospirenone characterized by a delayed mean $t_{max}$ and a reduced mean $C_{max}$ as compared to the administration of a single daily dosage unit of Yasminelle®. The pharmacokinetic profile of Yasminelle® is described in Example 3

In some embodiments, a pharmaceutical DRSP-containing composition is provided that, when orally administered as a single daily dosage unit of said composition, is adapted to provide a pharmacokinetic profile for DRSP having a mean $C_{max}$ which is less than about 85% of the mean $C_{max}$ obtained after the oral administration of a single dosage unit of Yasminelle®. The pharmaceutical DSRP-containing composition according to the present embodiments may further be characterized by, when orally administered, a single daily dosage unit of the composition is adapted to provide a pharmacokinetic profile for DRSP having a mean $t_{max}$ which is at least about 150% of the mean $t_{max}$ obtained after the oral administration of a single dosage unit of Yasminelle®.

Thus, the administration of a single dosage unit of the composition may provide a mean $AUC_{0h-tlast}$, which is sufficient to produce the pharmaceutical or the biological effect which is sought by the administration of drospirenone. In the present embodiments, the pharmaceutical or biological effect generally refers to a contraceptive effect.

When the compositions of the embodiments are used as a contraceptive, it may be further required that the mean $AUC_{0h-tlast}$ obtained upon the administration of a single daily dosage unit of said composition is at least about 70% of the mean $AUC_{0h-tlast}$ obtained in the case of Yasminelle®. In other words, in some embodiments, the daily dosage unit of the pharmaceutical composition may possess a combination of physical and/or chemical features such that, when orally administered, the daily dosage unit is adapted to provide a pharmacokinetic profile having the following characteristics:
  (i) a mean $C_{max}$ which is no more than about 85% of the mean $C_{max}$ obtained after the oral administration of a single dosage unit of Yasminelle® and
  (ii) a mean $t_{max}$ which is at least about 150% of the mean $t_{max}$ obtained after the oral administration of a single dosage unit of Yasminelle®, and, optionally, a mean $AUC_{0h-tlast}$ which is at least about 70% of the mean $AUC_{0h-tlast}$ obtained after the oral administration of a single dosage unit of Yasminelle®.

In some embodiments, the mean $AUC_{0h-tlast}$ may be at least about 85% of the mean $AUC_{0h-tlast}$ obtained after the oral administration of a single dosage unit of Yasminelle®. In some embodiments, the pharmaceutical compositions display one or more of the previous mentioned pharmacokinetic characteristics. The $AUC_{0h-tlast}$, the $C_{max}$ and the $t_{max}$ are determined based on the drospirenone plasma concentration versus time curve. For a given drospirenone-containing composition, the drospirenone plasma concentration versus time curve may be determined by following plasma drospirenone concentration over a period of about 72 h after a single oral intake of one daily dosage unit of the drospirenone-containing composition.

The single oral administration of the drospirenone-containing composition, in one embodiment, may be preferably performed in fasting conditions i.e. without food and not close to mealtime (in general, approximately 6 h-10 h after meal) since food ingestion may modify the absorption rate of drospirenone in the gastrointestinal tract.

The $C_{max}$ and $t_{max}$ values refer to the maximum DRSP plasma concentration and the time to reach it, respectively, after the oral administration of a single daily dosage unit of the DRSP-containing composition of interest. In other words, $C_{max}$ and $t_{max}$ refer to the characteristics of drospirenone plasma concentration peak observed after the oral intake of a single daily dosage unit of the composition of interest.

The $AUC_{0h-tlast}$ corresponds to the area obtained by integration of the drospirenone plasma concentration versus time over the interval [0h-tlast], the point "0h" referring to the oral intake of a single daily dosage unit of the composition of interest and the point "tlast" refers to the last time for which plasma concentration of DRSP can be quantifiable.

DRSP plasma concentration may be determined by well-known methods. For example, an appropriate method of quantification comprises the extraction of DRSP from human plasma and then its quantification using liquid chromatography coupled with tandem mass spectrometry.

In an embodiment, one skilled in the art may adapt the analytical method described by Kirk et al (Rapid Communication in Mass Spectrometry, 2006; 20:1247-1252). Such a method comprises a step of derivatization of drospirenone with Girard P hydrazine solution in order to increase the response of DRSP during the subsequent MS analysis. This method is generally appropriate to quantify DRSP in human EDTA plasma over a concentration range from about 0.25 ng/ml to about 100 ng/ml.

As used herein, the mean $AUC_{0h-tlast}$, the mean $C_{max}$ and the mean $t_{max}$ refer to arithmetic mean values determined from individual pharmacokinetic data obtained for a group of healthy female volunteers of child bearing age subjected to a single oral administration of one daily dosage unit of a drospirenone-containing composition. The group of healthy female volunteers may comprise enough women to provide statistically confident pharmacokinetic results. Preferably, the group comprises at least ten healthy women of childbearing age.

As used herein, a healthy woman of child-bearing age refers to a pre-menopause Caucasian female between 18 and 40 years, with a BMI ranging from about 18 to 29 kg/m² and with no health problem, in particular, with no metabolism, renal, liver or gynecologic disorders.

Preferably, such volunteers have not taken any hormone-containing compositions within 3 months prior to the trial to determine the pharmacokinetic parameters of interest.

For example, all endpoints listed above may be determined in a model-independent way. The highest concentration actually measured and the time at which it was registered after each dose in any given volunteer may be regarded as $C_{max}$ and $t_{max}$ respectively according to the algorithm of the program NC_PKP.sas.

The daily dosage unit of the DRSP containing-composition may comprise at least about 2 mg of drospirenone. A daily amount of DRSP from about 3 mg to about 4.5 mg may be desired when the composition is used as contraceptive.

As used herein, Yasminelle® is a combined oral pill commercialized by Bayer/Schering. The daily dosage unit of Yasminelle® is a coated tablet which comprises 3 mg of micronized drospirenone and ethinylestradiol betadex clathrate in an amount corresponding to 20 μg of ethinylestradiol. The tablet further comprises lactose monohydrate, maize starch and magnesium stearate as main excipients. The coating of the tablet comprises hypromellose, talc, titane oxide and iron oxide red.

As used herein, Yasminelle® (marketed under the name of Jasminelle® in France) refers to the pharmaceutical product covered by the French Marketing Authorization related to CIS number (Code d'Identification de Spécialité) 65052799 and revised on Sep. 17, 2009.

In an embodiment, the pharmacokinetic parameters (namely $C_{max}$, $t_{max}$ and $AUC_{0h\text{-}tlast}$) are determined after the first oral administration of a single unit dosage of the DRSP-containing composition of interest, said first oral administration occurring in fasting conditions.

In a more general aspect, the embodiments disclosed herein may provide a pharmaceutical composition comprising an active drug, when orally administered as a single daily dosage unit of said composition, is adapted to provide a pharmacokinetic profile for said active drug having a mean $C_{max}$ which is less than about 30 ng/ml. The pharmaceutical composition comprising an active drug may be further characterized in that, when orally administered, a single daily dosage unit of said composition is adapted to provide a pharmacokinetic profile for said active drug having a mean $t_{max}$, which is at least about 2.2 h.

In another embodiment, the mean $AUC_{0h\text{-}tlast}$ obtained upon the administration of a single daily dosage unit of said composition may be at least about 300 ng*ml/h. The daily dosage unit of the pharmaceutical composition may possesses a combination of physical and/or chemical features such that, when orally administered, the daily dosage unit is adapted to provide a pharmacokinetic profile having the following characteristics:
  (i) a mean $C_{max}$ which is less than about 30 ng/ml
  (ii) a mean $t_{max}$ of at least about 2.2 h; and, optionally,
  (iii) a mean $AUC_{0h\text{-}tlast}$ of at least about 300 ng*h/ml.

In another specific embodiment, the $t_{max}$ may range from about 2.2 hrs to about 6 hrs. In another specific embodiment, said $AUC_{0h\text{-}tlast}$ may be at least 350 ng*h/ml.

In another embodiment, the active drug, when orally administered and provides such a pharmacokinetic profile, may be a drug that inhibits ovulation. In a specific embodiment, the active drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment, the POC may be drospirenone.

In a specific embodiment, the embodiments may provide a pharmaceutical DRSP-containing composition, when orally administered as a single daily dosage unit of said composition, is adapted to provide a pharmacokinetic profile for DRSP having a mean $C_{max}$ which is less than about 30 ng/ml. The pharmaceutical DRSP-containing compositions may be further characterized in that, when orally administered, a single daily dosage unit of said composition is adapted to provide a pharmacokinetic profile for DRSP having a mean $t_{max}$, which is at least about 2.2 h.

The administration of a single dosage unit of the composition including DRSP may provide a mean $AUC_{0h\text{-}tlast}$, which is sufficient to produce the pharmaceutical or the biological effect which is sought by the administration of drospirenone. Accordingly, when the compositions are used as a contraceptive, it may be further required that the mean $AUC_{0h\text{-}tlast}$ obtained upon the administration of a single daily dosage unit of said composition is at least about 300 ng*ml/h. In other words, in some embodiments, the daily dosage unit of the pharmaceutical composition may possess a combination of physical and/or chemical features such that, when orally administered, the daily dosage unit is adapted to provide a pharmacokinetic profile having the following characteristics:
  (i) a mean $C_{max}$ which is less than about 30 ng/ml
  (ii) a mean $t_{max}$ of at least about 2.2 h
  and, optionally, a mean $AUC_{0h\text{-}tlast}$ of at least about 300 ng*h/ml.

In some embodiments, the pharmaceutical composition may display all the previous mentioned pharmacokinetic characteristics.

As used herein, the term "about" before a "specific value" defines a range from "the specific value minus at least 10% of the specific value" to "the specific value plus at least 10% of the specific value". For example, "about 50" defines a range from 45 or less to 55 or more. In addition, it may define a range where "the specific value minus at least 20% of the specific value" to "the specific value plus at least 20% of the specific value" Further, it may define a range where "the specific value minus at least 30% of the specific value" to "the specific value plus at least 30% of the specific value" and so on.

A mean $AUC_{0h\text{-}tlast}$ of at least about 300 ng*h/mL includes a mean $AUC_{0h\text{-}tlast}$ of at least about 310 ng*h/mL, at least about 320 ng*h/mL, at least about 330 ng*h/mL, at least about 340 ng*h/mL, at least about 350 ng*h/mL, at least about 360 ng*h/mL, at least about 370 ng*h/mL, at least about 380 ng*h/mL, at least about 390 ng*h/mL, at least about 400 ng*h/mL, at least about 410 ng*h/mL at least about 420 ng*h/mL, at least about 430 ng*h/mL. In some embodiments, the mean $AUC_{0h\text{-}tlast}$ is at least about 350 ng*h/ml.

A mean $t_{max}$ of at least about 2.2 h includes a mean $t_{max}$ of at least about 2.5 h, of at least about 3.0 h, of at least about 3.5 h, of at least about 4 h. In a specific embodiment, the mean $t_{max}$ does not exceed about 6 hours in order to not significantly impair the bioavailability of DRSP. Thus, the mean $t_{max}$ preferably may range from about 2.2 h to about 6 h. In some embodiments, a $t_{max}$ ranges from about 3.0 h to about 4.0 h.

A mean $C_{max}$ which is less than about 30 ng/ml includes a $C_{max}$ less than about 28 ng/ml, less than about 26 ng/ml, less than about 24 ng/ml, less than about 22 ng/ml, less than about 20 ng/ml, less than about 19 ng/ml, less than about 18 ng/ml, less than about 17 ng/ml, less than about 16 ng/ml, less than about 15 ng/ml, less than about 14 ng/ml. In some embodiments, the mean $C_{max}$ ranges from about 15 ng/ml to about 30 ng/ml. In other embodiments, the mean $C_{max}$ ranges from about 15 ng/ml to about 26 ng/ml.

In certain embodiments, the daily dosage unit of the pharmaceutical composition may be adapted to provide a pharmacokinetic profile having the following characteristics:
  (i) a mean $C_{max}$ ranges from about 15 ng/ml to about 30 ng/ml,
  (ii) a mean $t_{max}$ ranges from 2.2 h to 6 h, and
  (iii) optionally, a mean $AUC_{0h-tlast}$ of at least about 300 ng*h/ml,
when the daily dosage unit is administered under fasting condition.

In a specific embodiment, the pharmacokinetic parameters (namely $C_{max}$, $t_{max}$ and $AUC_{0h-tlast}$) may be determined after the first oral administration of a single unit dosage of the active drug, said first oral administration occurring in fasting conditions.

In one embodiment, pharmaceutical compositions may comprise an active drug, wherein a single daily dosage unit of the composition, when orally administered to a patient in fasting conditions provides a pharmacokinetic profile for the active drug having:
  i) a $T_{max}$ ranging from about 2.2 hrs to about 6 hrs; and
  ii) a mean $C_{max}$ which is less than about 30 ng/ml.

In some embodiments, the oral administration of the active drug provides a pharmacokinetic profile that may further be characterized by a mean $AUC_{0h-tlast}$ of at least about 300 ng*ml/h, more preferably of at least about 350 ng*ml/h. In another specific embodiment, the mean $t_{max}$ may range from about 2.2 hrs to about 6 hrs. In another embodiment, the $C_{max}$ may range from about 15 ng/ml to about 30 ng/ml.

In another specific embodiment, the active drug may be an active contraceptive drug. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In one specific embodiment, the POC may be drospirenone.

The pharmaceutical composition is particularly appropriate to be used as a contraceptive, in particular, as a POC. The pharmaceutical compositions may also be used for preparing any other medicaments for which the improvement of the DRSP tolerance may be sought. Such medicaments include, without being limiting to, HRT medicament.

Without wishing to be bound by any theory, the embodiments disclosed herein show that the in vitro dissolution rate of drospirenone is correlated to its pharmacokinetic profile in vivo. A composition displaying a pharmacokinetic profile for drospirenone as fully-described above may exhibit a slow in vitro dissolution rate of drospirenone such that no more than about 50% of drospirenone initially present in the composition is dissolved within 30 minutes.

In one aspect, pharmaceutical compositions are provided which comprise drospirenone that is characterized by a slow dissolution rate of drospirenone in vitro. As used herein, by "a slow dissolution rate of drospirenone in vitro" is meant that the release of drospirenone is such that no more than about 50% of drospirenone initially present in the composition is dissolved within 30 minutes when the composition is subjected to a dissolution test.

As intended herein, no more than about 50% of the drospirenone encompasses no more than about 45%, about 40%, about 35%, about 30%, about 25%, about 20%, about 15%, about 10% of the drospirenone initially present in the contraceptive composition. In some embodiments, no more than about 40% of the drospirenone initially present in the composition is dissolved within 30 min.

As used herein, the percentage of drospirenone is related to the amount of drospirenone initially present in the contraceptive composition.

The in vitro dissolution rate of any active drug, including drospirenone, may be assessed by anyone of well-known methods described in the prior art. The in vitro dissolution rate of drospirenone is preferably assessed by the USP XXIII Paddle Method. Briefly, a tablet consisting of the contraceptive composition comprising drospirenone to be tested is placed in 900 mL of water at 37° C. (±0.5° C.). The dissolution test is performed using a USP dissolution test apparatus 2 at a stirring rate of 50 rpm. Given the desired in vitro dissolution rate of a contraceptive agent, such as drospirenone according to the USP XXIII Paddle Method, one skilled in the art can formulate a composition comprising the contraceptive agent and one or more pharmaceutically-acceptable carriers. Examples of such carriers are well known in the art and are disclosed in, for example, Remington: THE SCIENCE AND PRACTICE OF PHARMACY (21st ed. 2005).

The term "active drug" may include any compound intended to furnish pharmacological activity or other direct effect in the diagnosis, cure, mitigation, treatment and/or prevention of a condition. See 21 C.F.R. 210.3(b)(7). Further, "active drugs" include those compounds of the composition that may undergo chemical change during the manufacture of the composition and be present in the final composition in a modified form intended to furnish an activity or effect. Id. As used herein, an "active contraceptive drug" thus means an active drug that may prevent pregnancy when administered in an effective amount to a female patient through its contraceptive effect. The active contraceptive drug may prevent pregnancy to occur by various contraceptive effects. For example, the contraceptive effect may include, but is not limited to, one or more of the inhibition of ovulation, thickening of cervical mucus (which reduces the sperm viability and penetration) and/or preventing or otherwise impeding embryo implantation.

The term "drospirenone" or "DRSP" includes drospirenone itself, i.e. the chemical entity identified by the CAS registry Number 67392-87-4, solvates of drospirenone, and derivatives or prodrugs of drospirenone.

Drospirenone may be prepared by well-known methods described in the prior art, for example, described in U.S. Pat. No. 4,129,564, WO 1998/06738, EP11746101 or WO 2006/061309. The method described in WO 2006/061309 may be particularly suitable for preparing drospirenone. The method for preparing drospirenone may be performed so as to meet the Good Manufacturing Practice (GMP) requirements.

To ensure a good bioavailability of the active drug, a significant amount of the active drug initially comprised in the contraceptive composition has to be released in a reasonable time range. An in vitro dissolution rate of said active drug may be such that at least about 50% of the active drug initially present in the compositions was dissolved in a time range from about 3 hours to about 4 hours. In a specific embodiment, the active drug may be a POC. In another embodiment, the POC may be drospirenone. Indeed, the Applicant showed that a good bioavailability of drospirenone was achieved in the case of compositions comprising drospirenone which had an in vitro dissolution rate of drospirenone such that at least about 50% of the drospirenone initially present in the compositions was dissolved in a time range from about 3 hours to about 4 hours.

Accordingly, described herein are contraceptive compositions comprising drospirenone wherein the in vitro dissolution rate of the drospirenone is such that no more than about 50% of the drospirenone is dissolved within 30 minutes and such that at least about 50% of the drospirenone is dissolved in a time range from 3 hours to 4 hours.

A time range from about 3 hours to about 4 hours may include, in specific non-limiting embodiments, a time range from 3.25 hours, to 3.5 hours, and from 3.75 hours, to 4 hours.

At least about 50% of the active drug such as drospirenone encompasses at least about 50%, about 55%, about 60%, about 65%, about 70%, about 75%, about 80%, about 85%, at least about 88%, at least about 90%, at least about 91%, at least about 92%, at least about 93%, at least about 94%, at least about 95%, at least about 96%, at least about 97%, at least about 98%, at least about 99%, and at least about 99.5%.

In some embodiments, at least about 60% of the active drug, such as DRSP, initially present is dissolved in a time range from about 3 hours to about 4 hours. In some other embodiments, the contraceptive composition is further characterized in that at least about 70% of the active drug, such as drospirenone is dissolved within about 6 hours.

The applicant has shown that specific surface area of DRSP has a direct impact on the in vitro dissolution rate of drospirenone and its in vivo pharmacokinetic profile.

One way to obtain the active drug-containing compositions may be to use the active drug in a particle form having an appropriate specific surface area. Active drugs may be present in the pharmaceutical compositions in a non-micronized particle form. In a specific embodiment, the active drug may be a POC. For example, it has been also shown that the active drug drospirenone in a particle form having a specific surface area from about 2000 cm$^2$/g to about 8500 cm$^2$/g may be suitable for obtaining the contraceptive compositions. The specific surface area may be experimentally determined using the BET method (gas adsorption method).

In some embodiments, the contraceptive compositions may comprise active drugs such as drospirenone in a particle form having a specific area from about 2000 cm$^2$/g to about 8500 cm$^2$/g. Such a specific area range which includes values of about 2000 cm$^2$/g, about 2500 cm$^2$/g, about 3000 cm$^2$/g, about 3500 cm$^2$/g, about 4000 cm$^2$/g, about 4500 cm$^2$/g, about 5000 cm$^2$/g, about 5500 cm$^2$/g, about 6000 cm$^2$/g, about 6100 cm$^2$/g, about 6200 cm$^2$/g, about 6300 cm$^2$/g, about 6400 cm$^2$/g, about 6500 cm$^2$/g, about 6600 cm$^2$/g, about 6700 cm$^2$/g, about 6800 cm$^2$/g, about 6900 cm$^2$/g, about 7000 cm$^2$/g, about 7500 cm$^2$/g, about 8000 cm$^2$/g and about 8500 cm$^2$/g.

In a specific embodiment, concerning the size particle distribution, active drugs particles having a diameter greater than about 200 µm are preferably avoided. In a specific embodiment, drospirenone particles having a diameter greater than about 200 µm are preferably avoided in order to not drastically impair the in vitro dissolution rate and, thus, the in vivo bioavailability since such particles are poorly soluble. In a specific embodiment, drospirenone may preferably have a $d_{50}$ of less than about 70 µm. In an embodiment, the $d_{50}$ of the drospirenone particles may range from about 10 µm to about 60 µm. A $d_{50}$ ranges from about 10 µm to about 60 µm encompasses a $d_{50}$ of about 10 µm, of about 15 µm, of about 20 µm, of about 25 µm, of about 30 µm, of about 35 µm, of about 40 µm, of about 45 µm, of about 50 µm, of about 55 µm and of about 60 µm.

In some embodiments, the particle size distribution of the active drug present in the composition may be characterized by:
(i) a $d_{90}$ particle size less than about 100 µm, and/or
(ii) a $d_{50}$ particle size ranging from about 10 µm to about 60 µm and/or
(iii) a $d_{10}$ particle size more than about 3 µm.

In accordance with a first aspect of this embodiment, the pharmaceutical composition may be formulated as a single daily active dosage unit of a contraceptive agent for administration to a patient having a BMI of about 25 kg/m$^2$ or more for at least a portion of a treatment cycle. In one embodiment, the pharmaceutical composition does not cause an average number of days of bleeding events per treatment cycle in the patient that exceeds about 20%, of about 19%, of about 18%, of about 17%, of about 16%, of about 15%, of about 14%, of about 13%, of about 12%, of about 11%, of about 10%, of about 9%, of about 8%, of about 7%, of about 6%, of about 5%, of about 4%, of about 3%, of about 2% of about 1% over consecutive treatment cycles of administration after an initial treatment cycle of administration. The consecutive treatment cycles of administration after the initial treatment cycle of administration may be from a first through thirtieth treatment cycles after the initial treatment cycle of administration. Thus, in an example in which the treatment cycle is 28 days and in which the pharmaceutical composition does not cause a number of days of bleeding events in the patient that exceeds an average of about 15% per treatment cycle in consecutive treatment cycles of administration after the initial treatment cycle of administration, the number of days of bleeding events in the treatment cycle will not exceed about 24 days.

As used herein "a first through a thirtieth" or "a first to a thirtieth" includes any one of a first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, and thirtieth as the lower limit and any one of a first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, and thirtieth as the upper limit.

In accordance with a second aspect of this embodiment, the pharmaceutical composition may be formulated as a single daily active dosage unit of a contraceptive agent for administration to a patient having a BMI of about 30 kg/m$^2$ or more for at least a portion of a treatment cycle. In one embodiment, the pharmaceutical composition does not cause an average number of days of bleeding events per treatment cycle in the patient that exceeds about 20%, of about 19%, of about 18%, of about 17%, of about 16%, of about 15%, of about 14%, of about 13%, of about 12%, of about 11%, of about 10%, of about 9%, of about 8%, of about 7%, of about 6%, of about 5%, of about 4%, of about 3%, of about 2% of about 1% over consecutive treatment cycles of administration after an initial treatment cycle of administration. The consecutive treatment cycles of administration after the initial treatment cycle of administration may be from a first through thirtieth treatment cycles after the initial treatment cycle of administration. Thus, in an example in which the treatment cycle is 28 days and in which the pharmaceutical composition does not cause a number of days of bleeding events in the patient that exceeds an average of about 15% per treatment cycle in consecutive treatment cycles of administration after the initial treatment cycle of administration, the number of days of bleeding events in the treatment cycle will not exceed about 24 days.

In some other embodiments, the $d_{50}$ of the active drug particles may range from about 10 μm to about 30 μm. In a specific embodiment, the active drug may be a POC. In such embodiments, the particle size distribution of the POC present in the composition may be characterized by at least one of the following characteristics:
  (i) a $d_{90}$ particle size less than about 100 μm,
  (ii) a $d_{50}$ particle size ranging from about 10 μm to about 30 μm and
  (iii) a $d_{10}$ particle size more than about 3 μm.

In a specific embodiment, the particle size distribution of, drospirenone present in the composition may be characterized by:
  (i) a $d_{90}$ particle size less than about 100 μm, and/or
  (ii) a $d_{50}$ particle size ranging from about 10 μm to about 60 μm and/or
  (iii) a $d_{10}$ particle size more than about 3 μm.

In other specific embodiments, the $d_{50}$ of drospirenone particles may range from about 10 μm to about 30 μm. In such embodiments, the particle size distribution of the drospirenone present in the composition is characterized by at least one of the following characteristics:
  (i) a $d_{90}$ particle size less than about 100 μm,
  (ii) a $d_{50}$ particle size ranging from about 10 μm to about 30 μm and
  (iii) a $d_{10}$ particle size more than about 3 μm.

As used herein, the term "about" before a "specific value" defines a range from "the specific value minus 10% of the specific value" to "the specific value plus 10% of the specific value". For example, "about 50" defines a range from 45 to 55. In addition, it may define a range where "the specific value minus at least 20% of the specific value" to "the specific value plus at least 20% of the specific value." Further, it may define a range where "the specific value minus at least 30% of the specific value" to "the specific value plus at least 30% of the specific value" and so on.

As used herein, by "$d_{90}$ particle size" is meant that the particle size distribution is such that at least 90% of the particles have a particle size diameter of less than the specified value.

As used herein, by "$d_{50}$ particle size" is meant that the particle size distribution is such that at least 50% of the particles have a particle size diameter of less than the specified value.

As used herein, by "$d_{10}$ particle size" is meant that the particle size distribution is such that at least 10% of the particles have a particle size diameter of less than the specified value.

$d_{90}$ particle size less than about 100 μm may include $d_{90}$ particle sizes less than about 90 μm, about 80 μm, about 70 μm, about 60 μm, about 55 μm, about 50 μm, about 45 μm, about 40 μm, about 38 μm, about 36 μm, about 34 μm, about 32 μm, about 30 μm, about 28 μm, about 26 μm, about 24 μm, about 22 μm, and about 20 μm.

$d_{50}$ particle size values ranging from about 10 μm to about 30 μm may include values of about 10 μm, about 11 μm, about 12 μm, about 13 μm, about 14 μm, about 15 μm, about 16 μm, about 18 μm, about 19 μm, about 20 μm, about 21 μm, about 22 μm, about 23 μm, about 24 μm, about 25 μm, about 26 μm, about 27 μm, about 28 μm, about 29 μm, and about 30 μm.

$d_{10}$ particle size values more than about 3 μm may include $d_{10}$ particle size values more than about 3 μm, about 3.5 μm about 4.5 μm, about 5 μm, about 6 μm, about 7 μm, about 8 μm, about 9 μm, about 10 μm, about 11 μm, and about 12 μm. It goes without saying that $d_{10}$ particle size value is smaller than $d_{50}$ particle size value, which is smaller than $d_{90}$ particle value.

The active drug (such as drospirenone) particle size distribution, in particular $d_{90}$, $d_{10}$ and $d_{50}$ values, may be determined by well-known methods of the prior art such as sieve analysis, laser diffraction methods, photoanalysis or optical counting methods. Laser diffraction methods are particularly desirable. As illustrated in the Example 1, the particle size distribution may be determined by laser diffraction in wet dispersion. The dispersant is preferably water.

In some embodiments, the pharmaceutical composition may comprise drospirenone in a particle form having a particle size distribution having a combination of two characteristics selected from:
  (i) a $d_{90}$ particle size less than about 100 μm,
  (ii) a $d_{50}$ particle size ranging from about 10 μm to about 30 μm and
  (iii) a $d_{10}$ particle size more than about 3 μm.

In other words, the particle size distribution of DRSP display a combination of characteristics selected from characteristic (i) and characteristic (ii), characteristic (i) and characteristic (iii), and, characteristic (ii) and characteristic (iii).

In some other embodiments, the pharmaceutical composition is provided comprising drospirenone in a non-micronized form having a particle size distribution characterized in that:
  (i) $d_{90}$ particle size is less than about 100 μm,
  (ii) $d_{50}$ particle size ranging from about 10 μm to about 30 μm and
  (iii) $d_{10}$ particle size is more than about 3 μm In an embodiment, the DRSP particle distribution may be further characterized in that the $d_{90}$ particle size value is less than about 50 μm and in that no particle has a size greater than about 80 μm.

In some embodiments, the contraceptive composition may comprise drospirenone in a particle form having a $d_{90}$ particle size which ranges from about 20 μm to about 40 μm, a $d_{50}$ particle size which ranges from about 10 μm to about 30 μm and a $d_{10}$ which ranges from about 3 μm to about 9 μm and wherein no particle has a size greater than about 80 μm, more preferably no particle has a size greater than about 60 μm.

In some other embodiments, the contraceptive composition may comprise drospirenone in a particle form having:
  (i) a $d_{90}$ particle size which ranges from about 30 μm to about 40 μm,
  (ii) a $d_{50}$ particle size which ranges from about 15 μm to about 25 μm and
  (iii) a $d_{10}$ which ranges from about 5 μm to about 9 μm and wherein no particle has a size greater than about 80 μm, more preferably no particle has a size greater than about 60 μm.

For illustrative purposes, an appropriate particle size distribution of drospirenone is shown in FIG. 1.

In some other embodiments, the contraceptive composition may comprise drospirenone in a particle form having a specific surface area from about 2000 cm²/g to about 8000 cm²/g and having a $d_{50}$ particle size ranges from about 10 µm to about 60 µm.

To obtain drospirenone in a particle form having the specific surface area and/or the particle size distribution as described above, one skilled in the art may use well-known methods of the prior art such as a milling process optionally combined with a sieve process. For example, drospirenone, obtained by anyone of the synthesis methods described in the prior art, may be subjected to a ball mill or hammer mill step, optionally followed by vibrating sieve steps. The subsequent vibrating sieve steps may remove the finest and biggest particles of drospirenone which would impair the pharmacokinetic profile and the in vitro dissolution profile of drospirenone.

One skilled in the art may adjust the parameters of the milling and sieve steps by routine experiments to obtain the appropriate particle form of drospirenone. Appropriate mills that may be used include a fluid energy mill, a ball mill or rod mill, a hammer mill, a cutting mill and an oscillating granulator.

An appropriate particle form of a POC, such as drospirenone, may also be prepared by a crystallization or precipitation process optionally combined with a sieve step in order to fully control the size of POC/drospirenone particles. For example, the precipitation process may comprise the steps of (i) dissolving drospirenone in a water-miscible solvent and then (ii) dispersing the resulting solution in cold water under stirring so that to induce the precipitation of drospirenone. The drospirenone particles may be then recovered by a filtration process.

The water-miscible solvents may be a solvent commonly used in crystallization or precipitation process such as methanol, ethanol, isopropanol, dimethylformamide, tetrahydrofuran, dioxane or dimethyl sulfoxide, dimethylacetamide or acetone.

Such a process enables one skilled in the art to obtain a POC, such as drospirenone, essentially in a crystallized form.

By routine experiments, one skilled in the art may determine the parameters of the precipitation process to be used so as to obtain the appropriate form of drospirenone. One skilled in the art may adjust the parameters of the precipitation process (such as the amounts of solvent, of water and optionally that of surfactant to be used) by routine experiments.

As described above, when the pharmaceutical composition of the various embodiments is a contraceptive composition, the composition may provide a pharmacokinetic profile of drospirenone such that the presence of an estrogenic compound to ensure the contraceptive efficiency of the compositions is not required.

Accordingly, in specific embodiments, the contraceptive compositions may not comprise an estrogen, including phytoestrogen. As used herein, the term "estrogen" refers to compounds, such as ethinylestradiol, mestranol or the phytoestrogen 8-prenylnaringenin, that are able to bind and activate estrogen receptors. In other words, the DRSP is present in the contraceptive compositions without estrogen, which means that DRSP is not associated with or combined with an estrogen as in the case of combined oral pill.

In some embodiments, drospirenone is the sole contraceptive ingredient comprised in the contraceptive compositions, i.e. the sole active ingredient able to prevent pregnancy when administered to a female patient of child bearing age.

However, in some specific embodiments, drospirenone may be combined with one or more progestogens. The term "progestogen", as used herein, may refer to any compound that binds and activates the progesterone receptor.

Progestogens include, but are not limited to, 17-hydroxy progesterone esters, 19-nor-17-hydroxy progesterone esters, 17-ethinyltestosterone and derivatives thereof, 17-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17-acetoxy-13-ethyl-17-a-ethinyl-gon-4-en-3-one oxime, cyproterone acetate, gestodene, desogestrel, etonorgestrel, norgestimate, norelgestromin, chlormadione and dienogest.

In some other embodiments, the drospirenone may be combined with one or more active ingredients which do not have contraceptive activities. Such active ingredients include, without being limited to, antiemetic agents, vitamins such as folic acid, vitamin $B_{12}$, vitamin D, minerals and oligo elements such as iron, iodine, selenium and others.

The contraceptive compositions may comprise drospirenone in an amount corresponding to a daily dosage, which prevents pregnancy when the contraceptive composition is administered to a woman over a single treatment period of 21 to 28 days.

As described in the Example 3 related to a clinical trial, the oral administration of a single daily dosage unit of a composition and comprising 3 mg of DRSP, obtains a mean $AUC_{0h\text{-}tlast}$ value of 368 ng*h/ml, which corresponds to 88% of the mean $AUC_{0h\text{-}tlast}$ resulting from the oral administration of a single dose of Yasminelle®.

In a specific embodiment, the pharmaceutical compositions may be a contraceptive composition, which comprises drospirenone in an amount corresponding to a daily dose of at least about 2 mg of drospirenone. At least about 2 mg of drospirenone may encompass at least about 3 mg of drospirenone, at least about 3.5 mg of drospirenone, and at least about 4 mg of drospirenone.

In some embodiments, the active daily dosage unit which includes the contraceptive composition as described above may comprise an active drug in amount ranging from about 2 mg to about 6 mg. In a specific embodiment, the POC may be in an amount ranging from about 2 mg to about 6 mg. In another specific embodiment, the POC may be DRSP. A daily dose ranging from about 2 mg to about 6 mg may encompass daily doses of 2.0 mg, 2.5 mg, 3.0 mg, 3.5 mg, 4.0 mg, 4.5 mg, 5.0 mg, 5.5 mg, and 6 mg. In a specific embodiment, the daily dose of the POC, such as DRSP, may be about 2 mg.

In a specific embodiment, the contraceptive compositions may comprise DRSP in an amount corresponding to a daily dosage, which ensures ovulation inhibition when the contraceptive composition is administered to a woman over a single treatment period of 21 to 28 days.

The daily dose of drospirenone may range from about 3 mg to about 6 mg, and specifically from about 3 mg to about 4.5 mg. In some embodiments, the amount of drospirenone may correspond to a daily dose of about 4.0 mg. However, the daily dose of drospirenone to be administered to a female patient in need thereof may also be adjusted depending on individual factors such as the age, the body weight, the general health and the diet of the female patient. The daily dose may also vary upon the drug interaction, which may occur. The daily dose may also vary upon the additional biological effect(s), other than the prevention of pregnancy, which may be sought through the administration of DRSP.

The daily dose of drospirenone to be daily administered to a female patient may be lower or higher than the doses previously mentioned. For example, a female patient in peri-menopause may require a higher or lower daily dosage of drospirenone, in order to improve her general conditions and, for example, in order to improve the regularity of her menstrual cycles. The adjustment of the daily dosage may be routinely determined by practitioners.

Figure 6A:
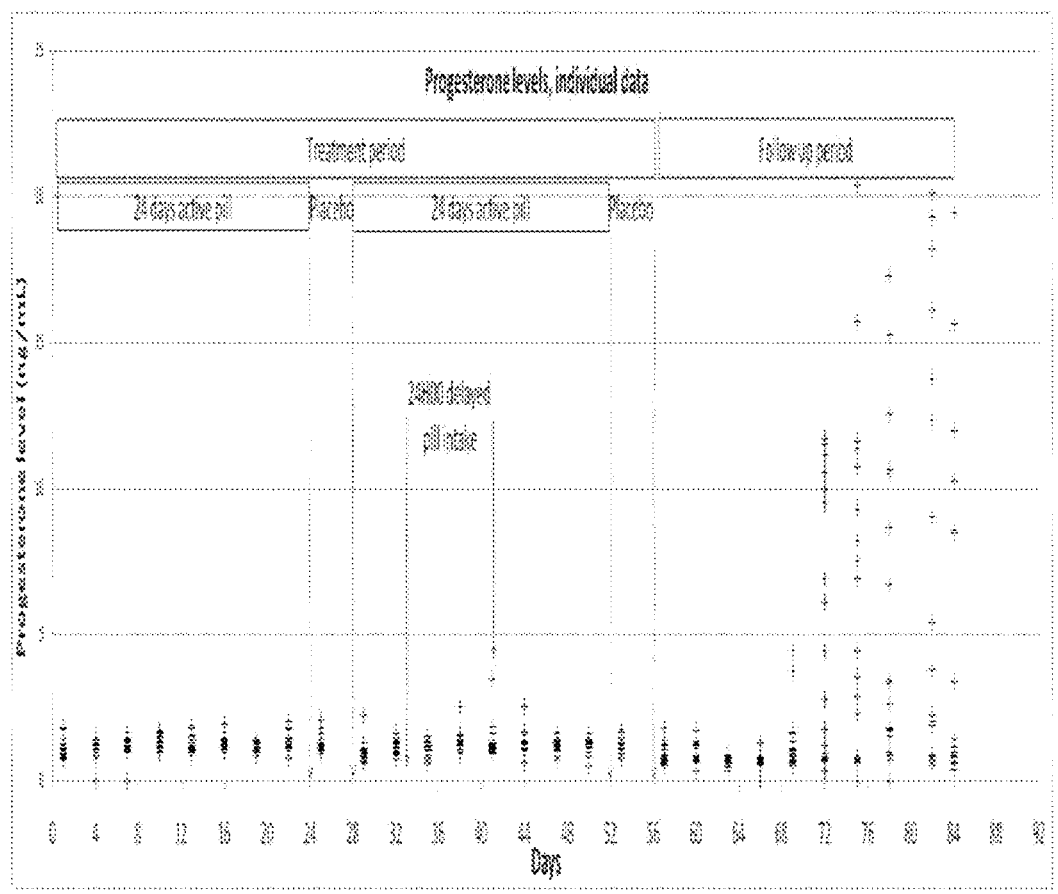
FIGS. 6A and 6B: Individual Plasma Levels of Progesterone and Estradiol in Patients During Treatment Period and Follow Up Period
Figure 6B:
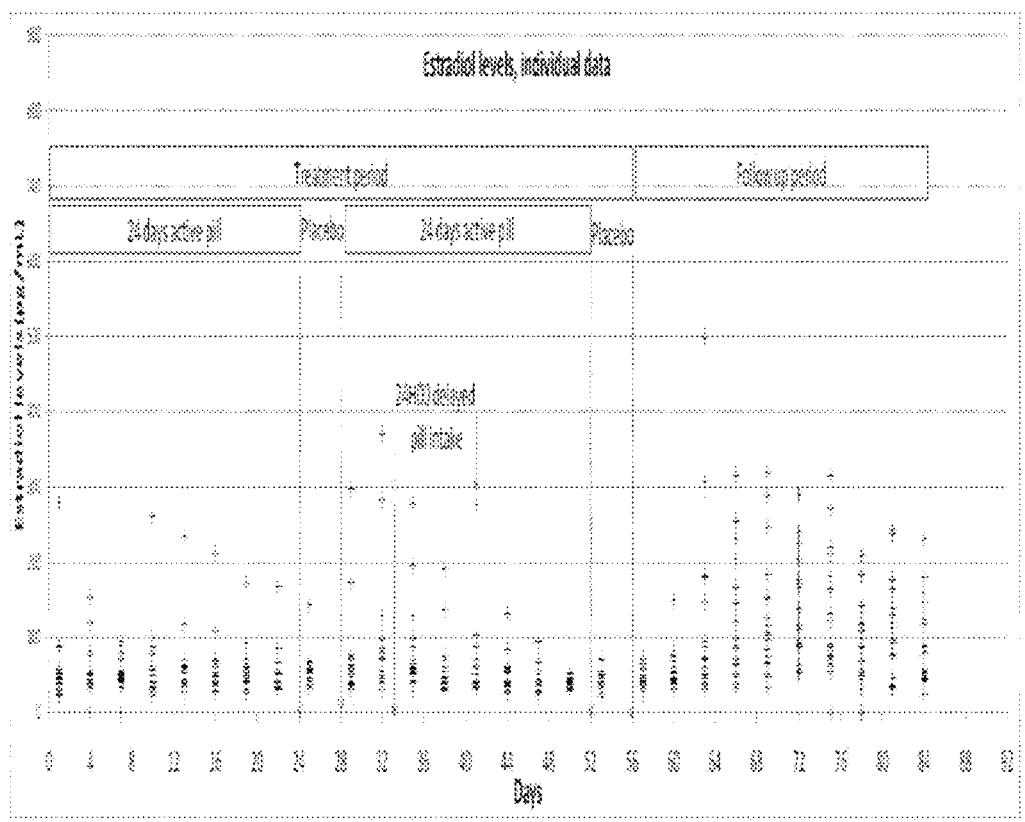

In another embodiment, the pharmaceutical composition may comprise an active contraceptive drug that allows for a 24/4 regimen. As defined herein, a "24/4 regimen" is a daily dosing regimen for establishing its contraceptive effect within a period of a total of 28 days that allows for the patient to have an active contraceptive drug administered once a day on 24 days of the 28 period, but allow the patient to skip up to 4 doses of the 28 day daily dosing regimen period. In other words a patient may miss up to 4 doses i.e., 4 days of a 28 day period, without taking the active contraceptive drug, and still continue to prevent pregnancy. A non-limiting example of the 24/4 regimen is depicted in FIGS. 6A-B. As demonstrated, the subjects were administered an active contraceptive drug (DRSP) on days 1-24 and a placebo on days 25-28 of each treatment cycle at a fixed hour. FIGS. 6A and 6B show the 24/4 regimen for two consecutive 28 day periods; the data show the plotted individual values for plasma progesterone levels and plasma estradiol levels, respectively. Accordingly, in a specific embodiment, the prevention of pregnancy may be due to the inhibition of ovulation.

The results show that during the 2 consecutive 24/4 regimens, no ovulation occurred. Conversely, upon cessation of treatment, during the 28-day follow-up cycle, the progesterone levels increased above 5.04 ng/mL in 17 out of 20 women showing a return of ovulation. The data confirms that the composition, when used as an active contraceptive drug (DRSP) upon a 24/4 regimen, provided reliable inhibition of ovulation, even due to the patient missing 4 doses during each 28 day period. Accordingly, in a specific embodiment, the embodiment may include a pharmaceutical composition comprising an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period.

In another specific embodiment, the active contraceptive drug may be a POC. In another specific embodiment, the POC may be DRSP. In another specific embodiment, the active contraceptive drug may inhibit ovulation. In another specific embodiment, the contraceptive effect may comprise inhibiting ovulation. In a specific embodiment, a pharmaceutical composition may comprise a POC for inhibiting ovulation, wherein the pharmaceutical composition allows for a 28 day daily dosing regimen, and wherein after initial administration of the POC has inhibited ovulation in a patient, the patient may skip up to 4 doses within any 28 day daily dosing regimen period. In a specific embodiment, the POC may be DRSP.

In a specific embodiment, the skipped up to 4 doses may be on non-consecutive days. In another example, only 2 doses of the 4 skipped doses may be on non-consecutive days (i.e. 2 skipped doses are on consecutive days). In another example, only 1 dose of the 4 skipped doses may be on non-consecutive days (i.e. 3 skipped doses are on consecutive days). In another embodiment, the skipped 4 doses may be on consecutive days, and so on.

In another embodiment, the pharmaceutical compositions may comprise a active contraceptive drug that also allows for a 28 day dosing regimen wherein a patient may skip up to two non-consecutive days of the active contraceptive drug, provided the skipped dose is taken within about 24 hrs afterwards. In other words, the prevention of pregnancy may be maintained even if the administration of the active contraceptive drug was delayed for 24 hours in two separate non-consecutive days within the 28 day daily dosing regimen. Accordingly, the day after each non-consecutive skipped dose, two doses are administered to the patient within about 24 hrs. FIGS. 6A-B also provides a non-limiting example of this concept. During the second 28 day period, the subjects took one tablet of 4 mg DRSP from day 1 to day 24 with the exception of day 5 and day 13 of the second 28 day period. On these two days, the tablet intake was delayed for 24 hours (i.e., no pill was taken on day 5 and day 13 and a tablet was taken once on day 6 and once on day 14, respectively). The data demonstrates that ovulation inhibition was maintained even if the administration of the tablet was delayed for 24 hours in two separate times within one 28 day period. Thus, a specific embodiment may be a pharmaceutical composition that allows during a 28 day daily dosing regimen for the patient to skip up to two non-consecutive days of an active contraceptive drug, provided the active contraceptive drug skipped dose is taken within about 24 hrs after the up to two skipped non-consecutive days. In another specific embodiment, the up to two skipped non-consecutive days may be included in a 28 day daily dosing regimen that also includes the 24/4 regimen, i.e., one 28 day daily dosing regimen may include 4 days of skipped doses and up to two non-consecutive days where the dose is delayed. In another embodiment, the active contraceptive drug may be a POC. In a specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment the POC may be drospirenone. In another specific embodiment, the daily dose of drospirenone may comprise a dosage amount of at least about 2 mg.

The pharmaceutical compositions are suitable for patients who are women of child-bearing age. It should be noted that the contraceptive methods may be suitable for women whose health conditions are not compatible with high peak of drospirenone plasma concentration. Such women include, without being limited to, subjects with renal impairment, women predisposed to hyperkalemia and subjects who concomitantly take potassium-sparing drugs. The contraceptive methods are also particularly suitable for women for whom the administration of estrogens is not recommended. Such women include, without being limited to, women predisposed to cardiovascular disorders, women who smoke and breast-feeding women. In a specific embodiment, the patient may have a higher risk for developing a complication from the administration of an estrogen than the general population. In a specific embodiment, the complication from the administration of an estrogen may be due to the patient having one or more conditions or characteristics selected from the group consisting of a higher risk for developing thromboembolism than the general population, acquired or genetic thrombophilia or hypercoaguability, an age of 35 years or over who smoke cigarettes, a higher risk for stroke than the general population, sickle-cell disease or sickle-cell anemia, a higher risk than the general population for myocardial infarction, and women currently lactating.

Many of the aforementioned health risks (e.g., thromboembolism, stroke, myocardial infarction) have been associated with patients having excess weight (i.e., overweight or obese). Therefore, in one embodiment, the pharmaceutical compositions described herein are also suitable for women who have excess weight or are considered overweight or obese. In one embodiment, a patient may be characterized as having excess weight, overweight or obese based on the patient's body mass index (BMI). BMI reflects a weight-to-height index that may be used to classify excess weight, overweight and obesity in adults. It is defined as a person's weight in kilograms divided by the square of his or her height in meters ($kg/m^2$).

In another embodiment, a patient may be considered has having excess weight, overweight or obese based on a clinical assessment of an individual patient by a physician or other health care professional.

Oral administration of a DRSP-based POC formulation in accordance with the embodiments herein to women with excess weight, including overweight or obese women, that is especially to women having a body mass index (BMI) of about 25 $kg/m^2$ or more or about 30 $kg/m^2$ or more, unexpectedly alters the number of days of bleeding events per treatment cycle as compared to a reference treatment of Cerazette or to women who do not have excess weight (BMI of less than about 25 $kg/m^2$). More precisely, it is shown in the examples herein that oral administration of a DRSP-based POC formulation to women with excess weight, overweight or obese women, that is especially to women having a body mass index (BMI) of about 25 $kg/m^2$ or about 30 $kg/m^2$ or more, greatly reduces the number of consecutive days of bleeding events.

As used here, "treatment cycle" comprises a total number of days including a predetermined number of days in which daily doses of a contraceptive agent is to be administered and a predetermined number of days in which a placebo is to be delivered or, alternatively, in which the contraceptive agent is not delivered. In one embodiment, the treatment cycle is 28 days, preferably 28 consecutive days, in which 21 to 28 daily doses of the DRSP-based compositions described herein are administered consecutively or non-consecutively, preferably for 21 to 28 consecutive days, and may comprise 0 to 7 days without treatment in which the DRSP-based compositions described herein are not administered or 0 to 7 days in which daily doses of placebo tablets are administered, depending on the number of days in which the daily doses of the DRSP-based composition are administered. The 0 to 7 days without treatment may be consecutive or non-consecutive, depending on whether administration of the DRSP-based compositions are consecutive or non-consecutive.

As used herein "bleeding events" includes vaginal bleeding and spotting that occurs during a woman's treatment cycle.

As used herein, "a number of days of bleeding events" includes the number of days in which bleeding events occur during a treatment cycle.

In one embodiment, administration of the DRSP-based POC formulation to women with excess weight (i.e. BMI of about 25 $kg/m^2$ or more) results in a reduction of at least about 5% in the number of days of bleeding events as compared to women without excess weight (i.e., BMI of about 24.9 $kg/m^2$ or less) during any treatment cycle. In one embodiment, the treatment cycle may be a period of 28 days and administration of the DRSP-based POC formulation in accordance with the embodiments may occur for 21 days, 22 days, 23 days, 24 days, 25 days, 26 days, 27 days or 28 days. The administration may be consecutive days or non-consecutive days. Administration of a daily placebo may take place on days on which the DRSP-based POC formulation is not administered.

It is understood "a reduction of at least about 5%" includes a reduction of at least about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, and about 30% or more.

In one embodiment, the mean percentage of reduction in the number of days of bleeding events per treatment cycle in women with excess weight treated with the DRSP-based POC formulation as compared to women with no excess weight subjected to the same contraceptive treatment, may be evaluated for 3 consecutive treatment cycles of treatment and may range from about 15% to about 30%, from about 20% to about 25%, or from about 22% to about 24%.

The percentage of reduction in the number of days of bleeding events per treatment cycle in women with excess weight may be affected by certain factors, such as initial weight, age, time elapsed from the initial treatment cycle.

In another embodiment, administration of the DRSP-based POC formulation to obese women (i.e., BMI of about 30 $kg/m^2$ or more) results in a reduction of at least about 10% in the number of days of bleeding events as compared to non-obese women (i.e., BMI of about 29.9 $kg/m^2$ or less) during any treatment cycle. In one embodiment, the treatment cycle is a cycle of 28 days and administration of the DRSP-based POC formulation in accordance with the embodiments herein occurs for 21 days, 22 days, 23 days, 24 days, 25 days, 26 days, 27 days or 28 days. The administration may be consecutive days or non-consecutive days. Administration of a daily placebo may take place on days on which the DRSP-based POC formulation is not administered.

It is understood "a reduction of at least about 10%" includes a reduction of at least about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, and about 50% or more.

In a further embodiment, the mean percentage of reduction in the number of days of bleeding events per treatment cycle in obese women treated with the DRSP-based POC formulation as compared with non-obese women subjected to the same contraceptive treatment, may further be evaluated for 3 consecutive treatment cycles of treatment and mean percentage of reduction in the number of days of bleeding events per treatment cycle in obese women treated with the DRSP-based POC formulation may range from about 30% to about 75%, from about 40% to about 75% or from about 45% to about 65%.

The reduction in the number of days of bleeding events per treatment cycle demonstrated in Example 7. The reduced incidence of bleeding events is believed to benefit women with excess weight and significantly ameliorate their comfort, while at the same time providing a compliant contraceptive treatment, and thus increased efficiency in the contraceptive treatment.

In addition to the reduction in the number of days of bleeding events, oral administration of a DRSP-based POC treatment to women with excess weight may surprisingly provide weight loss benefits, as shown in Example 8, which were not observed on women of normal weight.

Indeed, such DRSP-based contraceptive compositions, when administered to women with excess weight, results in an average significant weight loss and no change to the heart rate as compared to women from the general population, for which, no effect on weight change and a slight significant increase of heart rate is observed during the course of this treatment.

Therefore, the DRSP-based contraceptive treatments will provide higher compliance rates among women with excess weight, thereby reducing the risks of unwanted pregnancy. In one embodiment, the composition may comprise DRSP as the sole contraceptive ingredient comprised in a daily active dosage unit with an amount of DRSP of at least about 3 mg for use as a contraceptive for a female patient with excess weight, an overweight or obese female patient. In another embodiment, the daily active dosage unit may comprise DRSP in an amount of about 3.5 mg to about 4.5 mg.

In one embodiment, administration of the DRSP-based contraceptive formulations described herein may result in a reduction in the number of days of bleeding events per treatment cycle in women with excess weight (i.e., BMI of about 25 $kg/m^2$ or more) as compared to women without excess weight (i.e., BMI of about 24.9 $kg/m^2$ or less). This reduction may be about (i) about 12 to about 32% or more, about 17 to about 27% or more, or about 20 to about 24% or more during treatment cycles 2-4, (ii) about 17 to about 37% or more, about 22 to about 32% or more, or about 25 to about 29% or more during treatment cycles 2-6; (iii) about 20 to about 40% or more, about 25 to about 35% or more, or about 28 to about 32% or more during treatment cycles 2-9; (iv) about 13-33% or more, about 18 to about 28% or more, or about 21 to about 25% or more during treatment cycles 5-7; or (v) about 12 to about 32% or more, about 17 to about 27% or more, or about 20 to about 24% or more during treatment cycles 7-9. In one embodiment, a treatment cycle comprises 28 day in which a single daily dosage unit of the DRSP-based contraceptive formulations is administered to the patient for 21 days, 22 days, 23 days, 24 days, 25 days, 26 days, 27 days or 28 days. The administration may be consecutive days or non-consecutive days.

In another embodiment, administration of the DRSP-based contraceptive formulations described herein may result in a reduction in the number of days of bleeding events in obese women (i.e., BMI of about 30 $kg/m^2$ or more) per treatment cycle as compared to women who are not obese (i.e., BMI of about 29.9 $kg/m^2$ or less). This reduction may be about (i) about 50 to about 70% or more, about 55 to about 65% or more, or about 58 to about 62% or more during treatment cycles 2-4; (ii) about 57 to about 77% or more, about 62 to about 72% or more, or about 65 to about 69% or more during treatment cycles 2-6; (iii) about 59 to about 79% or more, about 64 to about 74% or more, or about 67 to about 71% or more during treatment cycles 2-9; (iv) about 38 to about 58% or more, about 43 to about 53% or more, or about 46 to about 50% or more during treatment cycles 5-7; or (v) about 52 to about 72% or more, about 57 to about 67% or more or about 60 to about 64% or more during treatment cycles 7-9. In one embodiment, a treatment cycle comprises 28 day in which a single daily dosage unit of the DRSP-based contraceptive formulations is administered to the patient for 21 days, 22 days, 23 days, 24 days, 25 days, 26 days, 27 days or 28 days. The administration may be consecutive days or non-consecutive days.

Thus, in certain embodiments, the DRSP-based contraceptive formulations contain drospirenone as the sole active agent and is comprised in a daily active dosage unit in an amount of about 3 mg or more or from about 3 mg to about 6 mg, for use as a contraceptive for reducing the number of days of bleeding events per treatment cycle (i) in overweight women by about 5% or more, and preferably about 10% or more, as compared to non-overweight women subjected to the same contraceptive treatment or (ii) in obese women by about 10% or more, and preferably about 20% or more, as compared to non-obese women subjected to the same contraceptive treatment.

In another embodiment, methods of providing contraception in a patient having excess weight are provided. The method comprises administering the pharmaceutical compositions described herein, including the DRSP-based contraceptive formulations containing drospirenone as the sole active agent, to a patient having a BMI of about 25 $kg/m^2$ for an initial treatment cycle and for subsequent consecutive treatment cycles, the pharmaceutical composition being administered daily for at least a portion of the initial and subsequent consecutive treatment cycles. The method may further comprise administering the pharmaceutical compositions to a patient having a BMI of about 30 $kg/m^2$ for an initial treatment cycle and for subsequent consecutive treatment cycles, the pharmaceutical composition being administered daily for at least a portion of the initial and subsequent consecutive treatment cycles.

In one aspect of the embodiment, the average number of days of bleeding events in second through fourth treatment cycles of administration does not exceed about 13% per treatment cycle. In another aspect of the embodiment, the average number of days of bleeding events in a second through sixth treatment cycles of administration does not exceed about 11% per treatment cycle. In a further aspect of the embodiment, the average number of days of bleeding events in one of second through ninth treatment cycles of administration, fifth through seventh treatment cycles of administration, or seventh through ninth treatment cycles of administration, does not exceed about 10% per treatment cycle.

In another aspect of the embodiment, the average number of days of bleeding events in second through fourth treatment cycles of administration of fifth through seventh treatment cycles of administration does not exceed about 7%. In another aspect of the embodiment, the average number of days of bleeding events in one or more of second through sixth treatment cycles of administration, second through ninth treatment cycles of administration or seventh through ninth treatment cycles of administration does not exceed about 5%.

In a further aspect of the embodiment, the number of days of bleeding events in an overweight or obese patient does not exceed about 20%, about 15%, about 10%, about 8%, or about 5% in any treatment cycle subsequent to an initial treatment cycle.

In a specific embodiment, the pharmaceutical compositions may further comprise one or more pharmaceutically acceptable excipients.

As used herein, "dosage unit" is the physical form in which the contraceptive drugs of the present invention are produced, dispenses and/or administered to the patient. The contraceptive drugs are generally administered as part of a formulation that includes pharmaceutically acceptable excipients. Dosage units may include unique physical and pharmaceutical characteristics. Dosage units may be solid, liquid, or gaseous. Solid forms include pills, tablets, capsules, gel capsules, softgels, lozenges, and wafers. Such solid forms may be used as oral dosage units. In one embodiment, the dosage unit is manufactured. The manufactured dosage units may include pills, tablets, capsules, gel capsules, softgels, lozenges and wafers. The oral dosage units may be provided in a swallowable form. The phrase "swallowable form" refers to any compositions that do not readily dissolve when placed in the mouth and may be swallowed whole without any chewing or discomfort. Such compositions, in one embodiment, may have a rounded shape with no sharp edges and a smooth, uniform and substantially bubble free outer coating.

The pharmaceutical compositions may be formulated according to standard methods such as those described, e.g., in REMINGTON: THE SCIENCE AND PRACTICE OF PHARMACY (Lippincott Williams & Wilkins; 21st Edition, 2005).

Pharmaceutically acceptable excipients that may be used to formulate the contraceptive composition, in particular, described in the HANDBOOK OF PHARMACEUTICAL EXCIPIENTS, American Pharmaceutical Association (Pharmaceutical Press; 6th Revised edition, 2009). Examples of appropriate excipients include, but are not limited to, fillers, carriers, diluents, binders, anti-caking agents, plasticizers, disintegrants, lubricants, flavors, buffering agents, stabilizers, colorants, dyes, anti-oxidants, anti-adherents, softeners, preservatives and glidants.

In some embodiments, the contraceptive compositions may comprise one or more excipients selected from the group of binders, fillers, glidants and lubricants. Examples of fillers include, without being limited to, lactose anhydrous, microcrystalline cellulose, starch, pregelatinized starch, modified starch, dibasic calcium phosphate dihydrate, calcium sulfate trihydrate, calcium sulfate dihydrate, calcium carbonate, lactose, dextrose, sucrose, mannitol and sorbitol and combinations thereof. Examples of lubricants include, without being limited to, magnesium stearate, calcium stearate, zinc stearate, talc, propylene glycol, PEG, stearic acid, vegetable oil, sodium benzoate, sodium lauryl sulfate, magnesium lauryl sulfate, mineral oil polyoxyethylene monostearate and combinations thereof. Examples of binders include, without being limited to, starches, e.g., potato starch, wheat starch, corn starch; gums, such as gum tragacanth, acacia gum and gelatin; microcrystalline cellulose, hydroxypropyl cellulose, hydroxyethyl cellulose and hydroxypropylmethyl cellulose; polyvinyl pyrrolidone and combinations thereof. Examples of glidants include silicon dioxide, magnesium trisilicate, powdered cellulose, starch, talc and tribasic calcium phosphate.

In one specific embodiment, the pharmaceutically acceptable excipients include one or more of the following: pregelatinized starch, lactose monohydrate, anhydrous lactose, microcrystalline cellulose, corn starch, povidone, hydroxypropylmethyl cellulose, colloidal silicon dioxide, and vegetal magnesium stearate.

In one embodiment, the oral dosage unit comprises from about 1%, about 2%, about 3%, about 4%, about 5%, about 6%, about 7%, about 8%, about 9%, about 10%, about 11%, about 12%, about 13% about 14%, about 15%, about 16%, about 17%, about 18%, about 19%, about 20% by weight of the total weight of the oral dosage unit of the active contraceptive drug and about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, and about 99% by weight of the one or more pharmaceutically acceptable excipients, based on the total weight of the oral dosage unit.

In another specific embodiment, the pharmaceutical compositions do not comprise a significant amount of a surfactant agent. For example, a significant amount of a surfactant agent may impair the in vitro dissolution profile of DRSP by increasing its initial rate of dissolution. Surfactant agents include non-ionic surfactants such as polyoxyethylene sorbitan fatty acid esters and ionic surfactants such as sodium lauryl sulphate. The pharmaceutical compositions therefore comprise less than about 10%, less than about 9%, less than about 8%, less than about 7%, less than about 6%, less than about 5%, less than about 4%, less than about 3%, less than about 2%, less than about 1% by weight of the surfactants based on the total weight of the pharmaceutical composition. In another embodiment, the pharmaceutical compositions do not include surfactants.

In some embodiments, the pharmaceutical composition may comprise drospirenone, at least one binder and at least one filler wherein:
  (i) the amount of drospirenone accounts for about 1% to about 10% by weight
  (ii) the amount of the at least one binder accounts for about 50% to about 65% by weight and
  (iii) the amount of the at least one filler accounts for about 25% to about 35% by weight,
the percentages by weight being related to the total weight of the contraceptive composition.

In some embodiments, the contraceptive composition may further comprises at least one glidant and at least one lubricant wherein:
  (i) the amount of the at least one glidant accounts for about 0.2% to about 6% by weight and
  (ii) the amount of the at least one lubricant accounts for about 0.2% to about 0.6% by weight, the percentages by weight being related to the total weight of the contraceptive composition.

It goes without saying that the active drug, such as drospirenone, may be used in a particle form having the specific surface area and/or the $d_{90}$, $d_{10}$ and $d_{50}$ particle sizes which are fully-described in the present specification. The contraceptive composition may optionally comprise additional excipients, which may accounts for about 0.1% to about 10% by weight of the composition.

In some other embodiments, the contraceptive compositions comprises drospirenone, at least one binder, at least one filler, at least one glidant, and at least on lubricant wherein:
  (i) the at least one binder is microcrystalline cellulose
  (ii) the at least one filler is anhydrous lactose
  (iii) the at least one glidant is silicon dioxide and
  (iv) the at least one lubricant is magnesium stearate.

The contraceptive compositions may be formulated in a galenic form suitable for oral administration. Such forms include, without being limited to, tablets, caplets, granules, pills, capsules, powders and suspension.

In specific embodiments, the contraceptive compositions may be formulated in a solid form for oral administration such as tablets, capsules, granules, caplets and pills. Such solid forms are particularly appropriate to be used as daily active dosage unit in the contraceptive kit.

When the pharmaceutical composition is formulated in solid forms such as tablets or pills, the solid forms may be conveniently coated with a suitable film-forming agent such as hydroxypropylmethyl cellulose, hydroxypropyl cellulose or ethyl cellulose, to which a suitable excipient may optionally be added, e.g., a softener such as glycerol, propylene glycol, diethylphthalate or glycerol triacetate, a filler such as sucrose, sorbitol, xylitol, glucose or lactose, or a colorant such as titanium hydroxide, etc. The pharmaceutical composition in the form of tablets, pills or granules may be prepared by conventional methods such as direct compression, dry granulation and wet granulation. In some embodiments, the solid forms are obtained by direct compression.

A method for preparing the contraceptive composition as described herein may be provided which comprises the steps of:
(i) providing drospirenone in a particle form as fully-described previously in the present specification
(ii) providing one or more pharmaceutically acceptable excipients; and
(iii) mixing the drospirenone provided in step (i) with the one or more excipients provided in step (ii).

As fully-described above, the Applicant provides technical guidelines to obtain a composition comprising DRSP in a form such that:
(i) no more than about 50% of the drospirenone initially present in the composition is dissolved within 30 minutes and
(ii) at least about 50% of the drospirenone is dissolved in a time range from about 3 hours to about 4 hours, when the composition is subjected to an in vitro dissolution test, the percentages of drospirenone being related to the amount of drospirenone initially present in the composition.

A DRSP containing composition with such an in vitro dissolution profile or the in vivo pharmacokinetic profile fully-described above may be achieved by various other ways.

By routine experiments and in view of his general knowledge, one skilled in the art may modify (i) the particle size distribution of DRSP and (ii) the amounts and the nature of excipients in order to obtain other alternative compositions displaying the in vitro dissolution profile and the in vivo pharmacokinetic profile described in the present application. For example, one skilled in the art may conceive a composition comprising (i) micronized DRSP together with (ii) a slow release agent in order to diminish the dissolution rate of said DRSP.

One skilled in the art may also combine (i) large particles of DRSP together with (ii) a surfactant and/or a wetting agent in order to ensure the dissolution of said DRSP. Generally, non-micronized and essentially crystallized form DRSP is preferably used for preparing the pharmaceutical composition. In one embodiment, at least over about 50% of the DRSP is present in crystallized form.

As intended herein, at least over about 50% of the DRSP encompasses at least over about 55%, at least over about 60%, at least over about 65%, at least over about 70%, at least over about 75%, at least over about 80%, at least over about 85%, at least over about 90%, at least over about 95%, at least over about 96%, at least over about 97%, at least over about 98%, at least over about 99%, at least over about 99.5% of the DRSP initially present in the contraceptive composition.

2. Contraceptive Methods

When orally administered, the pharmaceutical composition provides a significantly improved pharmacokinetic profile for drospirenone characterized by a similar $AUC_{0h-tlast}$, a delayed and a reduced $C_{max}$ as compared to that obtained with Yasminelle®.

In order to provide contraception based on the pharmaceutical composition, the presence of an estrogen such as ethinylestradiol or 8-prenylnaringenin may not be required to ensure the ovulation inhibition and the cycle stability.

Moreover it is expected that such compositions may be more reliable than POCs described in the prior art.

The contraceptive compositions that do not comprise an estrogen are thus particularly appropriate to be used as POC.

Accordingly, the use of the pharmaceutical composition as described herein is provided for preparing a contraceptive progestogen-only pill or for preparing a contraceptive kit.

Also disclosed herein is an oral contraceptive method for a female patient in need thereof characterized in that it comprises the step of administering active daily dosage units consisting of a pharmaceutical composition as fully-described herein to the female patient over a period of several consecutive days preferably over a period of 21 to 28 days.

As used herein a contraceptive method relates to a method for preventing pregnancy.

As used herein, "an active daily dosage unit" may refer to a dosage unit which is able to prevent pregnancy when daily administered to a female patient over a period selected from periods of 21 to 28 consecutive days.

In certain embodiments, the active daily dosage unit is able to inhibit ovulation when daily administered to a female patient over a period selected from periods of 21 to 28 consecutive days.

As used herein, a female patient refers to a woman of child-bearing age i.e. from the puberty to the menopause. Women of child-bearing age also include women in peri-menopause. In one embodiment, the female patient in need thereof may be a woman having excess weight. In another embodiment, the female patient in need thereof may be an overweight woman, having a BMI of about 25.0 kg/m² to about 29.9 kg/m². In a further embodiment, the female patient in need thereof may be an obese woman having a BMI of about 30.0 kg/m² or more. In a yet a further embodiment, the female patient may be an overweight or obese woman as determined by a clinical assessment by a physician or other healthcare professional.

The daily dosing regimen of DRSP to be administered to patient having excess weight, an overweight or obese patient may be adjusted depending on individual factors such as the age, the body weight, the general health, and the diet of the patient. The daily dosing regimen may also vary upon the drug interaction that may occur. The daily dosing regimen may also vary upon the additional biological effect(s), other than the prevention of pregnancy, which may be sought through the administration of DRSP.

The daily dosing regimen of DRSP to be daily administered to a female patient may be lower or higher than the doses previously mentioned. For example, a female patient in peri-menopause may require a higher or lower daily dosage of DRSP, in order to improve her general conditions and, for example, in order to improve the regularity of her menstrual cycles.

In an embodiment, the daily dosage units may not comprise an estrogen.

In some embodiments, the drospirenone is the sole contraceptive ingredient comprised in the contraceptive composition.

The contraceptive method may generally be performed for a period time corresponding to the average length of a menstrual cycle i.e. 28 days and may be iterated during several consecutive months, even, for several years.

In some embodiments, the contraceptive method may consist in administering "continuously" daily dosage units. Such a method does not comprise a free-contraceptive period i.e. a period in which no contraceptive is administered. In other embodiments, the contraceptive method may comprises two consecutive phases:
- a first phase wherein active daily dosage units which do not comprise estrogen are administered to the female patient over a period of 21 to 27 consecutive days and
- a second phase wherein no contraceptive composition is administered to the female patient over a period of 1 to 7 consecutive days.

As used herein a period of 1 to 7 consecutive days include periods of 1 day, of 2 consecutive days, of 3 consecutive days, of 4 consecutive days, of 5 consecutive days, of 6 consecutive days, and of 7 consecutive days.

As used herein a period of 21 to 27 consecutive days include periods of 21 consecutive days, of 22 consecutive days, of 23 consecutive days, of 24 consecutive days, of 25 consecutive days, of 26 consecutive days, and of 27 consecutive days.

As mentioned above, the duration of the first phase plus the second phase is preferably 28 days.

In the first phase, the composition of active daily dose units may remain constant, in particular in respect to the daily amount of drospirenone.

In some other embodiments, the composition of the active daily dose units may vary, in particular, in respect to the daily amount of drospirenone.

The second phase is a free-contraceptive period i.e., a phase during which no contraceptive ingredients is administered to the female patient. During the second phase, daily placebo dosage units may be administered to the female patient. In some other cases, no pill is administered to the female patient.

Such a second phase may enable regular menstrual bleedings to occur and thus may enable to mimic the natural menstrual cycle.

Moreover, the second phase is believed to enable the secretion of endogenous estradiol, which may have some benefits on bone metabolism of the female patient.

As used herein, the term "active daily dosage unit" refers to physically discrete units suitable as unitary dosage, which comprises a contraceptive composition as fully described here above in the present specification. As mentioned previously, the active daily dosage unit may generally comprise a drospirenone amount of about 3.0 mg to about 6.0 mg, more preferably, of about 3.5 mg to about 4.5 mg.

In some embodiments, the first phase of the contraceptive method lasts from 21 to 24 consecutive days and the second phase of the contraceptive method lasts from 4 to 7 consecutive days.

In some embodiments, the first phase of the contraceptive method lasts 24 consecutive days and the second phase of the contraceptive method lasts 4 consecutive days. The contraceptive method may provide a high contraceptive efficiency without the disadvantages (i.e., spotting, irregular bleedings, etc.) observed for marketed POC methods such as Cerazette®.

The contraceptive method may exhibit a higher reliability than other POC methods by allowing the patients to be a bit less compliant with treatment (i.e. allowing episodic missing pills) without risking unwanted pregnancy (see Example 5 hereunder).

The contraceptive method is suitable for women of child-bearing age.

It should be noticed that the contraceptive method may be suitable for women whose health conditions is not compatible with high peak of drospirenone plasma concentration. Such women include, without being limited to, subjects with renal impairment, women predisposed to hyperkalemia and subjects who concomitantly take potassium-sparing drugs.

The contraceptive method may also particularly suitable for women for whom the administration of estrogens is not recommended. Such women include, without being limited to, women predisposed to cardiovascular disorders, women who smoke and breast-feeding women. The contraceptive methods may also be particularly suitable for women with excess weight as many of the risk factors that recommend against the administration of estrogen are associated with being overweight and obese. The estrogen component of contraceptive formulations have been considered to be mainly responsible for the prothrombotic effect of combined hormonal contraception.

In one embodiment, the contraceptive methods may be indicated for administration to a patient with excess weight or an overweight patient, an obese patient or both which, in addition to providing effective contraception, also results in one or more of the following beneficial effects after an initial treatment cycle of administration: a loss in body weight and a decrease in the resting heart rate, or a reduction in the number of days of bleeding events per treatment cycle. The one or more beneficial effects may be observed after an initial treatment cycle of administration of the pharmaceutical composition. In an embodiment, the beneficial effect may be observed at the end of the second through the thirteenth treatment cycle of administration as compared to the initial treatment cycle of administration.

3. Contraceptive Kits

Disclosed herein are contraceptive kit based on the contraceptive compositions as fully-described in the present application. Such a kit is particularly suitable for use in the contraceptive methods as described above.

The contraceptive kit comprises one or more packaging units.

One or more packaging units may include, without being limited to, 1 packaging unit, 2 packaging units, 3 packaging units, 4 packaging units, 5 packaging units and 6 packaging units.

Each packaging unit comprises from 21 to 28 daily active dosage units. As fully described above, each daily active dosage unit consists of a contraceptive composition In some embodiments, the contraceptive kit comprises one or more packaging units wherein each packaging unit comprises 21 to 28 daily active dosage units and wherein each daily active dosage unit comprises drospirenone in a non-micronized particle form such that:
  (i) no more than 50% of the drospirenone initially present in the daily active dosage unit is dissolved within 30 minutes and
  (ii) at least 50% of the drospirenone is dissolved in a time range from 3 hours to 4 hours, when the daily active dosage unit is subjected to an in vitro dissolution test, the percentages of drospirenone being related to the amount of drospirenone initially present in the daily active dosage unit In other embodiments, the contraceptive kit comprises one or more packaging units wherein each packaging unit comprises 21 to 28 daily active dosage units and wherein the oral administration of a daily active dosage unit provides a pharmacokinetic profile for DRSP characterized by the following features:
 (i) a mean $t_{max}$ of at least about 2.2 h and
 (ii) a mean $C_{max}$ which is less than about 30 ng/ml, In some embodiments, the oral administration of the daily active dosage unit provides a pharmacokinetic profile further characterized by a mean $AUC_{0h\text{-}tlast}$ of at least 300 ng*ml/h, more preferably of at least 350 ng*ml/h.

As fully described above, the daily active dosage units preferably do not comprise any estrogen or estrogen derivative such as ethinyl estradiol, mestranol or 8-prenylnaringenin. In other words, the DRSP is preferably present in the daily active dosage units without estrogen.

In other embodiments, DRSP is the sole contraceptive ingredient comprised within the daily active dosage units.

In some other embodiments, contraceptive kit comprises one or more packaging units wherein each packaging unit comprises 21 to 28 daily active dosage units and wherein:
 (a) the amount of the drospirenone in each daily active dosage unit is at least about 2 mg, without estrogen, and
 (b) the oral administration of a daily active dosage unit provides a pharmacokinetic profile for DRSP characterized by the following features:
  (i) a mean $t_{max}$ ranges from 2.2 h to 6 h and
  (ii) a mean $C_{max}$ which is less than about 30 ng/ml.

In other embodiments, the contraceptive kit comprises one or more packaging units wherein each packaging unit comprises 21 to 28 daily active dosage units and wherein:
 (a) the amount of drospirenone in each daily active dosage unit is at least about 2 mg without estrogen, and
 (b) each daily active dosage unit comprises drospirenone in a form such that:
  (i) no more than about 50% of the drospirenone initially present in the daily active dosage unit is dissolved within about 30 minutes and
  (ii) at least about 50% of the drospirenone is dissolved in a time range from about 3 hours to about 4 hours,
when the daily active dosage unit is subjected to an in vitro dissolution test according to the USP XXIII Paddle Method, the percentages of drospirenone being related to the amount of drospirenone initially present in the daily active dosage unit.

In further embodiments, the contraceptive kit comprises one or more packaging units wherein each packaging unit comprises 21 to 28 daily active dosage units and wherein:
 (a) the amount of DRSP in each daily active dosage unit is at least about 3 mg without estrogen, and
 (b) each daily active dosage unit comprises DRSP in a form such that:
  (i) no more than about 50% of the DRSP initially present in the daily active dosage unit is dissolved within 30 minutes and
  (ii) at least about 50% of the DRSP is dissolved in a time range from about 3 hours to about 4 hours,
when the daily active dosage unit is subjected to an in vitro dissolution test according to the USP XXIII Paddle Method, the percentages of DRSP being related to the amount of DRSP initially present in the daily active dosage unit.

Each packaging unit optionally comprises from 1 to 7 daily dosage units of a pharmaceutically acceptable placebo.

In some embodiments, the contraceptive kit is characterized in that each packaging unit comprises 28 daily dosage units and no daily dosage unit of a pharmaceutically acceptable placebo. Such a contraceptive kit is particularly appropriate to perform the contraceptive method may consists in administering "continuously" DRSP without free-contraceptive period.

In other embodiments each packaging unit comprises:
 21 to 27 active daily dosage units consisting of a contraceptive composition as fully described in the present application and
 optionally, 1 to 7 daily dosage units of a pharmaceutically acceptable placebo Such a contraceptive kit is particularly appropriate to perform the contraceptive method of the which may comprise
 a first phase wherein active daily dosage units which may not comprise estrogen are administered to the female patient over a period of 21 to 27 consecutive days followed by
 a second phase wherein no contraceptive composition is administered to the female patient over a period of 1 to 7 consecutive days.

In some other embodiments, each packaging unit of the kit comprises 24 daily dosage units comprising an effective amount of a contraceptive composition as described herein and, optionally, 4 daily dosage units of a pharmaceutically acceptable placebo.

The packaging unit as described above may have one of the conventional forms usually used for oral contraceptives.

For example, the packaging unit may be a conventional blister pack comprising the appropriate number of dosage units in a sealed blister pack with a cardboard, paperboard, foil or plastic backing and enclosed in a suitable cover. Each blister container may be conveniently numbered or marked in order to facilitate compliance.

The packaging unit may contain daily dosage units in the order in which they are to be taken, i.e. starting with the first of the at least 21 dosage units that contain the combination of drospirenone optionally followed by 7 or less empty blisters or by 7 or less dosage units that comprise a pharmaceutically acceptable placebo.

The kit may comprise other appropriate components such as instructions for use.

The following examples are illustrative and are not intended to limit the scope of the invention as claimed.

EXAMPLES

Example 1

Preparation of Tablets

A. Preparation of Drospirenone.

Drospirenone (DRSP) was prepared according to a process similar to that described in WO 2006/061309. In order to obtain DRSP with an appropriate particle size distribution, DRSP was subjected to an additional process of precipitation as described herein.

Five batches of DRSP were prepared by variants of the above-mentioned precipitation process.

The analysis of the particle size distribution of each batch was performed by laser diffraction method in wet dispersion (Helos sensor, Sympatec with the wet disperser Quixel). The dispersant used was water. The full particle dispersion was ensured by ultrasonication.

The specific area was determined by the BET method. The results obtained are shown in Table 1 below.

TABLE 1 particle size distribution parameters
and specific area of DRSP batches

| | DRSP Batch | | | | |
|---|---|---|---|---|---|
| | PR100003 | 080169 | 080204 | 080257 | 080053 |
| d50 (μm) | 22.4 | 24.5 | 13.1 | 12.6 | 19.8 |
| d90 (μm) | 37.4 | 37.1 | 24.8 | 23.4 | 34.2 |
| d10 (μm) | 5.9 | 2.9 | 4.4 | 5.3 | 7.2 |
| d99 (μm) | 56.1 | 48.9 | 34.5 | 35.3 | 44.8 |
| Specific area (m$^2$/g) | 0.26 | 0.45 | 0.83 | 0.77 | 0.63 |

The cumulative distribution function and the probability density function for batch 080053 are shown in FIG. 1.

B. Preparation of Tablets.

The tablets are prepared by direct compression. The composition of tablets is described hereunder.

TABLE 2A composition of tablets (A-3 mg, inventive)

| Material | mg/tablet | (%) |
|---|---|---|
| Drospirenone (Batch 080053) | 3.00 | 4.74 |
| Microcrystalline cellulose 102 | 36.48 | 57.60 |
| Anhydrous lactose DCL21 | 20.16 | 31.83 |
| Silicon dioxide | 3.36 | 5.31 |
| Magnesium stearate | 0.33 | 0.53 |
| TOTAL | 63.33 | 100.00 |

Example 2

In Vitro Dissolution Profiles

A. Comparison of Tablets A-3 mg (DRSP) with Yasminelle® (Comparative).

The rate of dissolution of drospirenone from the tablets prepared in Example 1 (A-3 mg) was determined by the USP XXIII Paddle Method using a USP Dissolution Test Apparatus 2 including 6 covered glass vessels and 6 paddles.

Tablets were placed in 900 ml water at a temperature of 37° C.±(0.5° C.) and stirred at 50 rpm. The amount of drospirenone released in water was measured over several hours. The mean percentages of DRSP released (which were related to the amount of drospirenone initially present in the each tablet) were calculated and plotted versus time in order to provide the in vitro dissolution profile of DRSP.

Figure 2:
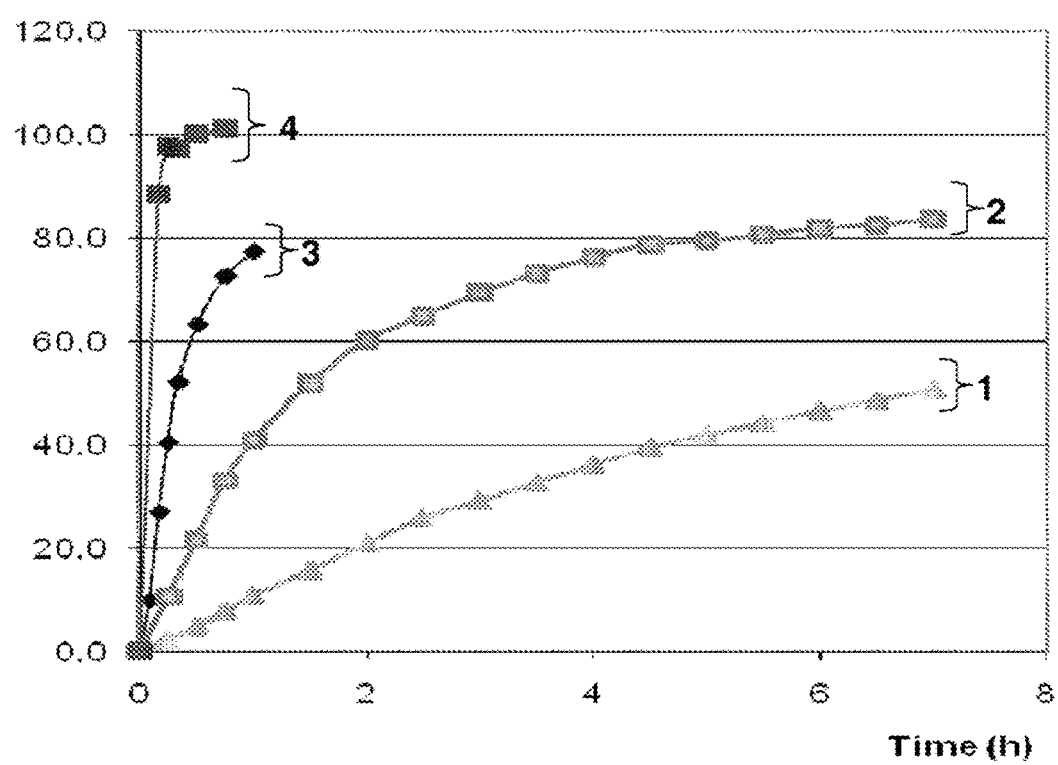
FIG. 2: In vitro Dissolution Profiles

The in vitro dissolution profile of tablets A-3 mg is shown in FIG. 2 (see curve no2).

FIG. 2 also provides the dissolution profile obtained for Yasminelle®—tablets which comprised micronized DRSP (comparative) (see curve no 4).

Surprisingly, the initial dissolution rate for tablets obtained in Example 1 (A-3 mg) was significantly reduced as compared to that of the Yasminelle® tablet since only about 22% of DRSP initially present in the tablets was released within 30 min (versus almost 100% for Yasminelle® in 30 min). The final dissolution percentage of DRSP from tablets obtained in Example 1 was more than about 80%. As described in Example 3, Part 1, such an in vitro dissolution profile is correlated with a different and improved pharmacokinetic profile as compared to Yasminelle®.

B. Examples of Other In Vitro Dissolution Profiles.

In order to illustrate the correlation between the in vitro dissolution profile of drospirenone and its pharmacokinetic profile upon oral administration, two other types of DRSP-containing tablets (comparative) were prepared. The composition of these tablets is distinct from that of tablet A-3 mg. Each tablet comprises 3 mg of DRSP in a non-micronized form.

The first type of tablet (CO1-3 mg) (see formulation in Table 2B) provides a rapid dissolution in vitro since about 60% of DRSP initially present in tablets were released within 30 min according to the USP XXIII Paddle Method (see curve no. 3, FIG. 2).

TABLE 2B

Composition of tablets CO1-3 mg

| Material | mg/tablet | (%) |
|---|---|---|
| Drospirenone | 3.0 | 4.69 |
| Pregelatinized Starch, NF | 12.77 | 19.95 |
| Lactose monohydrate, NF | 36.48 | 56.99 |
| Corn Starch, NF | 7.56 | 11.81 |
| Povidone K30, NF | 3.36 | 5.25 |
| Polysorbate 80, NF | 0.50 | 0.79 |
| Vegetal Magnesium Stearate, NF | 0.33 | 0.52 |
| TOTAL | 64.00 | 100 |

The second type of tablet (CO2-3 mg) (see formulation in Table 2C) displays a very low dissolution rate of DRSP in vitro. No more than of about 5% of DRSP initially present in tablets were released within 30 min and no more than about 40% of the DRSP was dissolved within 4 hours (see curve no1, FIG. 2).

TABLE 2C

Composition of tablets CO2-3 mg

| Material | mg/tablet | (%) |
|---|---|---|
| Drospirenone | 3.0 | 4.74 |
| Anhydrous Lactose, NF | 13.83 | 21.84 |
| Microcrystalline cellulose, NF | 36.48 | 57.60 |
| Hydroxypropylmethyl cellulose, NF (low molecular weight) | 6.33 | 10.00 |
| Colloidal silicon dioxide, NF | 3.36 | 5.31 |
| Vegetal Magnesium Stearate, NF | 0.33 | 0.53 |
| TOTAL | 63.33 | 100 |

Example 3

Pharmacokinetic Studies

Part 1: Evaluation of the Pharmacokinetics Parameters for the Composition According to an Embodiment (Tablet A-3 Mg) as Compared to Yasminelle®

Objectives:

The main objective of the present trial was to assess the bioavailability of an oral test preparation containing drospirenone at 3.0 mg (tablets described in Example 1 obtained from batch 080053 (i.e. A-3 mg), called hereunder "test product" hereunder) as compared to a market standard (Yasminelle®, Schering AG, called hereunder "reference product") after oral administration of a single dose of drospirenone at 3.0 mg under fasting conditions in two different periods, 7 days apart. Yasminelle® comprises 3.0 mg DRSP in micronized form and 0.030 mg of ethinylestradiol.

In order to investigate the relative bioavailability of the products, the 90% confidence intervals for the intra-individual ratios (test vs. reference) for the endpoint(s) (AUC$_{0h\text{-}tlast}$ and C$_{max}$ of drospirenone) were determined.

The secondary objective of the present trial was to investigate the safety of both preparations on the basis of safety clinical and laboratory examinations (at the beginning and at the end of the trial) and registration of adverse events and/or adverse drug reactions.

Methodology:

The study was conducted as a monocentric, open, randomized, single-dose, two-period crossover trial in healthy female volunteers, with duration of hospitalization of approximately 12 h-13 h after dosing on day 1 and with a real wash-out period of 7 days.

Subjects (Planned and Analyzed):
    Planned for completion: 10
    Enrolled: 19
    Screened only: 5
    Randomized: 14
    Drop-outs: 0
    Completed as per protocol: 14
    Data set for pharmacokinetic analysis: 14
    Data set for statistical analysis: 14
    Data set for safety analysis: 14

Diagnosis and Main Criteria for Inclusion:
    [1] female Caucasian
    [2] age between 18 and 40 years
    [3] physically and mentally healthy as judged by means of a medical, standard laboratory and gynecological examination
    [4] non-smokers since at least 6 months (confirmed by urine cotinine test)
    [5] use of an effective non-hormonal method of contraception List of Accepted Contraceptive Methods
    Combination of two barrier methods (female/male condoms, diaphragms, spermicides)
        Intrauterine device (inert or copper-releasing IUD)
        Existing sterilization (female tubal occlusion)

Duration of Treatment:

Each volunteer received in a random way an oral single dose of 1 tablet of the test product or 1 of the reference drug on two single occasions, always under fasting conditions. Both study periods were separated by a real wash-out phase of at least 7 days.

Blood Sampling Points in Each Study Period:
    Pre-dose, and 0:30, 1:00, 1:30, 2:00, 3:00, 4:00, 5:00, 6:00, 8:00, 12:00, 24:00, 48:00 and 72:00 hours post dosing with separation of plasma. For each endpoint, the quantification of DRSP in plasma was performed according to an analytical method adapted from Kirk et al., (Rapid Communications in Mass Spectrometry, 2006, 20:1247-1252).

Briefly, Drospirenone was extracted from human EDTA plasma using a solid-phase extraction procedure with HLB 60 mg Oasis cartridges and afterwards derivatized with Girard-P solution, then injected into a liquid chromatograph equipped with a tandem mass spectrometry detector. This method enables the determination of drospirenone in human EDTA plasma over the range 0.25 to 100.40 ng/mL.

Criteria for Evaluation:
    Pharmacokinetics:
        Primary endpoints: AUC$_{0h\text{-}tlast}$ and C$_{max}$ of drospirenone
        Secondary endpoint: t$_{max}$ of drospirenone
        Additional endpoints: not planned
    Safety
        Adverse events, clinical and laboratory screening parameters.

Statistical Methods:
    For pharmacokinetic Endpoints:
        parametric method (ANOVA-log) for AUC$_{0h\text{-}tlast}$ and C$_{max}$ of drospirenone
        covariates in the model: sequence, treatment, period, volunteer within sequence
        non-parametric method (Hauschke et al. 1990) t$_{max}$ of drospirenone
    90% confidence interval for the ratios (test vs. reference) for AUC$_{0h\text{-}tlast}$ and C$_{max}$ of drospirenone
    For Evaluation of Safety:
        descriptive statistical evaluation only.

Bioavailability:

The 90% confidence intervals of log-transformed values were calculated for the intra-individual ratio test vs. reference for AUC$_{0h\text{-}tlast}$ and C$_{max}$ of drospirenone (and then only interpreted in a descriptive way, and not compared with the usual acceptance ranges for the respective parameters (CPMP/EWP/QWP/1401/98, July 2001) as the current trial did not have the aim of proving bioequivalence). The 90% confidence interval was calculated for the intra-individual ratio for the difference of t$_{max}$ (test-reference) and descriptively assessed.

Results

Pharmacokinetics

A total number of 14 volunteers completed the trial according to the protocol. The samples of 14 volunteers were analyzed and 14 volunteers were subjected to statistical evaluation. The endpoints of the analysis of drospirenone after an oral single dose of 1 tablet (drospirenone 3.0 mg) of the test preparation or 1 film-coated tablet (0.03 mg ethinyl estradiol and 3 mg drospirenone) of the reference product of the 14 volunteers who were subject to pharmacokinetic and statistical evaluation are summarized in Table 3 hereunder.

TABLE 3

Pharmacokinetic endpoints (primary, secondary, and additional) of drospirenone for test product (TEST) and reference product (REFERENCE).

| Variable | geom. mean | arithm. mean | SD | CV | range | median |
|---|---|---|---|---|---|---|
| TEST (N = 14) | | | | | | |
| AUC0-tlast [ng * h/mL] | 360.96 | 368.55 | 75.83 | 20.6 | 234.72-482.91 | 359.33 |
| AUC0-inf [ng * h/mL] | 452.93 | 462.00 | 93.26 | 20.2 | 312.60-624.14 | 463.65 |
| AUCres [%] | 19.12 | 20.04 | 6.62 | 33.0 | 12.13-33.70 | 17.70 |

TABLE 3-continued

Pharmacokinetic endpoints (primary, secondary, and additional) of drospirenone for test product (TEST) and reference product (REFERENCE).

| Variable | geom. mean | arithm. mean | SD | CV | range | median |
|---|---|---|---|---|---|---|
| Cmax [ng/mL] | 16.46 | 17.36 | 5.50 | 31.6 | 6.39-27.79 | 17.41 |
| tmax | — | 3.57 | 1.01 | 28.3 | 2.00-5.00 | 3.50 |
| MRT [h] | — | 44.08 | 9.69 | 22.0 | 33.64-64.18 | 40.89 |
| $t^{1/2}$ [h] | — | 31.87 | 6.29 | 19.7 | 24.59-44.43 | 29.42 |
| REFERENCE (N = 14) | | | | | | |
| AUC0-tlast [ng * h/mL] | 414.60 | 418.58 | 60.46 | 14.4 | 337.80-527.81 | 397.70 |
| AUC0-inf [ng * h/mL] | 503.65 | 509.25 | 77.76 | 15.3 | 386.08-654.48 | 510.74 |
| AUCres [%] | 17.12 | 17.58 | 4.18 | 23.8 | 11.19-27.61 | 18.47 |
| Cmax [ng/mL] | 34.91 | 35.43 | 6.32 | 17.8 | 24.30-45.96 | 35.24 |
| tmax | — | 1.57 | 0.55 | 35.0 | 1.00-3.00 | 1.50 |
| MRT [h] | — | 38.81 | 6.45 | 16.6 | 29.68-56.00 | 39.39 |
| $t^{1/2}$ [h] | — | 29.78 | 4.41 | 14.8 | 25.21-43.30 | 28.47 |

The 90% confidence intervals for the intra-individual ratios (test/reference) for $AUC_{0-tlast}$ Last and $C_{max}$ of drospirenone, as well as differences (test-reference) for $t_{max}$ of drospirenone are presented in table 4 hereunder.

Figure 3A:
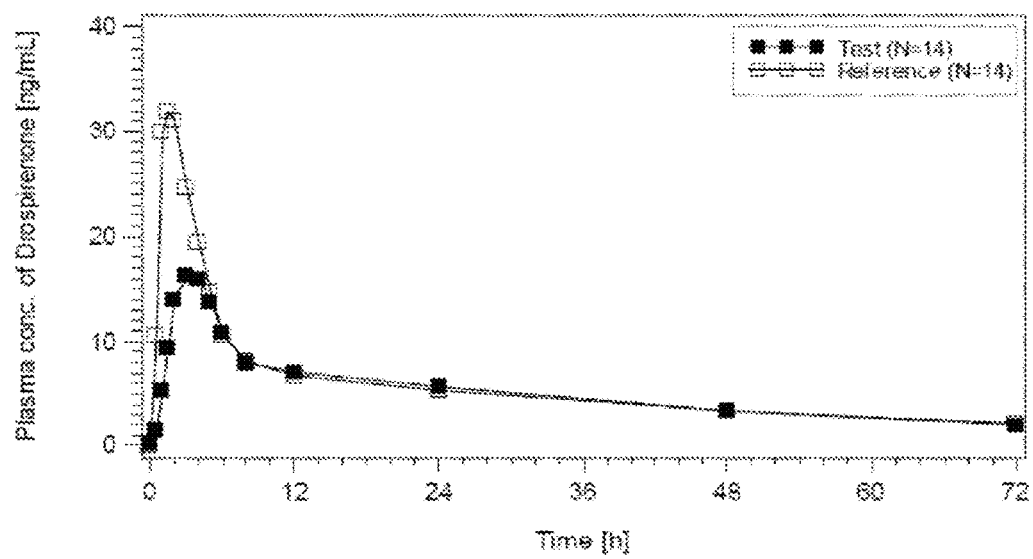
FIG. 3A and FIG. 3B: Mean Drospirenone Serum Concentration Versus Time Curves

The concentration-time curves of drospirenone after administration of an oral single dose of 1 tablet of the test preparation and tablet of the reference product are to be found in FIG. 3A for both preparations (arithmetic means).

The evaluation of bioavailability of the primary endpoints $AUC_{0-tlast}$ and $C_{max}$ of drospirenone was based on a parametric method (ANOVA-log).

The 90%-confidence interval calculated by means of ANOVA-log for the first primary endpoint, intra-individual ratio (T/R) of $AUC_{0-tlast}$ of was between 0.8081 and 0.9380. The 90%-confidence interval calculated by means of ANOVA log for the second primary endpoint intra-individual ratio (T/R) of $C_{max}$ of drospirenone was between 0.3930 and 0.5658. The secondary endpoint $t_{max}$ the 90%-confidence interval for the intra-individual differences was between 1.5000 and 2.5000 hours. The point estimator for the difference of $t_{max}$ of drospirenone was 106 minutes (the concentration maxima after administration of the test preparation being observed later).

Drospirenone isomerizes into a biologically inactive isomer in acidic conditions, including in the acidic conditions that are encountered in the human stomach.

When conducting the present pharmacokinetics study, assays for detecting the eventual presence of the inactive isomer of drospirenone in the plasma of the treated women have been performed. The results have shown that the amount of inactive isomer of drospirenone in the plasma samples collected from the clinically tested women subjects was below the detectable level (<1 ng/ml), which means that the pharmaceutical composition that has been used is adapted to release the full amount of drospirenone in its biologically active form to the target organs.

Safety:

The test formulation and the reference drug were well tolerated. Seventeen non-serious adverse events (AEs) were registered in 11 subjects in the course of the trial:

Nine AEs were observed in 8 subjects after administration of test product.

Eight AEs were observed in 7 subjects after administration of reference drug.

All adverse events were assessed as not serious. All adverse events were assessed as possibly related by the investigator. All AEs resolved completely within relative short frame time. The results of laboratory screening gave no indications for adverse events or adverse drug reactions.

Conclusions

Based on the $AUC_{0-tlast}$ of drospirenone, the extent of absorption of the test product is similar to that of the reference product, except that the rate of absorption is significantly delayed, resulting in an increased $t_{max}$ and decreased $C_{max}$. The tolerability of test product and the reference product was similarly good.

Part 2: Evaluation of Other Comparative Tablets CO1-3 Mg and CO2-3 Mg as Compared to Yasminelle®

The main objective of this second trial was to further illustrate the correlation between in vitro dissolution profile and pharmacokinetics parameters for oral tablets comprising DRSP. The oral test tablets were tablet CO1-3 mg and tablet CO2-3 mg which display a rapid in vitro dissolution rate for DRSP and a very slow dissolution rate for DRSP, respectively (see Example 2B).

The reference product was Yasminelle®. The methodology for this second trial was similar to that of the trial described in Part 1 above.

Briefly, the bioavailability of two oral test preparations (namely CO1-3 mg and CO2-3 mg) as compared to that of the market standard (Yasminelle®, Schering AG) was assessed after oral administration of a single tablet in each case (corresponding to 3 mg of DRSP) under fasting conditions in three different periods, 7 days apart. In order to investigate the relative bioavailability of the products, the 90% confidence intervals for the intra-individual ratios (CO1-3 mg vs. reference product and CO2-3 mg vs. reference product) for the endpoint(s) ($AUC_{0-tlast}$ and $C_{max}$ of drospirenone) was determined.

The study was conducted as a monocentric, open, randomized, single-dose, three-period crossover trial in healthy female volunteers, with a duration of hospitalization of approximately 12 h-13 h after dosing.

Each volunteer received randomly an oral single dose of drospirenone 3.0 mg (either 1 test tablet CO1-3 mg or 1 test tablet CO2-3 mg or 1 film-coated tablet of Yasminelle®) on three single occasions under fasting conditions.

The three study periods were separated by a real wash-out phase of between 7 days and 10 days.

Figure 3B:
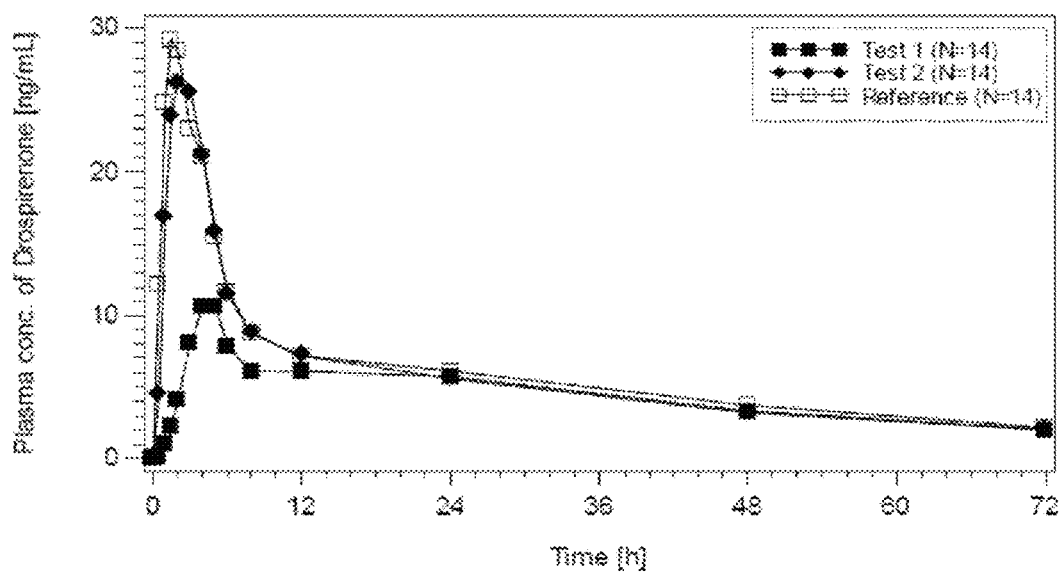

Subjects (Planned and Analyzed):
  Planned for completion: 10
  Enrolled: 18
  Screened only: 4
  Randomized: 14
  Drop-outs: 0
  Completed as per protocol: 14
  Data set for pharmacokinetic analysis: 14
  Data set for statistical analysis: 14
  Data set for safety analysis: 14
Results The concentration-time curves of drospirenone after administration of an oral single dose of 1 tablet of each product (namely, CO1-3 mg, CO2-3 mg and Yasminelle®) are in FIG. 3B (arithmetic means). As a reminder, CO1-3 mg displayed a rapid dissolution rate for DRSP in vitro (about 60% within 30 min). The pharmacokinetic profile obtained for CO1-3 mg is very close to that of Yasminelle® except for the $C_{max}$. Interestingly, the mean $C_{max}$ of CO1-3 mg was 30 ng/ml versus 36 ng/ml for Yasminelle®. The $AUC_{0h\text{-}tlast}$ for CO1-3 mg was similar to that of Yasminelle® (410.58 ng*h/ml versus 440.14 ng*h/ml).

On the other hand, CO2-3 mg surprisingly displays a very low dissolution rate of DRSP in vitro since no more than about 5% of DRSP initially present in tablets were released within 30 min and no more than about 40% of the DRSP was dissolved within about 4 hours. The composition displays a reduced $C_{max}$ and a delayed $t_{max}$ as compared to Yasminelle®. However, the mean AUC of said composition was low.

These pharmacokinetics results combined with in vitro results described in Example 2 illustrate the correlation between the in vitro dissolution rate of DRSP and its pharmacokinetics profile (in particular for $C_{max}$ and $t_{max}$), upon oral administration.

Example 4

Simulation Curves Based on Experimental Data Obtained in the Clinical Trial Described in Example 3, Part 1

The DRSP mean plasma concentration versus time curves, which is expected to be obtained from the oral administration of one tablet described in Table 2A but containing 4 mg of DRSP from batch 80053 (namely, A-4 mg), was extrapolated from experimental data obtained in the clinical trial described in Example 3, with the assumption that the DRSP plasma concentration is proportional to the administered oral amount of DRSP.

Figure 4A:
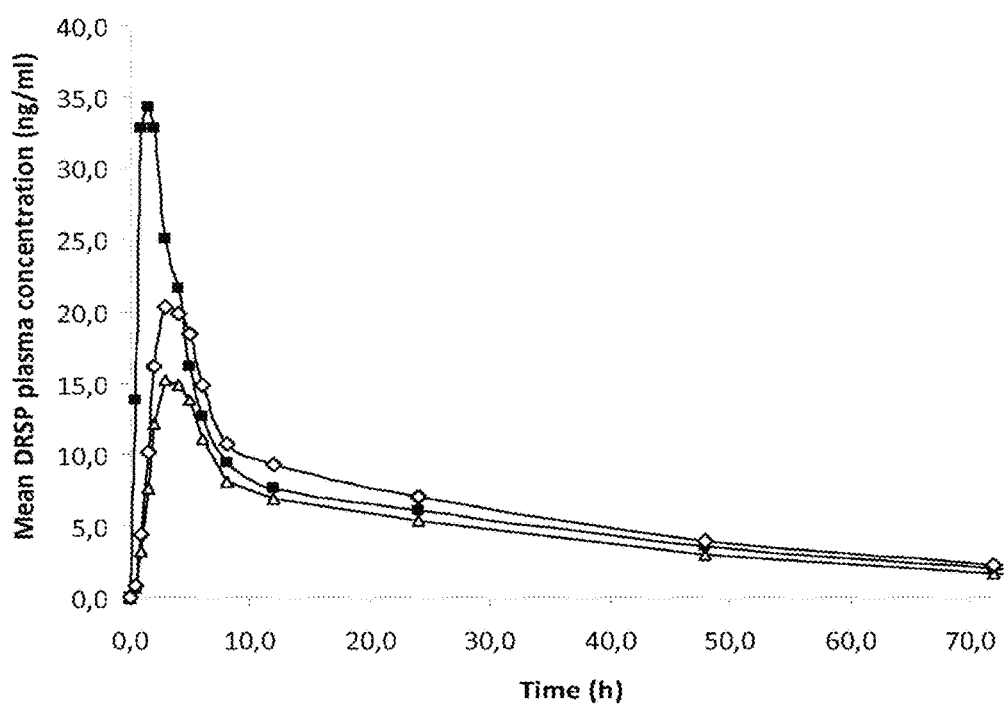
FIGS. 4A-4C Simulation Based on Pharmacokinetic Results from Clinical Trial Described in Example 3

The resulting curve for tablet A-4 mg is shown in FIG. 4A and FIG. 4A and compared with that obtained with Yasminelle® and with the tablet A-3 mg described in table 2A.

Figure 4B:
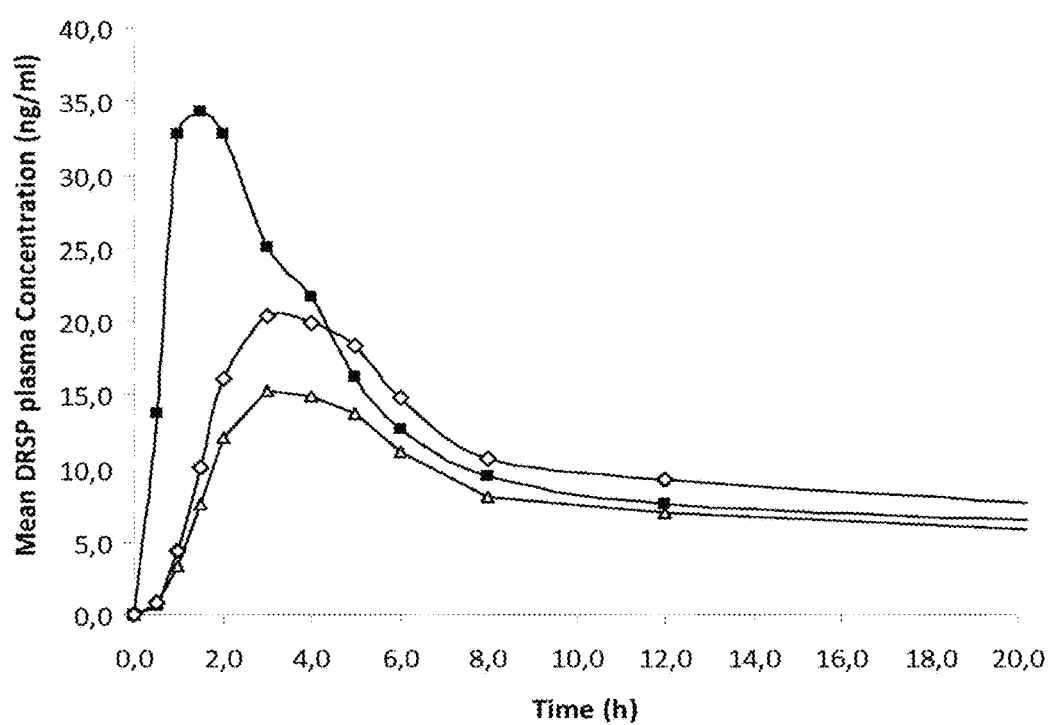

As illustrated in FIGS. 4A and 4B, increasing the DRSP amount from 3 mg to 4 mg in the tablet described in table 2A is expected not to modify the $t_{max}$, which may remain significantly delayed as compared to that of Yasminelle®. The $C_{max}$ is expected to be increased but to remain significantly lower than that of Yasminelle® (no more than 60% that of Yasminelle®). Interestingly, the mean plasma concentration is expected to be higher than that of Yasminelle® after the concentration peak.

Figure 4C:
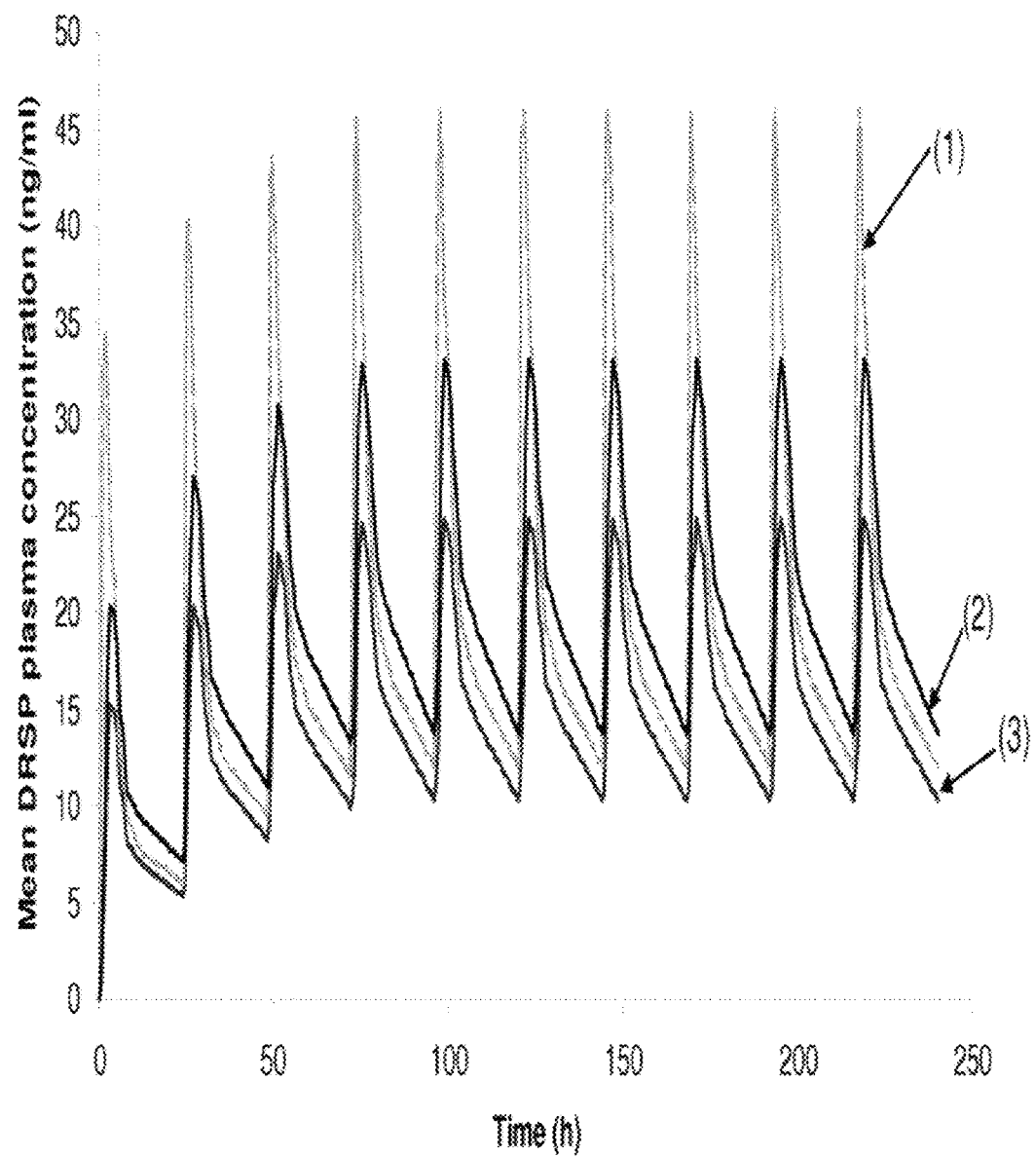

FIG. 4C shows the mean DRSP plasma concentration versus time curves which are expected to result from the repeated administration every 24 hours of one tablet of Yasminelle® (curve no1), one tablet of A-3 mg (curve no3) and one tablet of A-4 mg (curve no2).

The curves obtained for the compositions of one embodiment (namely curves no3 and no2) show less difference between mean $C_{max}$ and mean $C_{min}$ (minimal DRSP concentration) than the Yasminelle® composition. The repeated administration of the compositions of the embodiment thus provides a more stable DRSP plasma concentration with lower $C_{max}$ than Yasminelle®. Such a fact improves the bleeding profile and reduces the side effects of DRSP when the compositions of the embodiment are used as a contraceptive.

In the case of tablet A-4 mg, it should be noted that the mean plasma concentration is higher than that obtained of Yasminelle® for the time period between $t_{max}$ and the time of the next tablet intake, which provides a higher contraceptive reliability. Thus, Tablet A-4 mg is expected to be appropriate as a progestogen-only pill.

Example 5

Example of Composition According to Another Embodiment

Part 1: In Vitro Dissolution Profile

Tablets (B-4 mg) were prepared as described in Example 1 from DRSP batch No PR100003. Each tablet comprises 4.0 mg of DRSP and excipients in a similar amount to that described in Table 2A. The tablets (B-4 mg) were further coated with a suitable film-forming agent, as described in the specification.

Figure 5A:
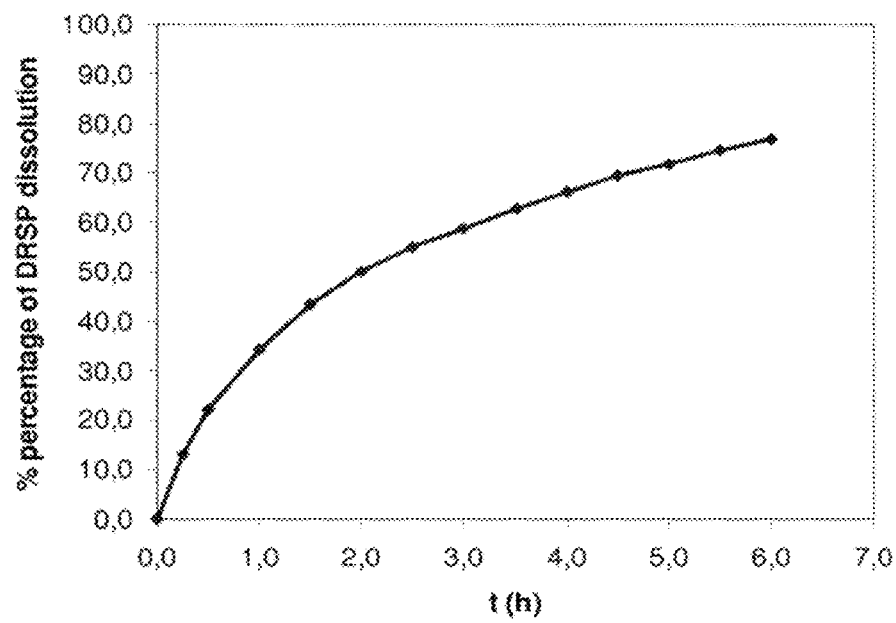
FIGS. 5A-5B: In vitro Dissolution Profile and Mean Drospirenone Serum Concentration Versus Time Curve for Tablet Comprising 4 mg of DRSP (B-4 mg).

The resulting tablets were subjected to a dissolving in vitro test as described in Example 2. The mean in vitro dissolution profile of said tablets is shown in FIG. 5A.

The initial dissolution rate for DRSP was significantly reduced as compared to Yasminelle® since only about 22% of DRSP initially present in tablets were released within 30 min. However, about 66% and about 77% of DRSP initially present in tablets were released within 4 h and 6 h respectively.

The in vitro dissolution profile for tablets B-4 mg was similar to that of tablet A-3 mg (see example 2). Such a fact illustrates that the specific area of DRSP does not significantly impair its in vitro dissolution if the DRSP displays appropriate d50, d90 and d10.

Part 2: Evaluation of the Pharmacokinetics Parameters for the Composition According to Another Embodiment (Tablet B-4 Mg) as Compared to Yasminelle®
a. Methodology The pharmacokinetics parameters for tablet B-4 mg were determined as described above.

Briefly, the bioavailability of the test preparation (namely B-4 mg) as compared to that of the market standard (Yasminelle®, Schering AG) was assessed after oral administration of a single tablet in each case under fasting conditions in three different periods, 7 days apart.

The DRSP oral dose was 3 mg for Yasminelle® versus 4 mg for tablet B-4 mg (inventive). In order to investigate the relative bioavailability of the products, the 90% confidence intervals for the intra-individual ratios (B-4 mg versus Yasminelle®) for the endpoint(s) ($AUC_{0\text{-}tlast}$ and $C_{max}$ of drospirenone) were determined.

The study was conducted as a monocentric, open, randomized, single-dose, three-period crossover trial in healthy female volunteers, with duration of hospitalization of approximately 12 h-13 h after dosing.

Each volunteer randomly received an oral single dose of drospirenone (either one test tablet B-4 mg or one tablet of Yasminelle®) on two single occasions under fasting conditions. Both study periods were separated by a real wash-out phase of between 7 days and 10 days.

Subjects (Planned and Analyzed):
Planned for completion: 10
Enrolled: 15
Screened only: 5
Randomized: 10
Drop-outs: 0
Completed as per protocol: 10
Data set for pharmacokinetic analysis: 10
Data set for statistical analysis: 10
Data set for safety analysis: 10 b. Results

Yasminelle® and the test product were well-tolerated by all the patients.

Figure 5B:
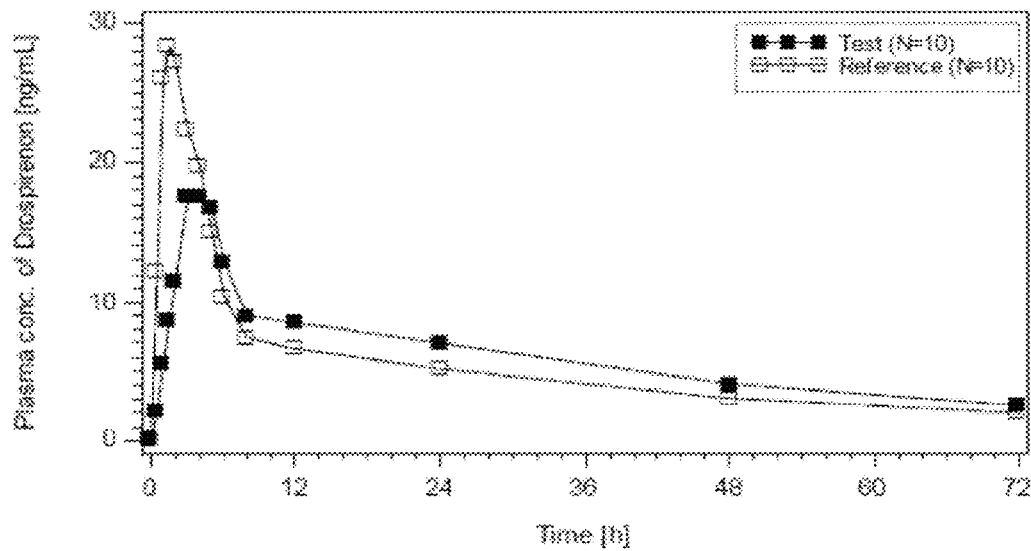

The concentration-time curves of drospirenone after administration of an oral single dose of 1 tablet of each product (namely, tablet B-4 mg and Yasminelle®) are to be found in FIG. 5B (arithmetic means). The results of said trial are further shown in table 5 hereunder.

TABLE 5

Pharmacokinetic endpoints of drospirenone for tablet B-4 mg (TEST) and Yasminelle ® (REFERENCE)

| Variable | geom. mean | arithm. mean | SD | CV | range | median |
|---|---|---|---|---|---|---|
| | | TEST (N = 10) | | | | |
| AUC0-tlast [ng * h/mL] | 428.07 | 438.85 | 104.53 | 23.8 | 320.74-634.58 | 419.05 |
| Cmax [ng/mL] | 18.96 | 19.81 | 6.14 | 31.0 | 12.42-30.17 | 19.40 |
| tmax [h] | — | 3.900 | 0.876 | 22.5 | 3.000-5.000 | 4.000 |
| | | REFERENCE (N = 10) | | | | |
| AUC0-tlast [ng * h/mL] | 386.68 | 394.88 | 90.22 | 22.8 | 271.57-615.65 | 391.49 |
| Cmax [ng/mL] | 32.52 | 32.85 | 4.85 | 14.8 | 23.97-42.80 | 33.39 |
| tmax [h] | — | 1.700 | 0.979 | 54.1 | 1.000-4.000 | 1.500 |

The pharmacokinetics profile for DRSP obtained after the oral administration of one tablet B-4 mg correlated with the DRSP pharmacokinetics profile expected on the basis of simulations (see Example 4).

The mean $t_{max}$ for tablet B-4 mg was significantly delayed as compared to that of Yasminelle® (3.9 h versus 1.7 h). Furthermore, the mean $C_{max}$ obtained for tablet B-4 mg was significantly lower than that of Yasminelle® (19.8 versus 32.9 ng*h/ml). The mean $C_{max}$ for tablet B-4 mg corresponded to about 58% of Yasminelle® $C_{max}$ whereas, in Example 1, the mean $C_{max}$ for tablet A-3 mg corresponded to 49% of that of Yasminelle®. The increase of DRSP dose in tablets did not induce a significant change in mean $C_{max}$ values.

On the other hand, the increase of DRSP dose significantly improved the mean $AUC_{0h-tlast}$ since the mean $AUC_{0h-tlast}$ for tablet B-4 mg was 111% of Yasminelle. In Example 1, the mean $AUC_{0h-tlast}$ for tablet A-3 mg was only 86% of that of Yasminelle®.

In other words, the present results clearly show that compositions of the embodiment allow for a high value of mean $AUC_{0h-tlast}$ combined with a low mean $C_{max}$ and a delayed mean $t_{max}$ for DRSP, as compared to Yasminelle®. The repeated administration of tablets B-4 mg every 24 hours will certainly provide a DRSP plasma concentration profile similar to that expected for tablet A-4 mg (see FIG. 4C, curve no2).

Accordingly, the compositions of the present embodiment, such as tablet A-4 mg and tablet B-4 mg, are appropriate to be used as contraceptive-only pills. Such contraceptives have a good tolerance and to prevent the occurrence of side-effects related to high and fluctuated DRSP plasma concentrations.

Part 3: Evaluation of the Contraceptive Efficiency of the Pharmaceutical Composition According to Another Embodiment The aim of the study is to illustrate that a contraceptive pill according to the embodiment which comprises DRSP as the sole active contraceptive drug and which is administered upon a 24/4 regimen allows for the inhibition of ovulation even in the case of episodic delay of administering the pill.

The contraceptive pill is made of 24 tablets B-4 mg as defined in Example 5, Part 2 above and 4 placebo tablets.

a. Methodology.

The study was an open-label monocentric trial. Subjects eligible for the study were aged 20-30 years, had a body mass index <30 kg/m², regular menstrual cycles (at least 4 regular cycles in the past 6 months) and were willing to use condoms during the entire duration of the study. Excluded were subjects with a (suspected) pregnancy, active or past thromboembolic disorder, present or past severe hepatic disease, carcinoma of the endometrium or other known or suspected estrogen-dependent neoplasia, undiagnosed vaginal bleeding, use of liver enzyme-inducing drugs and other drugs.

A total of 20 women were enrolled in this trial and performed the two treatment cycles and the follow-up cycle.

TABLE 6

Parameters of enrolled patients

| | Age | Weight (kg) | BMI (Kg/m²) | Systolic blood pressure (mmHg) | Diatolic blood pressure (mmHg) | Heart rate (beats/Him) |
|---|---|---|---|---|---|---|
| Mean ± Std dev | 24.6 ± 2.4 | 60.28 ± 7.95 | 22.76 3.19 | 110.3 ± 10.3 | 64.1 ± 7.0 | 65.4 ± 5.7 |

TABLE 6-continued

Parameters of enrolled patients

|  | Age | Weight (kg) | BMI (Kg/m$^2$) | Systolic blood pressure (mmHg) | Diatolic blood pressure (mmHg) | Heart rate (beats/Him) |
|---|---|---|---|---|---|---|
| Median | 24.5 | 59.1 | 22.39 | 115.0 | 62.5 | 64.0 |
| Min, Max | 20; 29 | 50.0; 79.2 | 18.1; 30.0 | 90; 120 | 50; 80 | 58; 80 |

The subjects received daily treatment with tablets containing about 4 mg DRSP with a 24/4 regimen during two treatment cycles. The subjects started treatment on the 1st day of the cycle (i.e., the first day of onset of vaginal bleeding) following the screening visit. The subjects took one tablet of about 4 mg DRSP from day 1 to day 24 and one placebo tablet from day 25 to day 28 of each treatment cycle at a fixed hour, with the exception of day 5 and day 13 of the second treatment cycle. On these two days, the tablet intake was delayed for 24 hours (i.e., no pill was taken on day 5 and day 13 and a tablet was taken once on day 6 and once on day 14, respectively). The complete study consisted of a 56-day treatment period and a 28-day post-treatment follow-up period. After informed consent was obtained, the subjects underwent a gynecological examination and a general medical examination, including 12-lead ECG, hematology, biochemistry and urinalysis laboratory tests. After compliance with the eligibility criteria was confirmed, and after performing a urine pregnancy test with a negative result on the first day of onset of vaginal bleeding, the subject was included in the study and began taking the study medication.

Blood sampling for hormonal determination (progesterone, 17-beta-estradiol, FSH and LH) was performed every 3 days from day 1 to day 84 and assessments of weight, blood pressure and heart rate were performed at each visit. Serum progesterone, 17-beta-estradiol, FSH and LH concentrations were measured with validated commercial in vitro diagnostic kits (V1DAS, ELFA Biomerieux). Internal controls were included in each set of samples.

Two urine pregnancy tests were performed during the study:

At the visit on day 1 of the first cycle in order to verify the exclusion criterion "pregnant woman" just before starting the study treatment (the subject was to be excluded if this test was positive); and At the visit on day 7 of the follow-up cycle.

The occurrence of ovulation during treatment was determined on the basis of serum progesterone concentration, using the criteria of Landgren et al. Thus, an ovulation was judged to have occurred in case of progesterone concentrations >5.04 ng/ml-sustained for at least 2 consecutive progesterone samples.

b. Results

FIGS. 6A and 6B show the plotted individual values for plasma progesterone levels and plasma estradiol levels, respectively. For all women, progesterone level values were systematically lower than 5.04 ng/ml during the entire treatment period (including placebo period). The maximum value of progesterone was observed to be 3 ng/mL for a sole woman and for only one time during the treatment periods (including placebo period).

These results surprisingly show that during the 2 treatment cycles, no ovulation occurred. Conversely, upon cessation of treatment, during the 28-day follow-up cycle, the progesterone levels increased above 5.04 ng/mL in 17 out of 20 women showing a return of ovulation. The minimum time to the first level of progesterone to be above 5.04 ng/mL was on day 15 after the last placebo tablet.

During the 2 treatment cycles, the mean estradiol levels were significantly lower in comparison with those measured during the follow-up cycle. Noticeably, the secretion of estradiol is not totally inhibited during the treatment period.

To conclude, the data surprisingly demonstrate that the compositions of the embodiment, when used as a POC upon a 24/4 regimen, provided reliable inhibition of ovulation even in the presence of a placebo period. This ovulation inhibition was maintained even if the intake of the tablet was delayed for 24 hours in two separate times within one treatment cycle.

In view of these experimental data, the compositions of the present embodiment exhibit similar reliability and efficiency as traditional combined pill such as Yasmine®, but with less side-effects, for example, on the cardiovascular system.

Example 6

Example Composition According to Another Embodiment

Tablets comprising about 4 mg of drospirenone (C-4 mg) are prepared by direct compression. The composition of tablets is described hereunder.

TABLE 7

Composition of tablets (C-4 mg)

| Material | mg/tablet |
|---|---|
| Drospirenone (PR100311) | 4.00 |
| Microcrystalline cellulose PH102 | 33.02 |
| Anhydrous lactose PS = 20%, <45 µm | 17.50 |
| Silicon dioxide | 0.29 |
| Magnesium stearate | 0.33 |
| Coating (Opadry II 85F18422 white) | 1.65 |
| TOTAL | 56.75 |

DRSP batch PR100311 is characterized by a specific area of 0.66 m$^2$/g. The in vitro dissolution rate and the pharmacokinetic parameters for these tablets were determined as described in Example 2 and Example 3, respectively.

TABLE 8

In vitro DRSP dissolution rate and DRSP pharmacokinetic profile for tablets C-4 mg

| In vitro Dissolution | % of DRSP dissolved within 30 min | 45.8 |
|---|---|---|
|  | % of DRSP dissolved within 4 h | 88.3 |
| Pharmacokinetics | Mean $C_{max}$ (ng/ml) | 26 |
|  | Mean $t_{max}$ (h) | 3.6 |
|  | Mean $AUC_{0-tlast}$ (ng*h/mL) | 643 |

Example 7

LF111 (DRSP) Treatment Decreases the Number of Days with Bleeding and/or Spotting 1. Objectives The study CF111/302 below represents a pivotal, multi-center, double-blind, double-dummy, randomized trial on the contraceptive efficacy, tolerability and safety of LF111 (DRSP) over 9 treatment cycles of 28 days of treatment (24 active test product tablets followed by 4 days of placebo tablets).

The first objective is to demonstrate the contraceptive efficacy of LF111 and the second objective is to demonstrate the safety and tolerability of LF111, particularly with respect to the patient's bleeding pattern.

2. Materials and Methods a. Test Product, Doses and Mode of Administration

LF111 film-coated tablets (test product; 24 tablets containing about 4 mg DRSP followed by 4 placebo tablets; León Farma) were orally administered during this trial. Each LF111 tablet included the following:

|  | Ingredient | mg/tablet |
|---|---|---|
| Active ingredient | Drospirenone[1] | 4.00 |
| Excipient | Microcrystalline cellulose | 33.02 |
|  | Lactose, anhydrous | 17.50 |
|  | Silica, colloidal anhydrous | 0.29 |
|  | Magnesium stearate | 0.29 |
|  | White coating system | 1.65 |
|  | Total | 56.75 |

[1]crystallized and non-micronized drospirenone, prepared according to the process similar to that described in WO 2006/061309.

b. Trial Design

This prospective, multicenter, randomized, double-blind, double-dummy trial is conducted on 857 women without uncontrolled current diseases, at risk of pregnancy, at the age of 18-45 years, systolic blood pressure <140 mmHg, diastolic blood pressure <90 mmHg followed in approximately 73 centres in Austria, Czech Republic, Germany, Hungary, Poland, Romania, Slovakia and Spain.

After providing informed consent at visit 1a (screening V1a) and receiving study medication at visit 1b, subjects will attend visits 2 to 4 at day 24±2 of the $1^{st}$, $3^{rd}$, and $6^{th}$ treatment cycle, and visit 5 (V5) at day 29+2 of the $9^{th}$ treatment cycle. The follow-up (visit 6, V6) will take place 7-10 days after last LF111 intake.

The planned total duration of the trial was set to be 16 months, with a maximum of 6 months for the enrolment process, a maximum of 9 months for the contraceptive treatment per se and 10 days for the follow-up step. The duration of contraceptive treatment for the individual women is 9×28 days.

c. Exclusion Criteria

Pregnant subject; Breast-feeding subject; Subject is known to or suspected of not being able to comply with the study protocol and the use of the IMPs (Investigational Medicinal Products); Abnormal finding on pelvic, breast or intravaginal ultrasound examination that precludes participation in the trial; Unexplained amenorrhoea, known polycystic ovary syndrome; Subject having ASC-US or more severe finding on Pap smear; Known contraindication or hypersensitivity to the active ingredients (drospirenone) or excipients of IMPs (cellulose, lactose, silicon dioxide, magnesium stearate, corn starch, polyethylene glycol, polyvinyl pyrrolidone, polyvinyl alcohol, aquarius BT16035 cottage green, talc, titanium dioxide; silica colloidal anhydrous, all-rac-α-tocopherol, lactose, monohydrate, maize starch, povidone, stearic acid, hypromellose, macrogol 400); Significant cardiovascular, hepatic or renal disease, diabetes with vascular involvement, uncontrolled thyroid disorder or current venous thrombosis or embolism; Undiagnosed vaginal bleeding; Known or suspected sex-steroid sensitive malignancies; Presence or history of severe hepatic disease as long as liver function values have not returned to normal; Evidence or history of alcohol, medication or drug abuse (within the last 12 months); Known bleeding disorder or history of unexplained bleeding or bruising within the last 12 months prior to V1a; Prohibited previous medication/contraceptives (injectable hormonal methods of contraception within the last 6 months before V1a, progestin-releasing IUD (intrauterine device) or contraceptive implant within the last 2 months before V1a, anti-retroviral therapy within the last 6 months before V1a, microsomal enzyme-inducing drugs within the last 28 days before the start of IMP intake); Dependence on prohibited co-medication (estrogens, progestogens, activated charcoal, microsomal enzyme-inducing drugs, anticonvulsants [e.g. hydantoins, phenytoin, carbamazepine, oxcarbazepine, topiramate, felbarnate, primidone], barbiturates, antibiotics [such as rifabutin or rifampicin], ritonavir, nelfinavir, atorvastatin, bosentan, griseoulvin, phenylbutazon, St. John's wort [hypericum perforatum], medications that may increase serum potassium [ACE inhibitors, angiotensin—H receptor antagonists, potassium-sparing diuretics, potassium supplementation, heparin, aldosterone antagonists and NSAIDs]); Planned surgery during the anticipated time of participation in this trial requiring withdrawal of an oral contraceptive; Regular concomitant use of barrier contraceptive methods, spermicides, IUDs or other contraceptive measures (excepting occasional use due to risk of infection); Evidence or history of neurotic personality, psychiatric illness or suicide; Participation in another trial of investigational drugs or devices parallel to, or less than 90 days before trial entry, or previous participation in this trial; Employee of the investigator or trial centre, or family member of the employees or the investigator; Any condition that, in the opinion of the investigator, may jeopardise the trial conduct according to the protocol.

d. Criteria for Evaluation d.1. Efficacy

Primary: Overall Pearl Index (overall PI);

Secondary: PI for method failures; PI after correction for back-up contraception;

Pregnancy ratio.

d.2. Safety/Tolerability

Proportion of subjects with unscheduled bleeding in treatment cycles 2 to 6; Proportion of subjects with unscheduled bleeding in each treatment cycle from treatment cycles 2 to 9 and cumulative in treatment cycles 2 to 6 and treatment cycles 2 to 9; Number of days of bleeding/spotting during treatment cycles 2 to 4; Number of days of bleeding/spotting during treatment cycles 7 to 9; Number of days of bleeding/spotting during treatment cycles 2 to 9; Number of bleeding/spotting episodes during treatment cycles 2 to 4; Number of bleeding/spotting episodes during treatment cycles 7 to 9; Number of bleeding/spotting episodes during treatment cycles 2 to 9; Proportion of subjects with amenorrhoea; Change in body weight from baseline (V1a); Change in systolic and diastolic blood pressure from baseline (V1a); Adverse Events (AEs); Pulse rate; Electrocardiogram (ECG) for a subset of subjects; Clinical laboratory parameters;

Special clinical laboratory parameters (haemostatic variables, carbohydrate metabolism and bone metabolism) for a subset of subjects.

d.3. Statistical Methods d.3.1. Efficacy Parameters

Analysis of the primary efficacy variable defined as overall PI will be performed for the Full Analysis Set (FAS) and the Per Protocol Set (PPS). Primary assessment of efficacy will be based on the FAS. Two-sided 95% confidence interval (CI) for overall PI will be calculated assuming that events of pregnancy have a Poisson distribution. Secondary efficacy analysis will be based on the FAS. Two-sided 95% CIs will be calculated for the method failures PI. The Clopper-Pearson 95% confidence interval will be calculated for the pregnancy ratio. The cumulative pregnancy rate will be calculated using the Kaplan Meier estimator. Two sided 95% CI will be calculated for the PI after correction for back-up contraception.

d.3.2. Safety and Tolerability Parameters

Analysis of the parameters blood pressure, body weight, and bleeding pattern will be based on FAS. Analysis of safety endpoints will be conducted using the Safety Set only. All adverse events (AEs) and treatment-emergent adverse events (TEAEs) will be summarised by calculating the number and percent of subjects with AES by preferred term and system organ class. Also TEAEs will be summarised by severity and relationship to treatment. Number and percent of TEAES leading to study termination will be provided. Laboratory parameters, pulse rate and abnormal ECG results (e.g. QT prolongation) will be summarised by calculating summary statistics on the absolute values and on the change from V1a (special laboratory parameters and ECG: V1b) to V3, V4 and V5. Shift tables will be provided to illustrate changes with respect to the laboratory normal ranges between V1a and V5 (or EDV). The number and percent of subjects with values outside the limits of clinical significance will be summarized.

Results

As shown in Table 9 below, there is a significant reduction in the number of days with bleeding events per treatment cycle in women with excess weight (BMI of about 25 kg/m$^2$ or more) undergoing DRSP treatment as compared to women without excess weight (BMI of about 24.9 kg/m$^2$ or less) undergoing the same DRSP treatment.

TABLE 9

Number of days with bleeding events per treatment cycle by period of treatment cycles for a cohort of women with excess weight, as compared with a cohort of women without excess weight, undergoing DRSP treatment.

| Treatment cycle | | BMI ≤ 24.9 kg/m$^2$ (N = 660) | % per treatment cycle | BMI ≥ 25 kg/m$^2$ (N = 198) | % per treatment cycle | Total (N = 858) | Wilcoxon-rank-sum-test p value |
|---|---|---|---|---|---|---|---|
| Cycles 2-4 | n | 401 | | 126 | | 527 | |
| | Mean (SD) | 13.8 (12.84) | 16.4% | 10.7 (13.46) | 12.7% | 13.1 (13.05) | 0.0007 |
| | Median | 11.0 | | 6.0 | | 10.0 | |
| | Min/Max | 0/60 | | 0/66 | | 0/66 | |
| Cycles 2-6 | n | 315 | | 107 | | 422 | |
| | Mean (SD) | 20.6 (18.62) | 14.7% | 14.9 (18.64) | 10.6% | 19.1 (18.77) | 0.0005 |
| | Median | 17.0 | | 7.0 | | 14.0 | |
| | Min/Max | 0/100 | | 0/89 | | 0/100 | |
| Cycles 2-9 | n | 221 | | 84 | | 305 | |
| | Mean (SD) | 32.1 (27.85) | 14.3% | 22.2 (26.65) | 9.9% | 29.4 (27.84) | 0.0010 |
| | Median | 26.0 | | 13.5 | | 21.0 | |
| | Min/Max | 0/109 | | 0/106 | | 0/109 | |
| Cycles 5-7 | n | 315 | | 108 | | 423 | |
| | Mean (SD) | 10.8 (11.13) | 12.8% | 8.3 (10.98) | 9.9% | 10.2 (11.13) | 0.0053 |
| | Median | 7.0 | | 4.0 | | 6.0 | |
| | Min/Max | 0/67 | | 0/49 | | 0/67 | |
| Cycles 7-9 | n | 280 | | 94 | | 374 | |
| | Mean (SD) | 10.2 (10.10) | 12.1% | 7.9 (11.09) | 9.4% | 9.7 (10.39) | 0.0040 |
| | Median | 8.0 | | 3.5 | | 6.0 | |
| | Min/Max | 0/60 | | 0/55 | | 0/60 | |

N: Number of subjects in the Test group in the particular BMI group
n: Number of subjects with data available
SD: Standard deviation Table 9 provides that the number of days bleeding events in women with excess weight, i.e., women having a BMI of about 25 kg/m$^2$ or more, who are treated with the DRSP-based POC formulation (LF111) and women without excess weight, i.e., women having a BMI of about 24.9 kg/m$^2$ or less, who are also treated with LF111. The mean number of days of bleeding events per treatment cycles in women with excess weight is:

(i) reduced by about 22.5% as compared to women without excess weight subjected to the same contraceptive treatment during the treatment cycles 2-4;

(ii) reduced by about 27.7% as compared to women without excess weight subjected to the same contraceptive treatment during treatment cycles 2-6;

(iii) reduced by about 30.8% as compared to women without excess weight subjected to the same contraceptive treatment during the treatment cycles 2-9;

(iv) reduced by about 23.1% as compared to women without excess weight subjected to the same contraceptive treatment during the treatment cycles 5-7;

(v) reduced by about 22.5% as compared to women without excess weight subjected to the same contraceptive treatment during cycles 7-9.

The differences observed are statistically significant (p<0.01) using the Wilcoxon-rank sum test.

Each treatment cycle has 28 days and both groups of women (BMI≤24.9 kg/m² and BMI≥25 kg/m²) were administered a single daily dosage unit of LF111 for 24 days followed by 4 days of placebo tablets. As can be seen from the data presented in Table 9, the percentage of days of bleeding events in women with excess weight over a 28 day treatment cycle ranges from about 9.4% to about 12.7%, as compared to the percentage of days of bleeding events in women with no excess weight, which ranges from about 12.1% to about 16.4%.

As shown in Table 10 below, there is a significant reduction in the number of days with bleeding events in obese women (BMI of 30 kg/m² or more) undergoing DRSP treatment as compared with non-obese women (BMI of 29.9 kg/m² or less) undergoing the same DRSP treatment.

(iii) reduced by about 69.7% as compared to non-obese women subjected to the same contraceptive treatment during the treatment cycles 2-9;
(iv) reduced by about 48.1% as compared to non-obese women subjected to the same contraceptive treatment during the treatment cycles 5-9; and
(v) reduced by about 62.0% as compared to non-obese women subjected to the same contraceptive treatment during the treatment cycles 7-9.

The differences observed are statistically significant (p<0.05) using the Wilcoxon-rank sum test.

Each treatment cycle comprises 28 days and both groups of women (BMI≤29.9 kg/m² and BMI≥30 kg/m²) were administered a single daily dosage unit of LF111 for 24 days followed by 4 days of placebo tablets. As can be seen from the data presented in Table 10, the percentage of days of bleeding events per treatment cycle in obese women over a 28 day treatment cycle ranges from about 4.1% to about 6.4%, as compared to the percentage of days of bleeding events per treatment cycle in non-obese women, which ranges from about 11.9% to about 15.8%.

TABLE 10

Number of days with bleeding events by period of treatment cycles for a cohort of obese women, as compared with a cohort of non-obese women for the DRSP treatment.

| Treatment cycle | | BMI ≤ 29.9 kg/m² (N = 828) | % per treatment cycle | BMI ≥ 30 kg/m² (N = 30) | % per treatment cycle | Total (N = 858) | Wilcoxon-rank-sum-test p value |
|---|---|---|---|---|---|---|---|
| Cycles 2-4 | n | 511 | | 16 | | 527 | |
| | Mean | 13.3 | 15.8% | 5.3 | 6.3% | 13.1 | 0.0097 |
| | (SD) | (13.13) | | (6.66) | | (13.05) | |
| | Median | 10.0 | | 2.0 | | 10.0 | |
| | Min/Max | 0/66 | | 0/22 | | 0/66 | |
| Cycles 2-6 | n | 408 | | 14 | | 422 | |
| | Mean | 19.6 | 14.0% | 6.3 | 4.5% | 19.1 | 0.0053 |
| | (SD) | (18.88) | | (7.89) | | (18.77) | |
| | Median | 16.0 | | 2.0 | | 14.0 | |
| | Min/Max | 0/100 | | 0/24 | | 0/100 | |
| Cycles 2-9 | n | 291 | | 14 | | 305 | |
| | Mean | 30.4 | 13.6% | 9.2 | 4.1% | 29.4 | 0.0027 |
| | (SD) | (28.02) | | (12.10) | | (27.84) | |
| | Median | 22.0 | | 2.0 | | 21.0 | |
| | Min/Max | 0/109 | | 0/36 | | 0/109 | |
| Cycles 5-7 | n | 405 | | 18 | | 423 | |
| | Mean | 10.4 | 12.4% | 5.4 | 6.4% | 10.2 | 0.0217 |
| | (SD) | (11.18) | | (8.76) | | (11.13) | |
| | Median | 7.0 | | 1.5 | | 6.0 | |
| | Min/Max | 0/67 | | 0/29 | | 0/67 | |
| Cycles 7-9 | n | 356 | | 18 | | 374 | |
| | Mean | 10.0 | 11.9% | 3.8 | 4.5% | 9.7 | 0.0037 |
| | (SD) | (10.47) | | (6.62) | | (10.39) | |
| | Median | 7.0 | | 0.0 | | 6.0 | |
| | Min/Max | 0/60 | | 0/20 | | 0/60 | |

N: Number of subjects in the Test group in the particular BMI group
n: Number of subjects with data available
SD: Standard deviation Table 10 demonstrates the number of days with bleeding events in obese women, i.e., women having a BMI of 30 kg/m² or more, who are treated with the DRSP-based POC formulation (LF111). The mean number of days of bleeding events in obese women is:
(i) reduced by about 60.1% as compared to non-obese women subjected to the same contraceptive treatment, i.e., women having a BMI of 29.9 kg/m² or less, during the treatment cycles 2-4;
(ii) reduced by about 67.9% as compared to non-obese women subjected to the same contraceptive treatment during the treatment cycles 2-6;

In accordance with one embodiment, the average percentage of days of bleeding events per treatment cycle over at least eight consecutive treatment cycles subsequent to an initial treatment cycle was about 9.9% for women with excess weight (BMI≥25 kg/m²) and about 4.1% for obese women (BMI≥30 kg/m²). This is compared to the average percentage of days of bleeding events per treatment cycle over at least eight consecutive treatment cycles subsequent to an initial treatment cycle of about 14.3% for women without excess weight (BMI≤24.9 kg/m²) and about 13.6% for non-obese women (BMI≤29.9 kg/m²).

Example 8

Correlation Between BMI and DRSP-Based Treatment on One Hand and Change in Weight and Change in Heart Rate on the Other Hand 1. Methods Heart rate is understood as the number of times a person's heart beats per minute at rest (e.g., not exercising). Preferably, heart rate may be measured after a patient has been lying down for at least 5 minutes, preferably for at least 10 minutes, and most preferably for at least 15 minutes. Alternatively, heart rate may be measured upon waking in the morning and before rising from bed. Heart rate is an important indicator of health.

While a normal heart rate for adults may range from about 60 to about 100 beats per minute, a lower heart rate is indicative of a more efficient heart function and of cardiovascular fitness. While overweight and obese women are generally observed to have a higher heart rate than women of normal weight, it has also been found that a faster heart rate is a warning sign for increased cardiovascular problems and also as a predictor for obesity later in life. Women with higher heart rates have been found to be predisposed to obesity and diabetes mellitus. Shigetoh, et al., AM. J. HYPERTENSION, vol. 22, no. 2, pp. 151-155, February 2009. Higher heart rates are believed to be associated with metabolic syndrome, diabetes, formation of blood clots that can cause a stroke or heart attack, heart failure, fainting spells, and even sudden death.

Thus, the reduction in heart rate is extremely desirable, especially for overweight or obese women, as lowering heart rate may result in reducing the risk of developing various deleterious health conditions. It is believed that reductions in heart rate of at least 5 beats per minute, of at least 10 beats per minute and at least 15 beats per minute will provide significant reductions of such risk factors.

In this example, the LF111 formulation described in Example 7 was used.

The CF111/301 clinical trial protocol included 713 healthy sexually active women willing to use oral contraceptives enrolled in approximately 41 centres located in 5 countries (Hungary, Poland, the Czech Republic, Germany and Romania).

After signing an Informed Consent Form at visit 1a (screening) and receiving study medication at visit 1b, eligible subjects attended visits 2 to 6 at day 24±2 of the $1^{st}$, $3^{rd}$, $6^{th}$, $9^{th}$ and $13^{th}$ treatment cycle. The follow-up (visit 7) took place 10 to 28 days after visit 6. At least 515 subjects completed the study with 13 treatment cycles each.

Data set had information on demographic and clinical parameters, gynaecological and medical history data, laboratory and vital signs assessments, prior/concomitant medications/contraceptive devices related data.

Statistical p values were calculated by using a Fisher exact test, and p value was found significant test at the threshold p≤0.05.

2. Results

For women affected with obesity (BMI≥30 kg/m$^2$) a trend in decreasing their weight and heart rate from visit 1 (measured at baseline) to visit 6 (measured at the end of the study) was observed.

Figure 7:
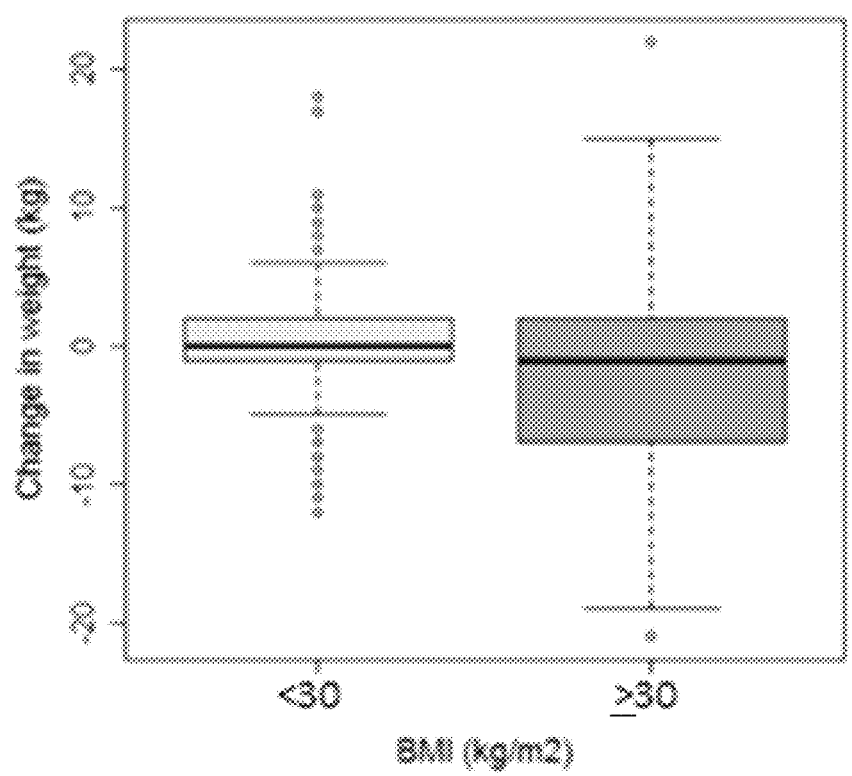
FIG. 7 is a plot illustrating the correlation between the body mass index (BMI) of women undertaking a DRSP-based contraceptive treatment with respect to the change in weight (kg). Change of weight is measured by subtracting the weight at visit 6 (day 24±2 of the $13^{th}$ treatment cycle) from the weight at screening. Any negative result is indicative of a weight loss. Women with a BMI lower than 30 kg/m² (left) did not present any average weight change, whereas women with a BMI greater than 30 kg/m² (right) presented a slight but significant change in weight during the course of the contraceptive treatment.
Figure 8:
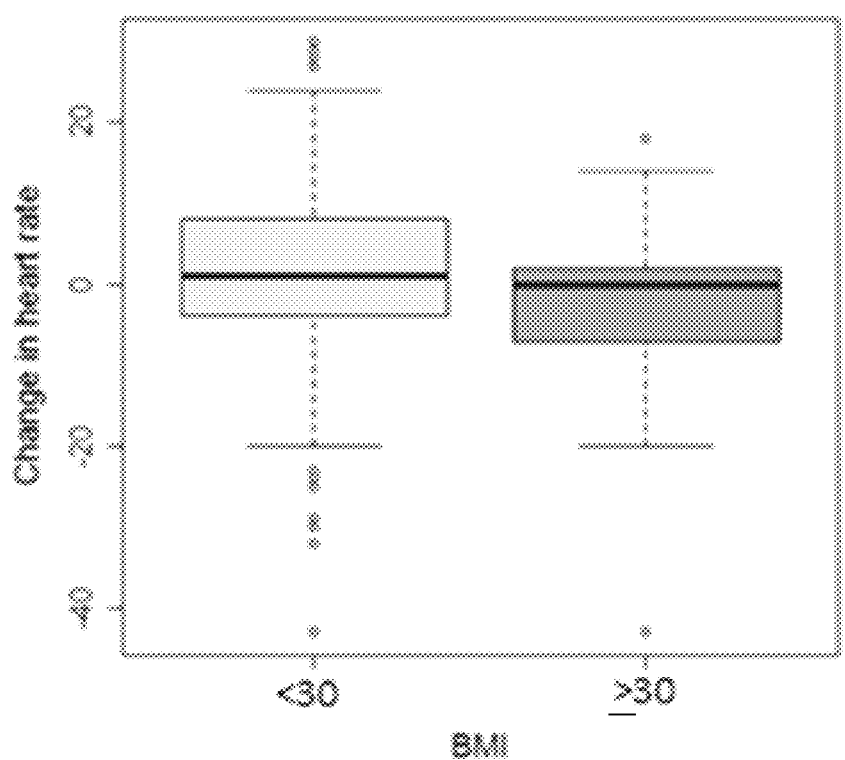
FIG. 8 is a plot illustrating the correlation between the body mass index (BMI) of women undertaking a DRSP-based contraceptive treatment with respect to the change in heart rate. Change in heart rate is measured by subtracting the heart rate at visit 6 (day 24±2 of the 13$^{th}$ treatment cycle) from the heart rate at screening. Any positive result is indicative of a higher heart rate during the course of the contraceptive treatment. Women with a BMI lower than 30 kg/m² (left) presented a slight but significant increase in the heart rate during the course of the contraceptive treatment, whereas women with a BMI greater than 30 kg/m² (right) did not present any change in the heart rate during the course of the contraceptive treatment.

Distribution of the change in weight and heart rate from visit 1 to 6 for women by BMI group (BMI<30 kg/m$^2$ and BMI≥30 kg/m$^2$) is shown in FIGS. 7 and 8 respectively.

The linear model analysis showed that the effect of BMI group was statistically significant in the change of weight (F-statistic: 14.49 on 1 and 668 DF, p-value: 0.0001541) and heart rate (F-statistic: 4.947 on 1 and 666 DF, p-value: 0.02647) from visit 1 to 6.

Thus, in one embodiment, administration of the pharmaceutical compositions disclosed herein to an obese patient results in a weight loss of about 1 kg to about 10 kg or about 1 kg to about 7 kg or about 1 kg to about 4 kg at the end of one of 2 through 9 treatment cycles from the patient's weight at the beginning of the initial treatment cycle of administration. The observed weight loss, in one embodiment, may occur at the end of 2, 3, 4, 5, 6, 7, 8, 9, 10, 11, 12, 13, 14, 15, 16, 17, 18, 19, 20, 21, 22, 23, 24, 25, 26, 27, 28, 29, 30 treatment cycles or more.

In one embodiment, administration of the pharmaceutical compositions disclosed herein to a patient with a BMI of about 25 kg/m$^2$ or more results in a weight loss of at least about 0.5 kg, about 1 kg. about 1.5 kg, about 2.0 kg, about 2.5 kg, about 3.0 kg, about 3.5 kg, about 4.0 kg, about 5.0 kg, about 5.5 kg, about 6.0 kg, about 6.5 kg, about 7.0 kg, about 7.5 kg, about 8.0 kg, about 8.5 kg, about 9.0 kg, about 9.5 kg, about 10.0 kg at the end of a first through thirtieth cycles of administration following an initial cycle of administration.

In another embodiment, administration of the pharmaceutical compositions disclosed herein to a patient with a BMI of at least about 30 kg/m$^2$ or more results in a weight loss of at least about 0.5 kg, about 1 kg. about 1.5 kg, about 2.0 kg, about 2.5 kg, about 3.0 kg, about 3.5 kg, about 4.0 kg, about 5.0 kg, about 5.5 kg, about 6.0 kg, about 6.5 kg, about 7.0 kg, about 7.5 kg, about 8.0 kg, about 8.5 kg, about 9.0 kg, about 9.5 kg, about 10.0 kg at the end of a first through thirtieth cycles of administration following an initial cycle of administration.

In another embodiment, administration of the pharmaceutical compositions disclosed herein to an obese patient results in a reduction in the patient's BMI of from about 1% to about 20%, from about 1% to about 10%, and from about 1% to about 5% at the end of one of a second through ninth treatment cycle from the patient's weight at the beginning of the initial treatment cycle of administration. The observed reduction in BMI, in one embodiment, may occur at the end of 2, 3, 4, 5, 6, 7, 8, 9, 10, 11, 12, 13, 14, 15, 16, 17, 18, 19, 20, 21, 22, 23, 24, 25, 26, 27, 28, 29, 30 treatment cycles or more.

In one embodiment, administration of the pharmaceutical compositions disclosed herein to a patient with a BMI of about 25 kg/m$^2$ or more results in a reduction in the patient's BMI of at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% at the end of a first through thirtieth cycles of administration following an initial cycle of administration.

In another embodiment, administration of the pharmaceutical compositions disclosed herein to a patient with a BMI at least about 30 kg/m$^2$ or more results in a reduction in the patient's BMI of at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% at the end of a first through thirtieth cycles of administration following an initial cycle of administration.

In one embodiment, administration of the pharmaceutical compositions disclosed herein to a patient with excess weight or to an obese patient results in a decrease in the resting heart rate of at least 15 beats per minute or at least 10 beats per minute or at least 5 beats per minute at the end of one of a second through ninth treatment cycle from the patient's resting heart rate at the beginning of the initial treatment cycle of administration. Alternatively, the decrease in the resting heart rate may be from about 2% to about 20%, from about 2% to about 15%, or from about 2% to about 10%, from about 5% to about 7%. The observed decrease in resting heart rate, in one embodiment, may also occur at the end of 2, 3, 4, 5, 6, 7, 8, 9, 10, 11, 12, 13, 14, 15, 16, 17, 18, 19, 20, 21, 22, 23, 24, 25, 26, 27, 28, 29, 30 treatment cycles or more.

In another embodiment, administration of the pharmaceutical compositions disclosed herein to a patient with a BMI of about 25 kg/m² or more, or to a patient with a BMI at least about 30 kg/m² or more, results in a decrease in the average resting heart rate of up to about 15 beats per minute, about 14 beats per minute, about 13 beats per minute, about 12 beats per minute, about 11 beats per minute, about 10 beats per minute, about 9 beats per minute, about 8 beats per minute, about 7 beats per minute, about 6 beats per minute, about 5 beats per minute over subsequent consecutive treatment cycles following an initial cycle of administration. The subsequent consecutive treatment cycles may be provided any range including and between one and thirtieth cycles of administration following an initial cycle of administration. Alternatively, The observed decrease in resting heart rate, in one embodiment, may occur at the end of 2, 3, 4, 5, 6, 7, 8, 9, 10, 11, 12, 13, 14, 15, 16, 17, 18, 19, 20, 21, 22, 23, 24, 25, 26, 27, 28, 29, 30 treatment cycles or more.

Example 9

Reduced Adverse Effects of the DRSP-Based Treatment in Obese Women

1. Methods

The CF111/ISS clinical trial protocol included 1571 (1500+71) healthy sexually active women willing to use oral contraceptives enrolled in approximately 114 centers located in Austria, Czech Republic, German, Hungary, Poland, Romania Slovaki, and Spain. A group of non-obese women (BMI<30 kg/m²) and of obese women (BMI≥30 kg/m²) were studied separately.

Table 11 depicts the results of quantification of TEAEs (Treatment Emergent Adverse Events) in a cohort of women subject to contraception with a drospirenone-containing composition according to one preferred embodiment ("LF111"). Non-obese women (BMI<30 kg/m²) and obese women (BMI≥30 kg/m²) were studied, respectively.

The results disclosed in Table 11 show that the percentage of TEAEs was similar in women subjected to DRSP-POC formulation, irrespective of whether these women are obese or not. Thus, the results show that the drospirenone-containing formulation according to the preferred embodiments is likely to have a high compliance or observance rate among obese women.

TEAE: Treatment Emergent Adverse Event. Adverse events are coded using MedDRA version 15.1. TEAEs are defined as AEs which started at or after the first administration of an IMP and includes those events started prior to the first administration of an IMP but which worsened after the first intake. Adverse events starting after the last administration of an IMP but within the follow up period after last IMP will be regarded as treatment-emergent.

TABLE 11

Incidence of TEAEs by BMI subgroup of individuals

| | BMI < 30 kg/m² (N = 1500) n (%) | BMI ≥ 30 kg/m² (N = 71) |
|---|---|---|
| Subjects with at least one TEAEs | 650 (43.3%) | 30 (42.3%) |

N: Number of subjects in specified treatment group.
n: Number of subjects with adverse events.
%: Percentage based on N

The invention claimed is:

1. A method of providing contraception in a patient having a BMI of 30 kg/m² or more and bleeding events, the method comprising:
   administering a pharmaceutical composition comprising 2.5 mg to 5.5 mg crystalline of drospirenone and one or more pharmaceutically-acceptable excipients to a patient having a BMI of 30 kg/m² or more for an initial treatment cycle and for subsequent consecutive treatment cycles, the pharmaceutical composition being administered daily for at least a portion of the initial and subsequent consecutive treatment cycles;
   wherein the administering results in a limited number of days of bleeding events per treatment cycle in at least one of the subsequent consecutive treatment cycles.

2. The method of claim 1, wherein the limited number of days of bleeding events in the at least one of the subsequent consecutive treatment cycles of administration does not exceed about 13% per treatment cycle.

3. The method of claim 1, wherein the limited number of days of bleeding events in the at least one of the subsequent consecutive treatment cycles of administration does not exceed about 11% per treatment cycle.

4. The method of claim 1, wherein the limited number of days of bleeding events in the at least one of the subsequent consecutive treatment cycles of administration does not exceed about 10% per treatment cycle.

5. The method of claim 1, wherein the limited number of days of bleeding events in the at least one of the subsequent consecutive treatment cycles of administration does not exceed about 7%.

6. The method of claim 1, wherein the limited number of days of bleeding events in the at least one of the subsequent consecutive treatment cycles of administration does not exceed about 5%.

7. The method of claim 1, wherein the number of days of limited bleeding events in one of a second through ninth treatment cycles is reduced by about 44% to about 85% as compared to the initial treatment cycle.

8. The method of claim 7, wherein the number of days of limited bleeding events in one of the second through ninth treatment cycle is reduced by about 50% to about 75% as compared to the initial treatment cycle.

9. The method of claim 1, wherein the number of days of limited bleeding events in one of the second through the ninth treatment cycle is reduced by at least about 20% as compared to the initial treatment cycle.

10. The method of claim 9, wherein the number of days of limited bleeding events in one of the second through ninth treatment cycle is reduced by at least about 40% as compared to the initial treatment cycle.

11. The method of claim 10, wherein the number of days of limited bleeding events in one of the second through ninth treatment cycle is reduced by at least about 60% as compared to the initial treatment cycle.

12. The method of claim 1, wherein the administering causes weight loss in the patient measured from the initial treatment cycle and an end of one of a first through thirtieth subsequent consecutive treatment cycles.

13. The method of claim 12, wherein the weight loss is about 1 kg to about 10 kg.

14. The method of claim 12, wherein the weight loss is about 1 kg to about 4 kg.

15. The method of claim 12, wherein the weight loss results in a reduction in the patient's BMI of about 1% to about 20%.

16. The method of claim 12, wherein the weight loss results in a reduction in the patient's BMI of about 1% to about 5%.

17. The method of claim 1, wherein the administration of the pharmaceutical composition causes a decrease in a resting heart rate in the patient as measured from the initial treatment cycle and an end of one of a first through thirtieth subsequent consecutive treatment cycles.

18. The method of claim 17, wherein the decrease in the resting heart rate is at least 5 beats per minute.

19. The method of claim 18, wherein the decrease in the resting heart rate is at least 15 beats per minute.

20. The method of claim 17, where the decrease in the resting heart rate is about 2% to about 20%.

21. The method of claim 20, wherein the decrease in the resting heart rate is about 5% to about 7%.

22. The method of claim 1, wherein the subsequent consecutive treatment cycles are a first to thirtieth treatment cycles following the initial treatment cycle of administration.

23. The method of claim 1, wherein the drospirenone is non-micronized.

24. The method of claim 1, wherein the drospirenone is provided in a particle form.

25. The method of claim 24, wherein the particle form has a specific surface area from about 2,000 $cm^2/g$ to about 8,500 $cm^2/g$.

26. The method of claim 24, wherein the particle form has a diameter of about 200 μm or less.

27. The method of claim 24, wherein the particle form has a $d_{50}$ in the range of about 10 μm to about 60 μm.

28. The method of claim 24, wherein a particle size distribution of the active contraceptive drug is characterized by:
   (i) a $d_{90}$ particle size less than about 100 μm, and/or
   (ii) a $d_{50}$ particle size ranging from about 10 μm to about 60 μm, and/or
   (iii) a $d_{10}$ particle size more than about 3 μm.

29. The method of claim 28, wherein the $d_{90}$ particle size ranges from about 20 μm to about 40 μm.

30. The method of claim 28, wherein the $d_{50}$ particle size ranges from about 10 μm to about 30 μm.

31. The method of claim 28, wherein the $d_{10}$ particle sizes range from about 3 μm to about 9 μm.

32. The method of claim 1, wherein the crystalline drospirenone is present in an amount of 2 mg to 6 mg.

33. The method of claim 32, wherein the crystalline drospirenone is present in an amount of 4 mg.

34. The method of claim 1, wherein the pharmaceutical composition does not include estrogen.

35. The method of claim 34, wherein the pharmaceutical composition is provided in a single daily oral tablet dosage form.

36. The method of claim 35, wherein the pharmaceutical composition comprising 3.2 mg to 4.8 mg of crystalline drospirenone.

37. The method of claim 36, wherein the pharmaceutical composition provides a pharmacokinetic profile for the drospirenone having: i) $T_{max}$ ranging from about 2.2 hours to 6 hours and ii) a mean $C_{max}$ which is less than 30 ng/ml when orally administered to the patient under fasting conditions.

38. The method of claim 37, wherein the pharmacokinetic profile for the drospirenone additionally comprises an $AUC_{0h\text{-}tlast}$ which is at least 300 ng·h/ml.

39. The method of claim 37, wherein the mean $C_{max}$ ranges from 15 ng/ml to 30 ng/ml.

40. The method of claim 36, wherein when the pharmaceutical composition is subjected to an in vitro dissolution test according to the USP XXIII Paddle Method: no more than 50% of the drospirenone initially present in the pharmaceutical composition is dissolved within 30 minutes, and at least 50% of the drospirenone is dissolved in a time range from 3 hours to 4 hours.

* * * * *